(12) United States Patent
Dorsch et al.

(10) Patent No.: US 7,273,867 B2
(45) Date of Patent: Sep. 25, 2007

(54) PHENYL DERIVATIVES

(75) Inventors: Dieter Dorsch, Ober-Ramstadt (DE); Werner Mederski, Zwingenberg (DE); Christos Tsaklakidis, Weinheim (DE); Bertram Cezanne, Moerfelden-Walldorf (DE); Johannes Gleitz, Darmstadt (DE); Christopher Barnes, Bad Soden (DE)

(73) Assignee: Merck Patent GmbH, Darmstadt (DE)

( * ) Notice: Subject to any disclaimer, the term of this patent is extended or adjusted under 35 U.S.C. 154(b) by 233 days.

(21) Appl. No.: 10/466,680

(22) PCT Filed: Dec. 5, 2001

(86) PCT No.: PCT/EP01/14296

§ 371 (c)(1), (2), (4) Date: Dec. 18, 2003

(87) PCT Pub. No.: WO02/057236

PCT Pub. Date: Jul. 25, 2002

(65) Prior Publication Data

US 2004/0087582 A1    May 6, 2004

(30) Foreign Application Priority Data

Jan. 19, 2001   (DE) .............. 101 02 322.7

(51) Int. Cl.
- *A61K 31/535* (2006.01)
- *A61K 31/497* (2006.01)
- *A61K 31/445* (2006.01)
- *A61K 31/44* (2006.01)
- *A61K 31/41* (2006.01)

(52) U.S. Cl. ............. 514/239.5; 514/252.1; 514/327; 514/346; 514/364; 544/166; 544/408; 546/221; 546/292; 548/131; 548/229; 558/413; 558/414

(58) Field of Classification Search ........... 544/166, 544/408; 546/221, 292; 548/131, 229; 558/413, 558/414; 564/51, 163; 514/239.5, 252, 514/327, 346, 364, 374, 597, 619
See application file for complete search history.

(56) References Cited

U.S. PATENT DOCUMENTS 2,361,327 A * 10/1944 Sparks ............... 564/167
4,761,175 A *  8/1988 Schirmer et al. ........ 504/303
2003/0176465 A1    9/2003 Mederski et al.

FOREIGN PATENT DOCUMENTS

WO   WO 9916751 A    4/1999
WO   WO 0071510 A   11/2000
WO   WO 0206269 A    1/2002

OTHER PUBLICATIONS

Ting Su et al: "Design and Synthesis of Glycolic and Mandelic Acid derivatives as Factor Xa Inhibitors" Bioorgnic and Medicinal Chemistry Letters, vol. 11, No. 17, 2001, pp. 2279-2282 XP001069180.

* cited by examiner

*Primary Examiner*—Johann R. Richter
*Assistant Examiner*—Ebenezer Sackey
(74) *Attorney, Agent, or Firm*—Millen, White, Zelano & Branigan, P.C.

(57) ABSTRACT

Novel compounds of the formula I in which W, X, Y, T, $R^1$ and $R^2$ are as defined in Patent claim 1, are inhibitors of coagulation factor Xa and can be employed for the prophylaxis and/or therapy of thromboembolic disorders

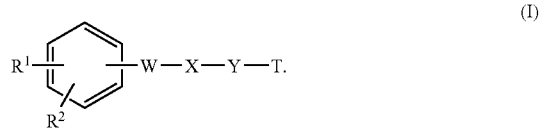

14 Claims, No Drawings

PHENYL DERIVATIVES

The invention relates to compounds of the formula I

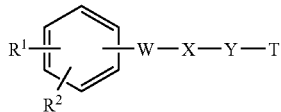

in which
R$^1$ is CN, CON(R$^3$)$_2$, —[C(R$^4$)$_2$]$_n$N(R$^3$)$_2$, —C(=NH)—NH$_2$ which is unsubstituted or monosubstituted by C(=O)R$^3$, COOR$^3$, OR$^3$, OCOR$^3$, OCOOR$^3$ or by a conventional amino-protecting group, or is

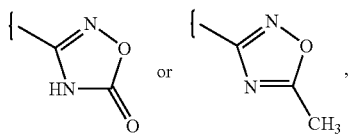

R$^2$ is H, Hal, A, OR$^3$, N(R$^3$)$_2$, NO$_2$, CN, COOR$^3$, CON(R$^3$)$_2$, —[C(R$^4$)$_2$]$_n$—Ar, —[C(R$^4$)$_2$]$_n$-Het or —[C(R$^4$)$_2$]$_n$-cycloalkyl,
R$^3$ is H, A, —[C(R$^4$)$_2$]$_n$—Ar, —[C(R$^4$)$_2$]$_n$-Het or —[C(R$^4$)$_2$]$_n$-cycloalkyl,
R$^4$ is H or A,
W is —C(R$^3$)$_2$—, —[C(R$^3$)$_2$]$_2$—, —OC(R$^3$)$_2$— or —NR$^3$C(R$^3$)$_2$—,
X is CONR$^3$, CONR$^3$C(R$^4$)$_2$—, —C(R$^4$)$_2$NR$^3$—, —C(R$^4$)$_2$NR$^3$C(R$^4$)$_2$—, —C(R$^4$)$_2$O— or —C(R$^4$)$_2$OC(R$^4$)$_2$—,
Y is alkylene, cycloalkylene, Het-diyl or Ar-diyl,
T is OR$^3$, N(R$^3$)$_2$ or a monocyclic or bicyclic, saturated, unsaturated or aromatic heterocyclic radical having from 1 to 4 N, O and/or S atoms which is unsubstituted or monosubstituted, disubstituted or trisubstituted by Hal, A, —[C(R$^4$)$_2$]$_n$—Ar, —[C(R$^4$)$_2$]$_n$-Het, —[C(R$^4$)$_2$]$_n$-cycloalkyl, OR$^3$, N(R$^3$)$_2$, NO$_2$, CN, COOR$^3$, CON(R$^3$)$_2$, NR$^3$COA, NR$^3$SO$_2$A, COR$^3$, SO$_2$NR$^3$, S(O)$_m$A and/or carbonyl oxygen,
A is unbranched or branched alkyl having 1-6 carbon atoms, in which one or two CH$_2$ groups may be replaced by O or S atoms and/or by —CH=CH— groups and/or, in addition, 1-7 H atoms may be replaced by F,
Ar is phenyl, naphthyl or biphenyl, each of which is unsubstituted or monosubstituted, disubstituted or trisubstituted by Hal, A, OR$^4$, N(R$^4$)$_2$, NO$_2$, CN, COOR$^4$, CON(R$^4$)$_2$, NR$^4$COA, NR$^4$SO$_2$A, COR$^4$, SO$_2$NR$^4$, S(O)$_m$A, —[C(R$^4$)$_2$]$_n$—COOR$^3$ or O—[C(R$^4$)$_2$]$_o$—COOR$^3$,
Het is a monocyclic or bicyclic, saturated, unsaturated or aromatic heterocyclic radical having from 1 to 4 N, O and/or S atoms which is unsubstituted or monosubstituted, disubstituted or trisubstituted by Hal, A, —[C(R$^4$)$_2$]$_n$—Ar, —[C(R$^4$)$_2$]$_n$-Het', —[C(R$^4$)$_2$]$_n$-cycloalkyl, OR$^3$, N(R$^3$)$_2$, NO$_2$, CN, COOR$^3$, CON(R$^3$)$_2$, NR$^3$COA, NR$^3$SO$_2$A, COR$^3$, SO$_2$NR$^3$, S(O)$_m$A and/or carbonyl oxygen,
Het' is a monocyclic or bicyclic, saturated, unsaturated or aromatic heterocyclic radical having from 1 to 4 N, O and/or S atoms which is unsubstituted or monosubstituted or disubstituted by Hal, A, OR$^3$, N(R$^3$)$_2$, NO$_2$, CN, COOR$^3$, CON(R$^3$)$_2$, NR$^3$COA, NR$^3$SO$_2$A, COR$^3$, SO$_2$NR$^3$, S(O)$_m$A and/or carbonyl oxygen,
Hal is F, Cl, Br or I,
m and
n are each, independently of one another, 0, 1 or 2,
o is 1, 2 or 3, and their pharmaceutically usable derivatives, solvates and stereoisomers, including mixtures thereof in all ratios.

The invention had the object of finding novel compounds having valuable properties, in particular those which can be used for the preparation of medicaments.

It has been found that the compounds of the formula I and their salts have very valuable pharmacological properties and are well tolerated. In particular, they exhibit factor Xa-inhibiting properties and can therefore be employed for combating and preventing thromboembolic disorders, such as thrombosis, myocardial infarction, arteriosclerosis, inflammation, apoplexia, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are disclosed, for example, in EP 0 540 051 B1, WO 00/71508, WO 00/71511, WO 00/71493, WO 00/71507, WO 00/71509, WO 00/71512, WO 00/71515 and WO 00/71516. Cyclic guanidines for the treatment of thromboembolic disorders are described, for example, in WO 97/08165. Aromatic heterocyclic compounds having factor Xa-inhibitory activity are disclosed, for example, in WO 96/10022. Substituted N-[(aminoiminomethyl)phenylalkyl]azaheterocyclylamides as factor Xa inhibitors are described in WO 96/40679.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic disorders. However, inhibition of thrombin may inhibit the fibrin formation involved in thrombus formation. The inhibition of thrombin can be measured, for example, by the method of G. F. Cousins et al. in *Circulation* 1996, 94, 1705-1712.

Inhibition of factor Xa can thus prevent the formation of thrombin. The compounds of the formula I according to the invention and their salts engage in the blood coagulation process by inhibiting factor Xa and thus inhibit the formation of thromboses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example, by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation. The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

The compounds according to the invention may furthermore be used for the treatment of tumours, tumour illnesses and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumoural action of TF-VII and factor Xa inhibitors for various types of tumour:
K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92

The compounds of the formula I can be employed as medicament active ingredients in human and veterinary medicine, in particular for the treatment and prevention of thromboembolic disorders, such as thrombosis, myocardial infarction, arteriosclerosis, inflammation, apoplexia, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease.

The compounds are also employed in combination with other thrombolytic agents in the case of myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in vivo in patients, or as anticoagulants for the preservation of blood, plasma and other blood products in vitro. The compounds according to the invention are furthermore used for illnesses in which blood coagulation makes a crucial contribution to the course of the illness or represents a source of secondary pathology, such as, for example, in cancer, including metastasis, inflammatory disorders, including arthritis, and diabetes.

In the treatment of the illnesses described, the compounds according to the invention are also employed in combination with other thrombolytically active compounds, such as, for example, with "tissue plasminogen activator" t-PA, modified t-PA, streptokinase or urokinase. The compounds according to the invention are given either at the same time as or before or after the other substances mentioned.

Particular preference is given to simultaneous administration with aspirin in order to prevent recurrence of the clot formation.

The compounds according to the invention are also used in combination with blood platelet glycoprotein receptor (IIb/IIIa) antagonists, which inhibit blood platelet aggregation.

The invention relates to the compounds of the formula I and their salts and to a process for the preparation of compounds of the formula I according to claim 1 and their salts, characterised in that
a) they are liberated from one of their functional derivatives by treatment with a solvolysing or hydrogenolysing agent by
 i) liberating an amidino group from their hydroxyl, oxadiazole or oxazolidinone derivative by hydrogenolysis or solvolysis,
 ii) replacing a conventional amino-protecting group by hydrogen by treatment with a solvolysing or hydrogenolysing agent, or liberating an amino group protected by a conventional protecting group, or b) converting a cyano group into an amidino group, or c) reacting a compound of the formula II

Z—Y-T                                                II in which
Z is $HNR^3$— or $HNR^3C(R^4)_2$— and $R^3$, $R^4$, Y and T are as defined in claim 1,
with a compound of the formula III

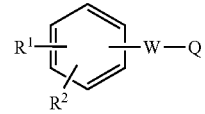

III in which
$R^1$ is —C(=NH)—$NH_2$ which is monosubstituted by C(=O)$R^3$, COOR$^3$, OR$^3$ or by a conventional amino-protecting group, or is

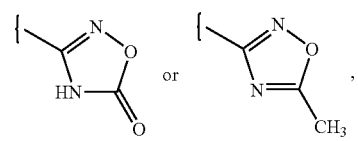

Q is —CO-L or —C($R^4$)$_2$-L,
L is Cl, Br, I or a free or reactively functionally modified OH group, and
and $R^2$, $R^3$, $R^4$ and W are as defined in claim 1, and/or d) converting a base or acid of the formula I into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates or dihydrates or alcoholates.

The term pharmaceutically usable derivatives is taken to mean, for example, the salts of the compounds according to the invention and also so-called prodrug compounds.

The term prodrug derivatives is taken to mean compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The invention also relates, in particular, to the —C(=NH)—NH$_2$— compounds of the formula I which are substituted by —COA, —COOA, —OH or by a conventional amino-protecting group.

For all radicals which occur more than once, such as, for example, A, their meanings are independent of one another.

Above and below, the radicals or parameters W, X, Y, T, R$^1$ and R$^2$ are as defined under the formula I, unless expressly stated otherwise.

A is alkyl, is unbranched (linear) or branched, and has 1, 2, 3, 4, 5, 6, 7, 8, 9 or 10 carbon atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A is very particularly preferably alkyl having 1-6 carbon atoms, preferably methyl, ethyl, propyl, isopropyl, butyl, isobutyl, sec-butyl, tert-butyl, pentyl, hexyl or trifluoromethyl.

Cycloalkyl is preferably cyclopropyl, cyclobutyl, cyclopentyl, cyclohexyl or cycloheptyl.

Alkylene is preferably methylene, ethylene, propylene, butylene, pentylene or hexylene, furthermore branched alkylene.

—COR$^3$ (acyl) is preferably formyl, acetyl, propionyl, furthermore also butyryl, pentanoyl, hexanoyl or, for example, benzoyl.

Ph is phenyl, Me is methyl, Et is ethyl, BOC is tert-butoxycarbonyl.

Hal is preferably F, Cl or Br, but alternatively I.

If R$^1$ is CON(R$^3$)$_2$ or —[C(R$^4$)$_2$]$_n$N(R$^3$)$_2$, CONH$_2$, NH$_2$ or CH$_2$NH$_2$ is preferred.

R$^1$ is particularly preferably CN, CONH$_2$, CONA$_2$, NH$_2$, CH$_2$NH$_2$, CH$_2$CH$_2$NH$_2$, —C(=NH)—NH$_2$ which is unsubstituted or monosubstituted by OH, OCOA or OCOOA, or is

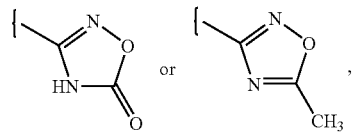

where A is preferably alkyl having 1, 2, 3 or 4 carbon atoms.

R$^2$ is preferably H or F.

R$^3$ is preferably H, A or —(CH$_2$)$_n$—Ar, particularly preferably, for example, H, alkyl having 1-6 carbon atoms, phenyl or benzyl.

W is preferably —C(R$^3$)$_2$—, —OC(R$^3$)$_2$— or —NR$^3$C(R$^3$)$_2$—, particularly preferably, for example, —OCHR$^3$ or —NHCHR$^3$, where R$^3$ is H, alkyl having 1, 2, 3, 4, 5 or 6 carbon atoms, in which 3 H atoms may be replaced by F, or phenyl, benzyl or thienyl, each of which is unsubstituted or monosubstituted or disubstituted by F, methyl or ethyl.

X is preferably CONH or CONH(CH$_2$)$_2$—, particularly preferably CONH or CONHCH$_2$, furthermore CH$_2$O— or CH$_2$OCH$_2$.

Y is preferably alkylene or Ar-diyl, particularly preferably methylene, ethylene, propylene, or 1,4-phenylene which is unsubstituted or monosubstituted by F, ethoxycarbonylmethoxy or carboxymethoxy, furthermore alternatively pyridinedyl, preferably pyridine-2,5-diyl.

T is preferably N(R$^{3'}$)$_2$ or a monocyclic or bicyclic, saturated, unsaturated or aromatic heterocyclic radical having 1 to 2 N and/or O atoms, which is unsubstituted or monosubstituted or disubstituted by A and/or carbonyl oxygen, where R$^{3'}$ is H or A.

T is particularly preferably, for example, dimethylamino, diethylamino, morpholin-4-yl, 2-oxopiperidin-1-yl, 2-oxopyrrolidin-1-yl, 5,5-dimethyl-2oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,5-dioxopyrrolidin-1-yl, 2-oxo-1,3-oxazolidin-3-yl, 2-azabicyclo[2.2.2]octan-3-on-2yl or 3-oxo-2H-pyridazin-2-yl.

Ar is, for example, phenyl which is unsubstituted or monosubstituted, disubstituted or trisubstituted by Hal, A, OR$^4$, —[C(R$^4$)$_2$]$_n$—COOR$^3$ or O—[C(R$^4$)$_2$]$_o$—COOR$^3$.

Ar is preferably unsubstituted phenyl, naphthyl or biphenyl, furthermore preferably phenyl, naphthyl or biphenyl, each of which is monosubstituted, disubstituted or trisubstituted, for example, by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, ethoxycarbonylmethoxy, carboxymethoxy or aminocarbonyl.

Ar is particularly preferably, for example, phenyl which is unsubstituted or monosubstituted or disubstituted by Hal, A, methoxy, methoxycarbonylmethoxy, carboxymethoxy or ethoxycarbonylmethoxy.

Het is preferably, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6-, or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-quinolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 1,3-benzothiadiazol-4- or -5-yl or 2,1,3-benzoxadiazol-5-yl.

The heterocyclic radicals may also be partially or fully hydrogenated. Het can thus, for example, also be 2,3-dihydro-2-, -3-, 4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, 4- or -5-pyrrolyl, 1-, 2- or 3-pyrrolidinyl, tetrahydro-1-, -2- or -4-imidazolyl, 2,3-dihydro-1-, -2-, -3-, 4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

Het is very particularly preferably a monocyclic or bicyclic, saturated, unsaturated or aromatic heterocyclic radical having 1 to 2 N or O atoms which is unsubstituted or monosubstituted or disubstituted by carbonyl oxygen, such as, for example, morpholin-4-yl, 2-oxopiperidin-1-yl, 2-oxopyrrolidin-1-yl, 5,5-dimethyl-2-oxopyrrolidin-1-yl, 2-oxo-1H-pyridin-1-yl, 3-oxomorpholin-4-yl, 4-oxo-1H-pyridin-1-yl, 2,6-dioxopiperidin1-yl, 2-oxopiperazin-1-yl, 2,5-dioxopyrrolidin-1-yl, 2-oxo-1,3-oxazolidin-3-yl, 3-oxo-2H-pyridazin-2-yl, 2-caprolactam-1yl, 2-oxo-1,3-oxazinan-3-yl or 2-azabicyclo[2.2.2]octan-3-on-2yl.

Het' is preferably, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or -5-yl, 1- or 5-tetrazolyl 1,2,3-oxadiazol4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6-, 7- or 2-, 4-, 5-, 6- or 7-benzisothiazolyl, 4-, 5-, 6- or 7-benz-2,1,3-oxadiazolyl, 2-, 3-, 4-, 5-, 6-, 7- or 8quinolyl, 1-, 3-, 4-, 5-, 6-, 7- or 8-isoquinolyl, 3-, 4-, 5-, 6-, 7- or 8-quinolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het' can thus, for example, also be 2,3-dihydro-2-, -3-, 4- or -5-furyl, 2,5-dihydro-2-, -3-, 4- or -5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, 4- or -5-pyrrolyl, 1-, 2- or 3-pyrrolidinyl, tetrahydro-1-, -2- or -4-imidazolyl, 2,3-dihydro-1-, -2-, -3-, 4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, 4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, 4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-2-, -3-, 4-, -5-, -6-, -7- or -8-isoquinlyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

m is preferably 2, furthermore alternatively 0 or 1.

n is preferably 1, furthermore alternatively 0 or 2.

The compounds of the formula I may have one or more chiral centres and therefore occur in various stereoisomeric forms. The formula I covers all these forms.

Accordingly, the invention relates in particular to the compounds of the formula I in which at least one of the said radicals has one of the preferred meanings indicated above. Some preferred groups of compounds may be expressed by the following sub-formulae Ia to Im, which conform to the formula I and in which the radicals not designated in greater detail are as defined under the formula I, but in which in Ia $R^2$ is H;

in Ib $R^1$ is —C(=NH)—NH$_2$ which is unsubstituted or monosubstituted by OH, or is

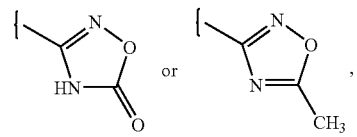

in Ic Ar is phenyl which is unsubstituted or monosubstituted or disubstituted by Hal, A, OR$^4$ or O—[C(R$^4$)$_2$]$_o$—COOR$^3$;

in Id Het is a monocyclic or bicyclic, saturated, unsaturated or aromatic heterocyclic radical having 1 to 2 N and/or O atoms which is monosubstituted or disubstituted by A and/or carbonyl oxygen;

in Ie W is —OC(R$^3$)$_2$— or —NR$^3$C(R$^3$)$_2$—;

in If W is —OC(R$^3$)$_2$— or —NR$^3$C(R$^3$)$_2$—, $R^3$ is H, A or —(CH$_2$)$_n$—Ar,

Ar is phenyl which is unsubstituted or monosubstituted or disubstituted by Hal, A, OR$^4$ or O—[C(R$^4$)$_2$]$_o$—COOR$^3$, n is 0 or 1;

in Ig W is —OCHR$^3$— or —NHCHR$^3$—, $R^3$ is H, A or —(CH$_2$)$_n$—Ar,

Ar is phenyl which is unsubstituted or monosubstituted or disubstituted by Hal, A, $OR^4$ or $O-[C(R^4)_2]_o-COOR^3$,
n is 0 or 1;
in Ih X is $CONH$ or $CONH(CH_2)_2-$;
in Ii Y is alkylene or Ar-diyl,
Ar is phenyl which is unsubstituted or monosubstituted or disubstituted by Hal, A, $OR^4$ or $O-[C(R^4)_2]_o-COOR^3$;
in Ij T is $N(R^{3'})_2$ or a monocyclic or bicyclic, saturated, unsaturated or aromatic heterocyclic radical having 1 to 2 N and/or O atoms which is monosubstituted or disubstituted by A and/or carbonyl oxygen,
$R^3$ is H or A;
in Ik $R^1$ is $-C(=NH)-NH_2$ which is unsubstituted or monosubstituted by OH, or is

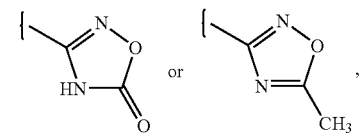

$R^2$ is H,
$R^3$ is H, A or $-(CH_2)_n-Ar$,
$R^4$ is H or A,
W is $-OC(R^3)_2-$ or $-NR^3C(R^3)_2-$,
X is CONH or $CONH(CH_2)_2$,
Y is alkylene or Ar-diyl,
T is $N(R^{3'})_2$ or a monocyclic or bicyclic, saturated, unsaturated or aromatic heterocyclic radical having 1 to 2 N and/or O atoms which is monosubstituted or disubstituted by A and/or carbonyl oxygen,
$R^{3'}$ is H or A,
Ar is phenyl which is unsubstituted or monosubstituted or disubstituted by Hal, A, $OR^4$ or $O-[C(R^4)_2]_o-COOR^3$,
A is unbranched or branched alkyl having 1-6 carbon atoms, in which 1-7 H atoms may be replaced by F,
n is 0 or 1;
in Il $R^1$ is $-C(=NH)-NH_2$ which is unsubstituted or monosubstituted by OH, or is

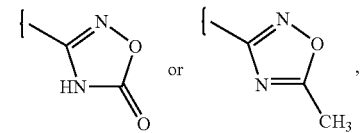

$R^2$ is H,
$R^3$ is H, A or $-(CH)_n-Ar$,
$R^4$ is H or A,
W is $-OC(R^3)_2-$ or $-NR^3C(R^3)_2-$,
X is CONH or $CONH(CH_2)_2$,
Y is alkylene or Ar-diyl,
T is dimethylamino, diethylamino, morpholin-4-yl, 2-oxopiperidin-1-yl, 2-oxopyrrolidin-1-yl, 5,5-dimethyl-2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,5-dioxopyrrolidin-1-yl, 2-oxo-1,3-oxazolidin-3-yl, 2-azabicyclo[2.2.2]octan-3-on-2-yl or 3-oxo-2H-pyridazin-2-yl, Ar is phenyl which is unsubstituted or monosubstituted or disubstituted by Hal, A, $OR^4$ or $O-[C(R^4)_2]_o-COOR^3$,
A is unbranched or branched alkyl having 1-6 carbon atoms, in which 1-7 H atoms may be replaced by F,
n is 0 or 1;
in Im $R^1$ is CN, $NH_2$, $CONA_2$, $CH_2NH_2$, $CH_2CH_2NH_2$, $-C(=NH)-NH_2$ which is unsubstituted or monosubstituted by OH, $COOR^3$, OCOA or OCOOA, or is

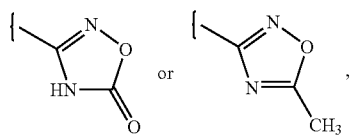

$R^2$ is H or F,
$R^3$ is H, A or $-(CH_2)_n-Ar$ or thienyl,
$R^4$ is H or A,
W is $-C(R^3)_2-$, $-OC(R^3)_2-$ or $-NR^3C(R^3)_2-$,
X is CONH, $CONH(CH_2)$, $CONH(CH_2)_2$, $CH_2O-$ or $CH_2OCH_2$,
Y is alkylene, Ar-diyl or pyridinediyl,
T is dimethylamino, diethylamino, morpholin-4-yl, 2-oxopiperidin-1-yl, 2-oxopyrrolidin-1-yl, 5,5-dimethyl-2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl, 2-oxo-1,3-oxazinan-3-yl or 2-azabicyclo[2.2.2]octan-3-on-2-yl,
Ar is phenyl which is unsubstituted or monosubstituted or disubstituted by Hal, $CF_3$, A, OA, methoxycarbonylmethoxy, ethoxycarbonylmethoxy or carboxymethoxy,
A is unbranched or branched alkyl having 1-6 carbon atoms, in which 1-7 H atoms may be replaced by F,
n is 0 or 1;

and their pharmaceutically usable derivatives, solvates and stereoisomers, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

Compounds of the formula I can preferably be obtained by liberating compounds of the formula I from one of their functional derivatives by treatment with a solvolysing or hydrogenolysing agent.

Preferred starting materials for the solvolysis or hydrogenolysis are those which conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' is an amino-protecting group, instead of an HN group, and/or those which carry a hydroxyl-protecting group instead of the H atom of a hydroxyl group, for example those which conform to the formula I, but carry a —COOR" group, in which R" is a hydroxyl-protecting group, instead of a —COOH group.

Preferred starting materials are also the oxadiazole derivatives, which can be converted into the corresponding amidino compounds.

The amidino group can be liberated from its oxadiazole derivative by, for example, treatment with hydrogen in the presence of a catalyst (for example Raney nickel). Suitable solvents are those indicated below, in particular alcohols, such as methanol or ethanol, organic acids, such as acetic acid or propionic acid, or mixtures thereof. The hydrogenolysis is generally carried out at temperatures between about 0 and 100° and pressures between about 1 and 200 bar, preferably at 20-30° (room temperature) and 1-10 bar.

The oxadiazole group is introduced, for example, by reaction of the cyano compounds with hydroxylamine and reaction with phosgene, dialkyl carbonate, chloroformic acid esters, N,N'-carbonyidiimidazole or acetic anhydride.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easily removable after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, O-but and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Protecting groups which can be removed hydrogenolytically (for example CBZ, benzyl or the liberation of the amidino group from its oxadiazole derivative) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

A cyano group is converted into an amidino group by reaction with, for example, hydroxylamine followed by reduction of the N-hydroxyamidine using hydrogen in the presence of a catalyst, such as, for example, Pd/C. In order to prepare an amidine of the formula I, it is also possible to adduct ammonia onto a nitrile. The adduction is preferably carried out in a number of steps by, in a manner known per se, a) converting the nitrile into a thioamide using H$_2$S, converting the thioamide into the corresponding S-alkylimidothioester using an alkylating agent, for example CH$_3$I, and reacting the thioester in turn with NH$_3$ to give the amidine, b) converting the nitrile into the corresponding imidoester using an alcohol, for example ethanol in the presence of HCl, and treating the imidoester with ammonia (Pinner synthesis), or c) reacting the nitrile with lithium bis(trimethylsilyl)amide, and subsequently hydrolysing the product.

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide, or reacted with CH$_3$—C(=NH)—Oet, advantageously in an inert solvent, such as dichloromethane or THF and/or in the presence of a base, such as triethylamine or pyridine, at temperatures between −60 and +30°.

If desired, the starting materials can also be formed in situ so that they are not isolated from the reaction mixture, but instead are immediately converted further into the compounds of the formula I.

Compounds of the formula I in which R$^1$ is in protected form can preferably be obtained by reacting compounds of the formula II with compounds of the formula III.

The reaction is generally carried out in an inert solvent, in the presence of an acid-binding agent, preferably an alkali or alkaline earth metal hydroxide, carbonate or bicarbonate, or in the presence of another salt of a weak acid of the alkali or alkaline earth metals, preferably of potassium, sodium, calcium or caesium. The addition of an organic base, such as triethylamine, dimethylaniline, pyridine or quinoline, may also be favourable. Depending on the conditions used, the reaction time is between a few minutes and 14 days, and the reaction temperature is between about 0° and 150°, normally between 20° and 130°.

Examples of suitable inert solvents are water; hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The starting compounds of the formulae II and III are generally known. If they are novel, however, they can be prepared by methods known per se.

In the compounds of the formula III, L is preferably Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

It is also possible to use physiologically acceptable organic bases, such as, for example, ethanolamine.

Some of the starting compounds are novel. The invention therefore furthermore relates to the intermediates of the formula I-I

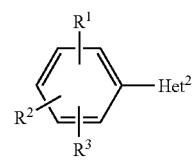

in which
R$^1$ is NO$_2$, CN, NHA, NHCOA, NACF$_3$, NH$_2$ or (CH$_2$)$_n$NH$_2$,
R$^2$ and
R$^3$ are each, independently of one another, H, Hal, A, OA or CF$_3$,
A is alkyl having 1, 2, 3, 4, 5 or 6 carbon atoms,
Het$^2$ is a monocyclic or bicyclic, saturated, unsaturated or aromatic heterocyclic radical having from 1 to 4 N, O and/or S atoms which is unsubstituted or monosubstituted, disubstituted or trisubstituted by Hal, A, OA, CN, COOA, CONH$_2$, NHCOA, NHSO$_2$A, S(O)$_m$A and/or carbonyl oxygen,
n is 0, 1, 2 or 3, and salts thereof.

In the compounds of the formula I-I, A is preferably methyl, ethyl, propyl, isopropyl, butyl or tert-butyl.

Het$^2$ is preferably piperidinyl, pyrrolidinyl, piperazinyl, azepamyl, pyrazinyl, 3,4,5,6-tetrahydropyridinyl, pyridinyl, 2-azabicyclo[2.2.2]octanyl, 1,3-oxazinanyl or oxazolidinyl.

The invention furthermore relates to the intermediates selected from the group consisting of
1-(3-fluoro-4-nitrophenyl)piperidin-2-one,
1-(4-amino-3-fluorophenyl)piperidin-2-one, tert-butyl 4-(4-nitrophenyl)-3-oxopiperazin-1-carboxylate,
tert-butyl 4-(4-aminophenyl)-3-oxopiperazin-1-carboxylate,
1-(4-nitrophenyl)azepam-2-one,
1-(4-aminophenyl)azepam-2-one,
1-(3-fluoro-4-nitrophenyl)azepam-2-one,
1-(4-amino-3-fluorophenyl)azepam-2-one,
1-(2-methyl-4-nitrophenyl)azepam-2-one,
1-(4-amino-2-methylphenyl)azepam-2-one,
1-(4-nitrophenyl)-1H-pyrazin-2-one,
1-(4-aminophenyl)-1H-pyrazin-2-one,
1-(2,5-dimethyl-4-nitrophenyl)piperidin-2-one,
1-(4-amino-2,5-dimethylphenyl)piperidin-2-one,
2,2,2-trifluoro-N-methyl-N-[4-(2-oxopiperidin-1-yl)phenyl]acetamide,
1-(4-methylaminophenyl)piperidin-2-one,
1-(3-methyl-4-nitrophenyl)piperidin-2-one,
1-(4-amino-3-methylphenyl)piperidin-2-one,
5'-nitro-3,4,5,6-tetrahydro-1,2'-bipyridinyl-2-one,
5'-amino-3,4,5,6-tetrahydro-1,2'-bipyridinyl-2-one,
2-(4-nitrophenyl)-2-azabicyclo[2.2.2]octan-3-one,
2-(4-aminophenyl)-2-azabicyclo[2.2.2]octan-3-one,
2-(4-nitro-2-trifluoromethylphenyl)-2-azabicyclo[2.2.2]octan-3-one,
2-(4-amino-2-trifluoromethylphenyl)-2-azabicyclo[2.2.2]octan-3-one,
2-(2-methyl-4-nitrophenyl)-2-azabicyclo[2.2.2]octan-3-one,
2-(4-amino-2-methylphenyl)-2-azabicyclo[2.2.2]octan-3-one,
2-(2-methoxy-4-nitrophenyl)-2-azabicyclo[2.2.2]octan-3-one,
2-(4-amino-2-methoxyphenyl)-2-azabicyclo[2.2.2]octan-3-one,
1-(2-methoxy-4-nitrophenyl)piperidin-2-one,
1-(4-amino-2-methoxyphenyl)piperidin-2-one,
1-(4-nitro-2-trifluoromethylphenyl)piperidin-2-one,
1-(4-amino-2-trifluoromethylphenyl)piperidin-2-one,
3-(2-methyl-4-nitrophenyl)-1,3-oxazinan-2-one,
3-(4-amino-2-methylphenyl)-1,3-oxazinan-2-one,
1-(2-chloro-4-nitrophenyl)pyrrolidin-2-one,
1-(4-amino-2-chlorophenyl)pyrrolidin-2-one,
1-(2-methoxy-4-nitrophenyl)pyrrolidine-2,5-dione,
1-(4-amino-2-methoxyphenyl)pyrrolidine-2,5-dione,
5,5-dimethyl-1-(4-nitrophenyl)pyrrolidin-2-one,
1-(4-aminophenyl)-5,5-dimethylpyrrolidin-2-one,
3-(2-methyl-4-nitrophenyl)oxazolidin-2-one,
3-(4-amino-2-methylphenyl)oxazolidin-2-one,
1-(2-fluoro-4-nitrophenyl)azepam-2-one,
1-(4-amino-2-fluorophenyl)azepam-2-one,
4-(2-oxo-2H-pyridin-1-yl)benzonitrile,
1-(4-aminomethylphenyl)-1H-pyridin-2-one,
1-(4-aminomethylphenyl)piperidin-2-one,
1-(2-ethyl-5-nitrophenyl)pyrrolidin-2-one,
1-(5-amino-2-ethylphenyl)pyrrolidin-2-one,
1-(4-aminophenyl)piperidine-2,6-dione, and salts thereof.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or their physiologically acceptable salts for the preparation of pharmaceutical preparations, in particular by non-chemical methods. They can be converted here into a suitable dosage form together with at least one solid, liquid and/or semi-liquid excipient or assistant and, if desired, in combination with one or more further active ingredients.

The invention furthermore relates to medicaments comprising at least one compound of the formula I and/or its pharmaceutically usable derivatives, solvates and stereoisomers, including mixtures thereof in all ratios, and, if desired, excipients and/or assistants.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatin, carbohydrates, such as lactose or starch, magnesium stearate, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The preparations indicated may be sterilised and/or comprise assistants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

The compounds of the formula I and their physiologically acceptable salts can be used for combating and preventing thromboembolic disorders, such as thrombosis, myocardial infarction, arteriosclerosis, inflammation, apoplexia, angina pectoris, restenosis after angioplasty, claudicatio intermittens, tumours, tumour diseases and/or tumour metastases.

In general, the substances according to the invention are preferably administered in doses between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular illness to which the therapy applies. Oral administration is preferred.

The invention furthermore relates to medicaments comprising at least one compound of the formula I and/or its pharmaceutically usable derivatives, solvates and stereoisomers, including mixtures thereof in all ratios, and at least one further medicament active ingredient.

The invention also relates to a set (kit) consisting of separate packs of (a) an effective amount of a compound of the formula I and/or its pharmaceutically usable derivatives, solvates and stereoisomers, including mixtures thereof in all ratios, and (b) an effective amount of a further medicament active ingredient.

The set comprises suitable containers, such as boxes, individual bottles, bags or ampoules. The set may, for example, comprise separate ampoules each containing an effective amount of a compound of the formula I and/or its pharmaceutically usable derivatives, solvates and stereoisomers, including mixtures thereof in all ratios, and an effective amount of a further medicament active ingredient in dissolved or lyophilised form.

The invention furthermore relates to the use of compounds of the formula I and/or their pharmaceutically usable derivatives, solvates and stereoisomers, including mixtures thereof in all ratios, for the preparation of a medicament for the treatment of thrombosis, myocardial infarction, arteriosclerosis, inflammation, apoplexia, angina pectoris, restenosis after angioplasty, claudicatio intermittens, tumours, tumour diseases and/or tumour metastases, in combination with at least one further medicament active ingredient.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$

EXAMPLE 1

2-(3-amidinophenoxy)-N-(4-morpholin-4-ylphenyl) valeramide is prepared as indicated in the following scheme

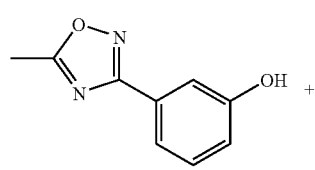

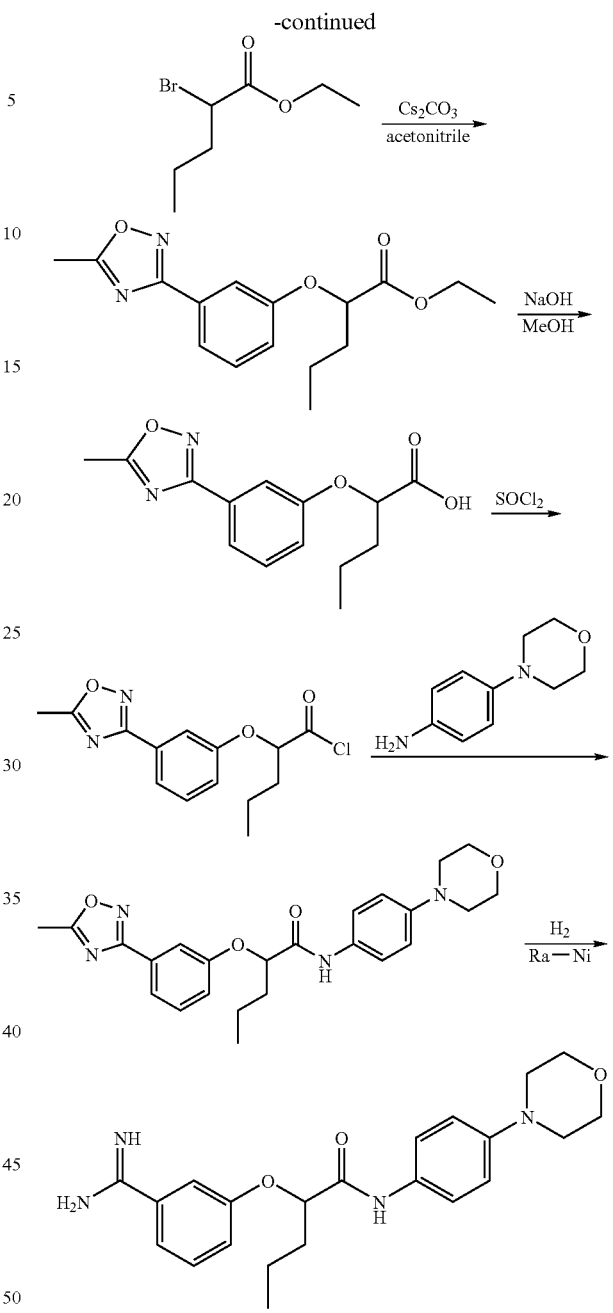

1. 380 g (1.17 mol) of caesium carbonate are added to a solution of 200 g (1.135 mol) of 3-(5-methyl-1,2,4-oxadiazol-3-yl)phenol in 2.5 l of acetonitrile. A solution of 190 ml (1.15 mol) of ethyl 2-bromovalerate in 0.5 l of acetonitrile is subsequently added. The reaction mixture is stirred at room temperature for 24 hours and then filtered, and the filtrate is evaporated, giving ethyl 2-[3-(5-methyl-1,2,4-oxadiazol-3-yl)phenoxy]pentanoate as a yellowish oil; ESI 305.

2. 2.1 l of 1N sodium hydroxide solution are added to a solution of 347 g (1.14 mol) of ethyl 2-[3-(5-methyl-1,2,4-oxadiazol-3-yl)phenoxy]-pentanoate in 1.4 l of methanol, and the mixture is stirred at room temperature for 24 hours. The reaction mixture is diluted with 1 l of water and extracted twice with 1 l of tert-butyl methyl ether each time.

The aqueous phase is acidified to a pH of 2 using concentrated hydrochloric acid and extracted twice with 2 l of tert-butyl methyl ether each time. The combined organic phases are evaporated, and the residue is recrystallised from 100 ml of toluene: 2-[3-(5-methyl-1,2,4-oxadiazol-3-yl)phenoxy]pentanoic acid is obtained as colourless crystals of m.p. 98-100°.

3. 3.50 g (12.7 mmol) of 2-[3-(5-methyl-1,2,4-oxadiazol-3-yl)phenoxy]pentanoic acid are dissolved in 10 ml of thionyl chloride, and the mixture is heated at the boil for 2 hours. The reaction mixture is evaporated, the residue is taken up in toluene, and the solution is reevaporated, giving 2-[3-(5-methyl-1,2,4-oxadiazol-3-yl)phenoxy]-pentanoyl chloride as a yellowish solid.

4. 200 mg of 4-dimethylaminopyridine on polystyrene are added to a solution of 100 mg (0.339 mmol) of 2-[3-(5-methyl-1,2,4-oxadiazol-3-yl)phenoxy]pentanoyl chloride and 60.4 mg (0.339 mmol) of 4-morpholin-4-ylaniline in 6 ml of dichloromethane, and the mixture is stirred at room temperature for 18 hours. The reaction mixture is filtered, and the filtrate is evaporated, giving N-(4-morpholin-4-ylphenyl)-2-[3-(5-methyl-1,2,4-oxadiazol-3-yl)phenoxy]pentanoamide as a colourless solid, ESI 437.

5. 200 mg of water-moist Raney nickel and 0.25 ml of acetic acid are added to a solution of 140 mg (0.321 mmol) of N-(4-morpholin-4-yl-phenyl)-2-[3-(5-methyl-1,2,4-oxadizole-3-yl)phenoxy]pentanoamide in 6 ml of methanol, and the mixture is hydrogenated at room temperature and atmospheric pressure for 18 hours. The reaction mixture is filtered, and the residue is evaporated, giving 2-(3-amidinophenoxy)-N-(4-morpholin-4-ylphenyl)valeramide, acetate, ESI 397; $IC_{50}$ (Xa)=$3\times10^{-7}$ M; $IC_{50}$ (VIIa)=$4.9\times10^{-7}$ M.

The following compound is obtained analogously:

2-(3-amidinophenoxy)-N-(4-morpholin-4-ylphenyl)-2-phenylacetamide, diacetate, ESI 431; $IC_{50}$ (Xa)=$9.0\times10^{-8}$ M; IC50 (VIIa)=$6.0\times10^{-8}$ M.

EXAMPLE 2

2-(3-amidinophenylamino)-N-(4-morpholin-4-ylphenyl)-2-phenylacetamide is prepared as indicated in the following scheme:

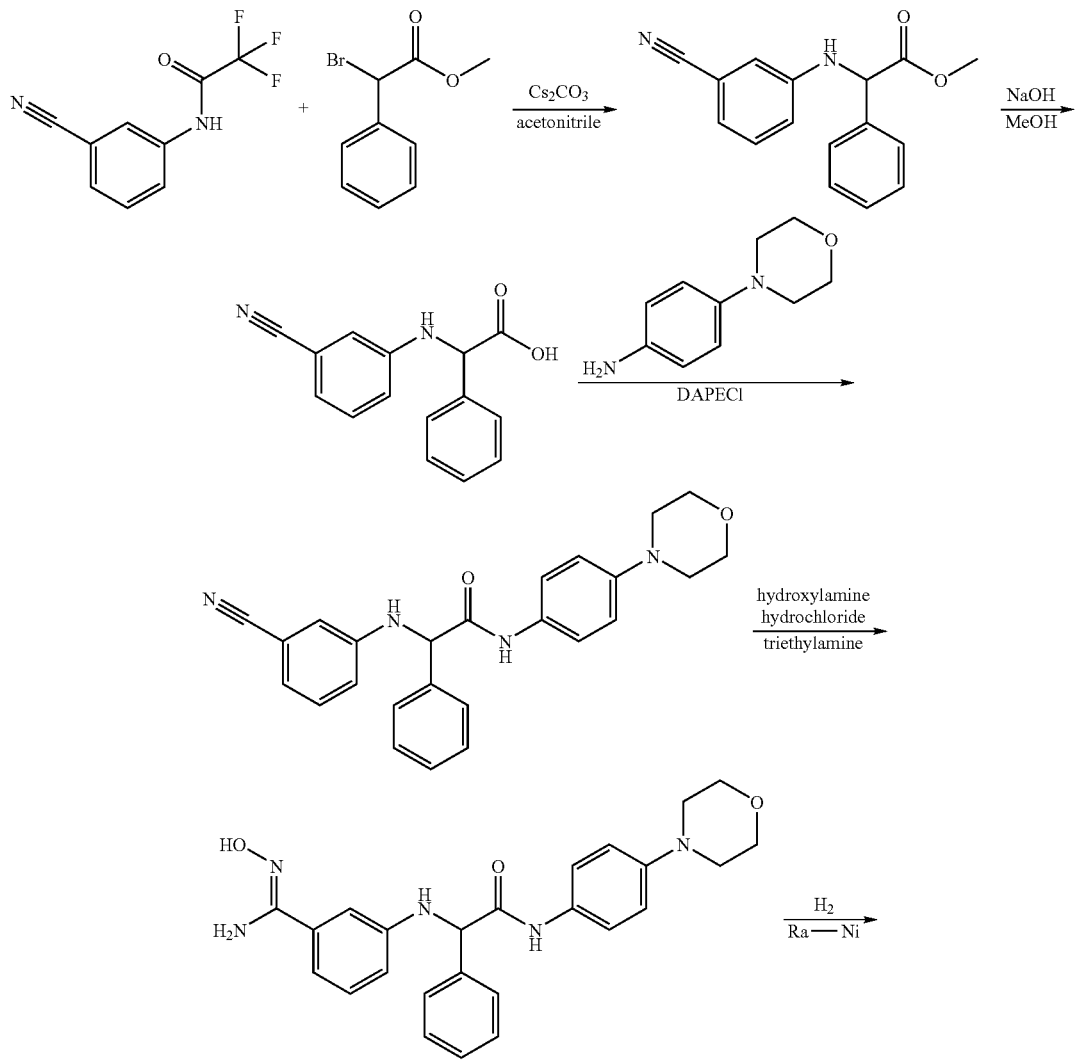

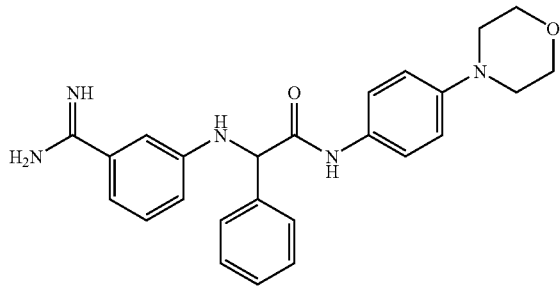

1. 14.3 g (44.0 mmol) of caesium carbonate are added to a solution of 8.6 g (40.2 mmol) of N-(3-cyanophenyl)[2.2.2]trifluoroacetamide in 200 ml of acetonitrile. 7.2 ml (44.4 mmol) of methyl 2-bromo-2-phenylacetate are subsequently added. The reaction mixture is heated at the boil with stirring for 3 hours, then filtered, the filtrate is evaporated, and the residue is chromatographed on a silica-gel column with dichloromethane/petroleum ether, giving methyl (3-cyanophenylamino)-2-phenylacetate as a colourless oil; ESI 267.

2. 50 ml of 1 N sodium hydroxide solution are added to a solution of 9.5 g (35.6 mmol) of methyl (3-cyanophenylamino)-2-phenylacetate in 150 ml of methanol, and the mixture is stirred at room temperature for 21 hours. The reaction mixture is evaporated, the residue is acidified to pH 1 using 25% HCl, and the resultant precipitate is filtered off, giving (3-cyanophenylamino)-2-phenylacetic acid as colourless crystals of m.p. 159-162°.

3. 87 µl (0.793 mmol) of 4-methylmorpholine are added to a solution of 200 mg (0.793 mmol) of (3-cyanophenylamino)-2-phenylacetic acid, 141 mg (0.793 mmol) of 4-morpholin-4-ylaniline, 152 mg (0.793 mmol) of N-(3-dimethylaminopropyl)-N'-ethylcarbodiimide hydrochloride (DAPECI) and 121 mg (0.793 mmol) of hydroxybenzotriazole hydrate (HOBt) in 3 ml of DMF, and the mixture is stirred at room temperature for 48 hours. The reaction mixture is introduced into water, and the precipitate is filtered off, giving 2-(3-cyanophenylamino)-N-(4-morpholin-4-ylphenyl)-2-phenylacetamide as a colourless solid; ESI 413.

4. 149 mg (2.15 mmol) of hydroxylamine hydrochloride, 0.30 ml (2.15 mmol) of triethylamine and a few grains of 0.3 nM molecular sieve are added to a solution of 295 mg (0.715 mmol) of 2-(3-cyanophenylamino)-N-(4-morpholin-4-ylphenyl)-2-phenylacetamide in 5 ml of methanol, and the mixture is heated at 70° C. for 18 hours. The reaction mixture is filtered, the filtrate is evaporated, and the residue is taken up in water. The resultant precipitate is filtered off, giving 2-[3-(N-hydroxyamidino)phenylamino]-N-(4-morpholin-4-ylphenyl)-2-phenylacetamide as a colourless solid; ESI 446.

5. 500 mg of water-moist Raney nickel and 0.1 ml of acetic acid are added to a solution of 150 mg (0.337 mmol) of 2-[3-(N-hydroxyamidino)phenylamino]-N-(4-morpholin-4-ylphenyl)-2-phenylacetamide in 5 ml of methanol, and the mixture is hydrogenated at room temperature and atmospheric pressure for 18 hours. The reaction mixture is filtered, and the residue is evaporated, giving 2-(3-amidinophenylamino)-N-(4-morpholin-4-ylphenyl)-2-phenylacetamide, triacetate, ESI 430; $IC_{50}$ (Xa)=3.4×10$^{-8}$ M; $IC_{50}$ (VIIa)=2.2×10$^{-8}$ M;

The following compound is obtained analogously:

2-(3-amidinophenylamino)-N-(4-dimethylaminophenyl)-4-methylvaleramide, diacetate, ESI 368; $IC_{50}$ (Xa)=1.6×10$^{-7}$ M; $IC_{50}$ (VIIa)=2.1×10$^{-8}$ M.

EXAMPLE 3

2-(3-amidinophenoxy)-N-[4-(2-oxopiperidin-1-yl)phenyl]-2-phenylacetamide is prepared as indicated in the following scheme:

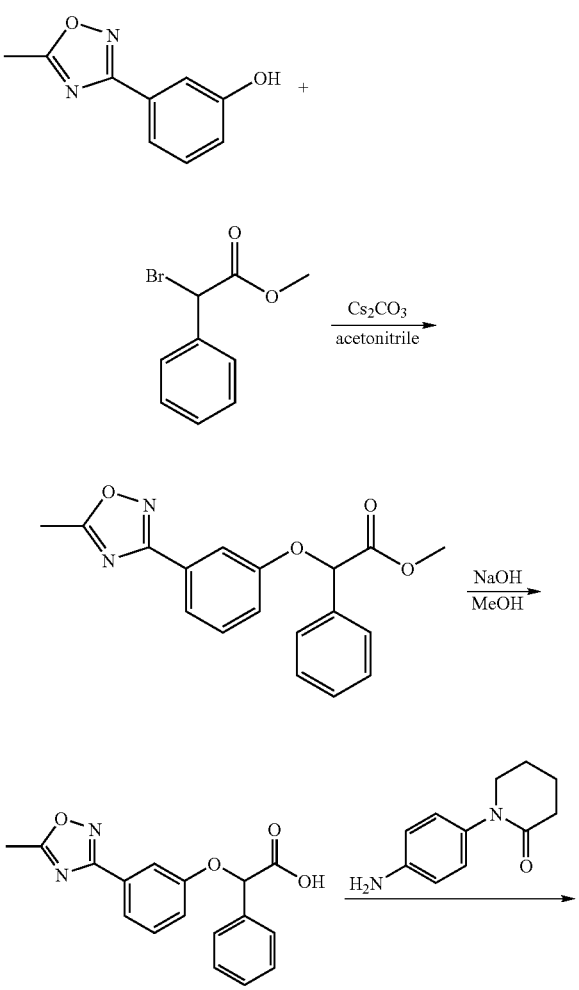

-continued

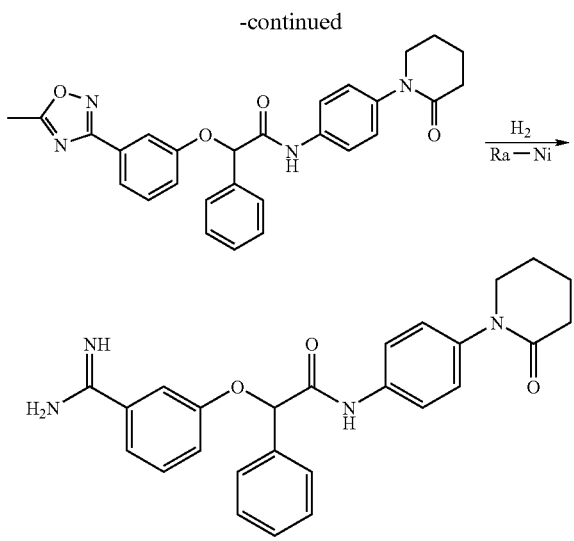

1. 11.5 g (33.5 mmol) of caesium carbonate and 7.67 g (35.2 mmol) of methyl 2-bromo-2-phenylacetate are added to a solution of 5.90 g (33.5 mmol) of 3-(5-methyl-1,2,4-oxadiazol-3-yl)phenol in 50 ml of acetonitrile. The reaction mixture is stirred at room temperature for 24 hours, then filtered, and the filtrate is evaporated, giving methyl [3-(5-methyl-1,2,4-oxadiazol-3-yl)phenoxy]-2-phenylacetate as a yellowish oil; ESI 325.

2. 30 ml of 1N sodium hydroxide solution are added to a solution of 10.1 g (31.0 mmol) of methyl [3-(5-methyl-1,2,4-oxadiazol-3-yl)phenoxy]-2-phenylacetate in 30 ml of methanol, and the mixture is heated at 80° C. for 3 hours. The reaction mixture is evaporated, 1N HCl is added, and the mixture is extracted with ethyl acetate. The organic phase is dried and evaporated, and the residue is recrystallised from ether, giving [3-(5-methyl-1,2,4-oxadiazol-3-yl)phenoxy]-2-phenylacetic acid as colourless crystals; ESI 311.

3. 35 µl (0.322 mmol) of 4-methylmorpholine are added to a solution of 100 mg (0.322 mmol) of [3-(5-methyl-1,2,4-oxadiazol-3-yl)phenoxyl]-2-phenylacetic acid, 61.3 mg (0.322 mmol) of 1-(4-aminophenyl)piperidin-2-one (prepared from 1-(4-nitrophenyl)piperidin-2-one by hydrogenation using Raney nickel as catalyst), 61.7 mg (0.322 mmol) of N-(3-dimethylaminopropyl)-N'-ethylcarbodiimide hydrochloride (DAPECI) and 49.3 mg (0.322 mmol) of hydroxybenzotriazole hydrate (HOBt) in 3 ml of DMF, and the mixture is stirred at room temperature for 48 hours. The reaction mixture is introduced into aqueous sodium carbonate solution, and the precipitate is filtered off, giving 2-[3-(5-methyl-1,2,4-oxadiazol-3-yl)phenoxy]-N-[4-(2-oxopiperidin-1-yl)phenyl]-2-phenylacetamide as a colourless solid; ESI 483.

4. 200 mg of water-moist Raney nickel and 0.2 ml of acetic acid are added to a solution of 122 mg (0.253 mmol) of 2-[3-(5-methyl-1,2,4-oxadiazol-3-yl)phenoxy]-N-[4-(2-oxopiperidin-1-yl)phenyl]-2-phenylacetamide in 5 ml of methanol, and the mixture is hydrogenated at room temperature and atmospheric pressure for 18 hours. The reaction mixture is filtered, and the residue is evaporated, giving 2-(3-amidinophenoxy)-N-[4-(2-oxopiperidin-1-yl)phenyl]-2-phenylacetamide, acetate (EMD 388547), ESI 443; IC$^{50}$ (Xa)=3.2×10$^{-8}$ M; IC$_{50}$(VIIa)=1.4×10$^{-8}$ M.

The following compounds are obtained analogously:
2-(3-amidinophenoxy)-N-[4-(2-oxopyrrolidin-1-yl)phenyl]-2-phenylacetamide, acetate, ESI 429; IC$_{50}$ (Xa)=6.5×10$^{-8}$ M; IC$_{50}$ (VIIa)=3.9×10$^{-8}$ M;
2-(3-amidinophenoxy)-N-[4-(2-oxopiperidin-1-yl)phenyl] valeramide, acetate, ESI 409; IC$_{50}$ (Xa)=7.0×10$^{-8}$ M; IC$_{50}$ (VIIa)=3.3×10$^{-8}$ M;
2-(3-amidinophenoxy)-N-[4-(2-oxopyrrolidin-1-yl)phenyl] valeramide, acetate, ESI 395; IC$_{50}$ (Xa)=1.3×10$^{-7}$ M; IC$_{50}$ (VIIa)=8.3×10$^{-8}$ M;
2-(3-amidinophenoxy)-N-[4-(2-oxo-1H-pyridin-1-yl)phenyl]-2-phenylacetamide,
2-(3-amidinophenoxy)-N-[4-(3-oxomorpholin-4-yl)phenyl]-2-phenylacetamide,
2-(3-amidinophenoxy)-N-[4-(4-oxo-1H-pyridin-1-yl)phenyl]-2-phenylacetamide,
2-(3-(N-Hydroxyamidino)phenoxy)-N-[4-(2-oxopiperidin-1-yl)phenyl]2-phenylacetamide,
2-(3-amidinophenoxy)-N-[4-(2,6-dioxopiperidin-1-yl)phenyl]-2-phenylacetamide,
2-(3-amidinophenoxy)-N-[4-(3-oxo-2H-piperazin-1-yl)phenyl]-2phenylacetamide,
2-(3-amidinophenoxy)-N-[2-fluoro-4-(2-oxo-1 H-pyridin-1-yl)phenyl]-2phenylacetamide,
2-(3-amidinophenoxy)-N-[4-(2 ,5-dioxopyrrolidin-1-yl)phenyl]-2-phenylacetamide,
2-(3-amidinophenoxy)-N-[5-(2-oxopiperidin-1-yl)pyridin-2-yl]-2phenylacetamide,
2-(3-amidinophenoxy)-N-[4-(2-oxo-1,3-oxazolidin-3-yl) phenyl]-2-phenylacetamide,
2-(3-amidinophenoxy)-N-[4-(2-oxo-1H-pyridin-1-yl)benzyl]-2-phenylacetamide,
2-(3-amidinophenoxy)-N-[4-(2-oxopiperidin-1-yl)benzyl]-2-phenylacetamide,
2-(3-amidinophenoxy)-N-[4-(2-oxopiperidin-1-yl)butyl]-2-phenylacetamide,
2-(3-amidinophenoxy)-N-[4-(3-oxo-2H-pyridazin-2-yl)phenyl]-2-phenylacetamide,
2-(3-amidinophenoxy)-N-[2-fluoro-4-(2-oxopiperidin-1-yl) phenyl]-2-phenylacetamide,
2-(3-amidinophenoxy)-N-(4-dimethylaminobenzyl)-2-phenylacetamide, ESI 403;
2-(3-amidinophenoxy)-N-[3-(morpholin-4-yl)propyl]-2-phenylacetamide, ESI 397;
2-(3-amidinophenoxy)-N-[3-(piperidin-1-yl)propyl]-2-phenylacetamide, ESI 381;
2-(3-amidinophenoxy)-N-(4-dimethylaminophenyl)-2-phenylacetamide, ESI 389.

Analogous reaction of [3-(5-methyl-1,2,4-oxadiazol-3-yl) phenylamino]-2-phenylacetic acid and
1-(4-aminophenyl)piperidin-2-one,
2-(morpholin-4-yl)ethylamine,
4-dimethylaminobenzylamine,
3-(morpholin-4-yl)propylamine,
3-(piperidin-1-yl)propylamine, and subsequent hydrogenation gives
2-(3-amidinophenylamino)-N-[4-(2-oxopiperidin-1-yl)phenyl]-2-phenylacetamide,
2-(3-amidinophenylamino)-N-[2-(morpholin-4-yl)ethyl]-2-phenylacetamide,
2-(3-amidinophenylamino)-N-(4-dimethylaminobenzyl)-2-phenylacetamide,
2-(3-amidinophenylamino)-N-[3-(morpholin-4-yl)propyl]-2-phenylacetamide,
2-(3-amidinophenylamino)-N-[3-(piperidin-1-yl)propyl]-2-phenylacetamide.

Analogous reaction of [3-(5-methyl-1,2,4-oxadiazol-3-yl)phenoxy]-2-valeric acid and
2-(morpholin-4-yl)ethylamine,
4-dimethylaminobenzylamine,
3-(morpholin-4-yl)propylamine,
3-(piperidin-1-yl)propylamine, and subsequent hydrogenation gives
2-(3-amidinophenoxy)-N-[2-(morpholin-4-yl)ethyl]valeramide, ESI 349;
2-(3-amidinophenoxy)-N-(4-dimethylaminobenzyl)valeramide, ESI 369;
2-(3-amidinophenoxy)-N-[3-(morpholin-4-yl)propyl]valeramide, ESI 363;
2-(3-amidinophenoxy)-N-[3-(piperidin-1-yl)propyl]valeramide, ESI 347.

EXAMPLE 4

Analogously to Examples 1-3, reaction of (3-cyanophenoxy)-2-phenylacetic acid and
1-(4-aminophenyl)piperidin-2-one,
2-(morpholin-4-yl)ethylamine,
4-dimethylaminobenzylamine,
3-(morpholin-4-yl)propylamine,
3-(piperidin-1-yl)propylamine, followed by hydrolysis using aqueous sodium hydroxide solution gives
2-(3-aminocarbonylphenoxy)-N-[4-(2-oxopiperidin-1-yl)phenyl]-2-phenylacetamide, ESI 444;
2-(3-aminocarbonylphenoxy)-N-[2-(morpholin-4-yl)ethyl]-2-phenylacetamide,
2-(3-aminocarbonylphenoxy)-N-(4-dimethylaminobenzyl)-2-phenylacetamide,
2-(3-aminocarbonylphenoxy)-N-[3-(morpholin-4-yl)propyl]-2-phenylacetamide,
2-(3-aminocarbonylphenoxy)-N-[3-(piperidin-1-yl)propyl]-2-phenylacetamide.

EXAMPLE 5

The following compounds are obtained analogously to Example 1:
2-(3-amidinophenoxy)-N-(4-morpholin-4-ylbenzyl)valeramide, diacetate, ESI 411;
2-(3-amidinophenoxy)-N-(4-morpholin-4-ylbenzyl)-2-phenylacetamide, diacetate, ESI 445;
2-(3-amidinophenoxy)-N-[4-(3-oxomorpholin-4-yl)phenyl]-2-phenylacetamide, acetate, ESI 445;
2-(3-amidinophenoxy)-N-[3-(2-oxopiperidin-1-yl)phenyl]-2-phenylacetamide, acetate, ESI 443;
2-(3-amidinophenoxy)-N-[3-methyl-4-(2-oxopiperidin-1-yl)phenyl]-2-phenylacetamide, acetate, ESI 457;
(2R)-2-(3-amidinophenoxy)-N-[4-(2-oxopiperidin-1-yl)phenyl]valeramide, acetate, ESI 409;
2-(3-amidinophenoxy)-N-[2-fluoro-4-(2-oxopiperidin-1-yl)phenyl]-2-phenylacetamide, acetate, ESI 461;
2-(3-amidinophenoxy)-N-[2-fluoro-4-(2-caprolactam-1-yl)phenyl]-2-phenylacetamide, acetate, ESI 475;
2-(3-amidinophenoxy)-N-[3-methyl-4-(2-caprolactam-1-yl)phenyl]valeramide, acetate, ESI 437;
2-(3-amidinophenoxy)-N-[3-methyl-4-(2-oxopiperidin-1-yl)phenyl]valeramide, acetate, ESI 423;
2-(3-amidinophenoxy)-N-[3-fluoro-4-(2-oxopiperidin-1-yl)phenyl]valeramide, acetate, ESI 427;
2-(3-amidinophenoxy)-N-[4-(2-oxopiperidin-1-yl)phenyl]acetamide, acetate, ESI 367;
2-(2-amidinophenoxy)-N-[4-(2-oxopiperidin-1-yl)phenyl]-2-phenylacetamide, acetate, ESI 443;
2-(4-amidinophenoxy)-N-[4-(2-oxopiperidin-1-yl)phenyl]-2-phenylacetamide, acetate, ESI 443;
3-(3-amidinophenyl)-N-[4-(2-oxopiperidin-1-yl)phenyl]propionamide, ESI 365;
2-(3-amidinophenoxy)-N-[3-fluoro-4-(2-oxopiperidin-1-yl)phenyl]-2-phenylacetamide, ESI 461;
3-(3-amidinophenyl)-N-[3-methyl-4-(2-oxopiperidin-1-yl)phenyl]propionamide, ESI 379;
(2S)-2-(3-amidinophenoxy)-N-[3-fluoro-4-(2-oxopiperidin-1-yl)phenyl]valeramide, acetate, ESI 427;
2-(3-amidinophenoxy)-N-[3-methyl-4-(2-caprolactam-1-yl)phenyl]-2-phenylacetamide, acetate, ESI 471;
2-(3-amidinophenylmethyl)-N-[4-(2-oxopiperidin-1-yl)phenyl]valeramide, acetate, ESI 407;
2-(3-amidinophenylmethyl)-N-[3-methyl-4-(2-oxopiperidin-1-yl)phenyl]valeramide, acetate, ESI 421;
2-(3-amidinophenoxy)-N-[4-(2-oxopiperazin-1-yl)phenyl]valeramide, diacetate, ESI 410;
(2S)-2-(3-amidinophenoxy)-N-[4-(2-caprolactam-1-yl)phenyl]valeramide, acetate, ESI 423;
(2S)-2-(3-amidinophenoxy)-N-[3-methyl-4-(2-oxopiperidin-1-yl)phenyl]valeramide, acetate, ESI 423;
2-(3-amidinophenoxy)-N-[3-methyl-4-(2-oxopiperidin-1-yl)phenyl]-4-methylvaleramide, acetate, ESI 437;
2-(3-amidinophenoxy)-N-[4-(2-oxopiperidin-1-yl)phenyl]-4-methylvaleramide, acetate, ESI 423;
(2R)-2-(3-amidinophenoxy)-N-[4-(2-oxopiperidin-1-yl)phenyl]valeramide, acetate, ESI 409;
2-(3-amidinophenoxy)-N-[4-(2-oxopiperidin-1-yl)phenyl]propionamide, acetate, ESI 381;
2-(3-amidinophenoxy)-N-[3-methyl-4-(2-oxopiperidin-1-yl)phenyl]propionamide, acetate, ESI 395;
2-(3-amidinophenoxy)-N-[4-(2-oxopiperidin-1-yl)phenyl]butyramide, acetate, ESI 395;
2-(3-amidinophenoxy)-N-[3-methyl-4-(2-oxopiperidin-1-yl)phenyl]butyramide, acetate, ESI 409;
(2S)-2-(3-amidinophenoxy)-N-[3-methyl-4-(2-caprolactam-1-yl)phenyl]valeramide, acetate, ESI 437;
2-(3-amidinophenoxy)-N-[4-(2-oxopyridin-1-yl)phenyl]valeramide, acetate, ESI 405;
2-(3-amidinophenoxy)-N-[2,5-dimethyl-4-(2-oxopiperidin-1-yl)phenyl]valeramide, acetate, ESI 437;
2-(3-amidinophenoxy)-N-[3-methyl-4-(2-oxopyrrolidin-1-yl)phenyl]-2-phenylacetamide, acetate, ESI 443;
2-(3-amidinophenoxy)-N-[3-methyl-4-(2-oxopyrrolidin-1-yl)phenyl]valeramide, acetate, ESI 409;
2-(3-amidinophenoxy)-N-[2-methyl-4-(2-oxopiperidin-1-yl)phenyl]valeramide, acetate, ESI 423;
2-(3-amidinophenoxy)-N-(2-oxo-3,4,5,6-tetrahydro-2H-1,2'-bipyridinyl-5'-yl)valeramide, diacetate, ESI 410

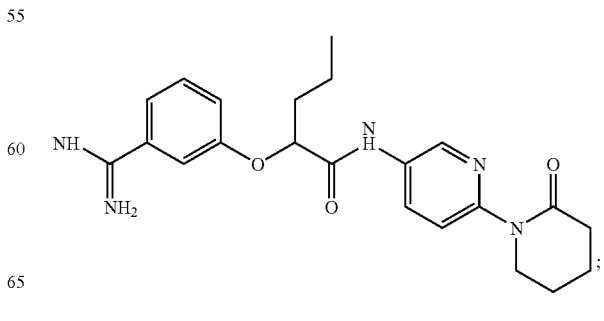

2-(3-amidinophenoxy)-N-[2-methyl-4-(2-oxopiperidin-1-yl)phenyl]-2-phenylacetamide, acetate, ESI 457;

2-(3-amidinophenoxy)-N-(2-oxo-3,4,5,6-tetrahydro-2H-1,2'-bipyridinyl-5'-yl)-2-phenylacetamide, diacetate, ESI 444;

2-[(3-N-methoxycarbonylamidino)phenoxy]-N-[4-(2-oxopiperidin-1-yl)phenyl]valeramide, ESI 467;

2-(3-amidinophenoxy)-N-[3-fluoro-4-(2-oxopyrrolidin-1-yl)phenyl]valeramide, acetate, ESI 413;

2-(3-amidinophenoxy)-N-[3-fluoro-4-(2-oxopyrrolidin-1-yl)phenyl]-2-phenylacetamide, acetate, ESI 447;

2-(3-amidinophenoxy)-N-[4-(2-oxopiperidin-1-yl)phenyl]caproamide, acetate, ESI 423;

2-(3-amidinophenoxy)-N-[4-(2-oxopyrrolidin-1-yl)phenyl]butyramide, acetate, ESI 381;

2-(3-amidinophenoxy)-N-[4-(2-oxopiperidin-1-yl)phenyl]-3-methylbutyramide, acetate, ESI 409;

2-(3-amidinophenoxy)-N-[4-ethyl-3-(2-oxopyrrolidin-1-yl)phenyl]valeramide, acetate, ESI 423;

2-(3-amidinophenoxy)-N-[3-fluoro-4-(2-caprolactam-1-yl)phenyl]valeramide, acetate, ESI 441;

2-(3-amidinophenoxy)-N-[3-fluoro-4-(2-caprolactam-1-yl)phenyl]-2-phenylacetamide, acetate, ESI 475;

2-(3-amidinophenoxy)-N-[4-(2,6-dioxopiperidin-1-yl)phenyl]valeramide, ESI 423;

3-(3-amidinophenyl)-N-[4-(2-oxopiperidin-1-yl)phenyl]-2-phenylpropionamide, acetate, ESI 441;

3-(3-amidinophenyl)-N-[3-methyl-4-(2-oxopiperidin-1-yl)phenyl]-2-phenylpropionamide, acetate, ESI 455;

2-(3-amidinophenoxy)-N-[3-methoxy-4-(2,5-dioxopyrrolidin-1-yl)phenyl]valeramide, acetate, ESI 439;

2-[3-(5-methyl-1,2,4-oxadiazol-3-yl)phenoxy]-N-[4-(2,6-dioxopiperidin-1-yl)phenyl]-2-phenylacetamide, ESI 497;

2-(3-amidinophenoxy)-N-[4-(2,6-dioxopiperidin-1-yl)phenyl]-2-phenylacetamide, ESI 457;

2-(3-amidinophenoxy)-N-[3-trifluoromethyl-4-(2,6-dioxopiperidin-1-yl)phenyl]valeramide, ESI 491;

2-(3-amidinophenoxy)-N-[3-chloro-4-(2,5-dioxopyrrolidin-1-yl)phenyl]valeramide, acetate, ESI 443;

2-[3-(5-methyl-1,2,4-oxadiazol-3-yl)phenoxy]-N-[3-trifluoromethyl-4-(2,5-dioxopyrrolidin-1-yl)phenyl]-2-valeramide, ESI 517;

2-[3-(5-methyl-1,2,4-oxadiazol-3-yl)phenoxy]-N-[3-chloro-4-(2,5-dioxopyrrolidin-1-yl)phenyl]-2-valeramide, ESI 483;

2-[3-(5-methyl-1,2,4-oxadiazol-3-yl)phenoxy]-N-[3-methoxy-4-(2,5-dioxopyrrolidin-1-yl)phenyl]-2-valeramide, ESI 479;

2-[3-(5-methyl-1,2,4-oxadiazol-3-yl)phenoxy]-N-[4-(2,5-dioxopyrrolidin-1-yl)phenyl]-2-valeramide, ESI 449;

3-(3-amidinophenoxy)-N-[3-chloro-4-(2-oxopiperidin-1-yl)phenyl]-2-phenylacetamide, acetate, ESI 477;

3-(3-amidinophenoxy)-N-[3-chloro-4-(2-oxopiperidin-1-yl)phenyl]valeramide, acetate, ESI 443;

3-(3-amidinophenoxy)-N-[3-chloro-4-(2-oxopiperidin-1-yl)phenyl]butyramide, acetate, ESI 429.

EXAMPLE 5a

1-{4-[2-(3-Amidinophenoxy)pentylamino]phenyl}piperidin-2-one, diacetate, ESI 395, is prepared in accordance with the following scheme

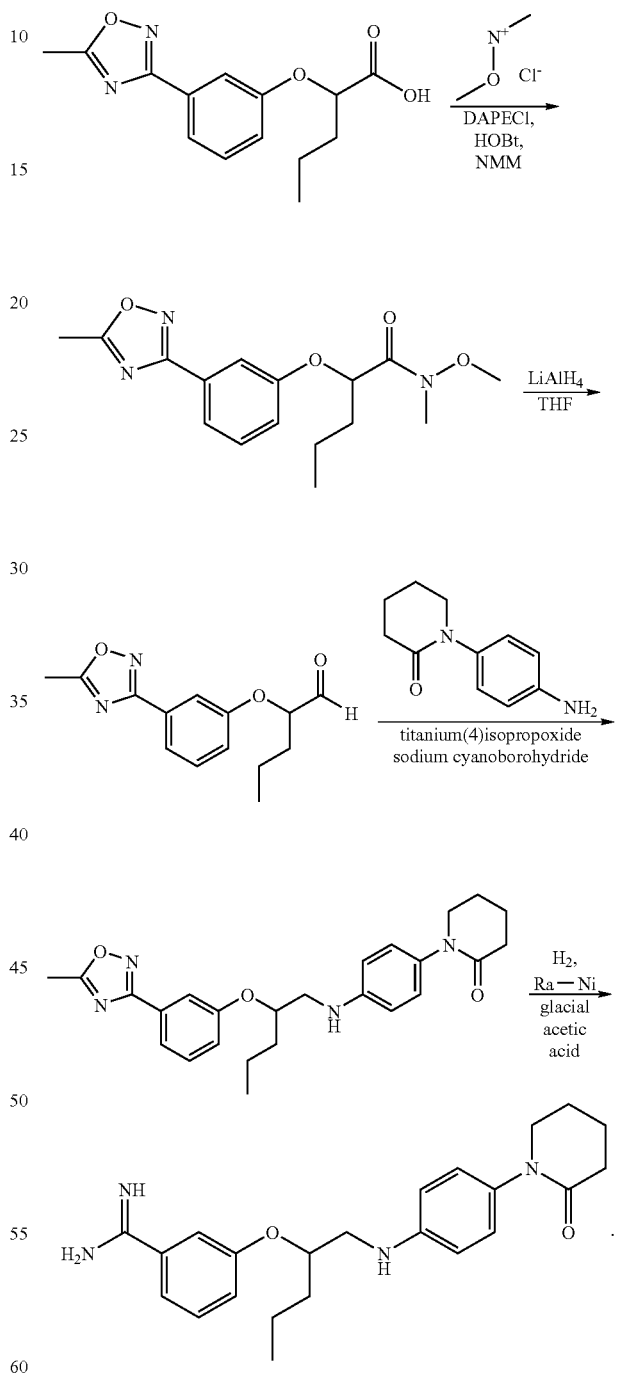

The following compounds are obtained analogously:

1-{4-[2-(3-amidinophenoxy)pentylamino]-2-methylphenyl}piperidin-2-one, diacetate, ESI 409;

1-{4-[2-(3-amidinophenoxy)-2-phenylethoxy]phenyl}piperidin-2-one, acetate, ESI 430.

EXAMPLE 5b 2-(3-Amidinophenoxy)-N-[3-(2-oxopiperidin-1-yl)propyl]-2-phenylacetamide, acetate, ESI 409, is prepared in accordance with the following scheme

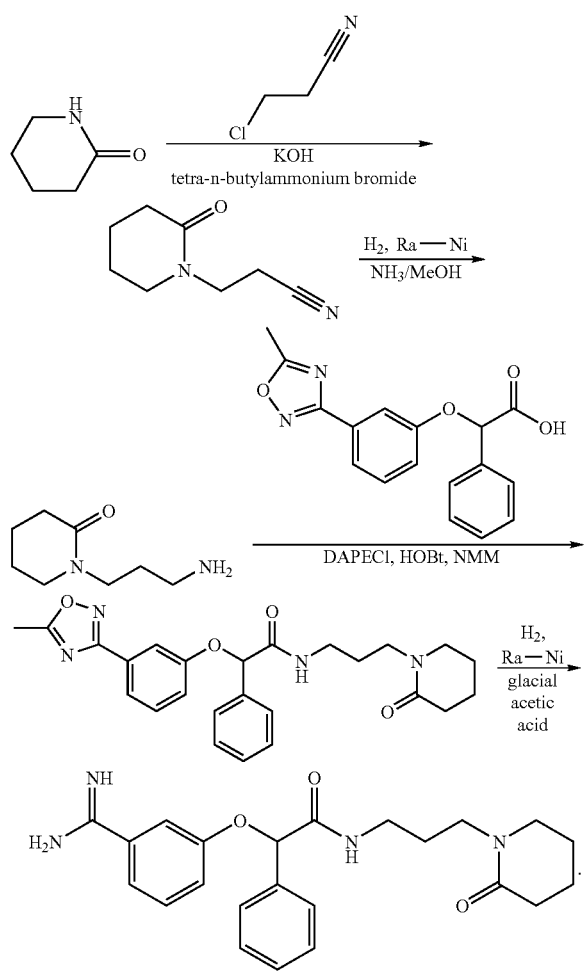

EXAMPLE 5c

2-[(3-N-Ethoxycarbonylamidino)phenoxy]-N-[4-(2-oxopiperidin-1-yl)phenyl]valeramide, ESI 481, is prepared in accordance with the following scheme

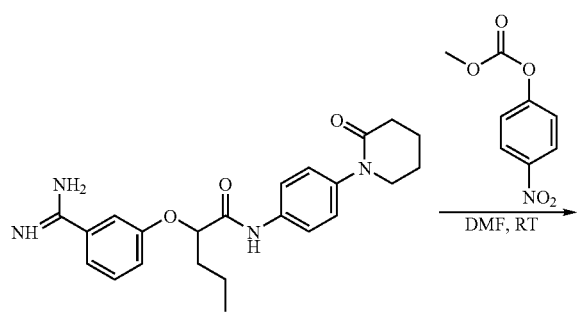

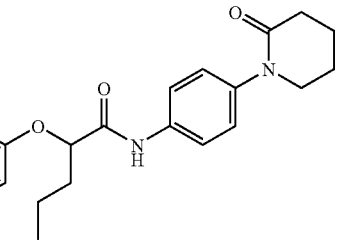

The following compounds are obtained analogously:
2-[(3-N-methoxycarbonylamidino)phenoxy]-N-[4-(2-oxopiperidin-1-yl)phenyl]-2-phenylacetamide, ESI 501;
2-[(3-N-ethoxycarbonylamidino)phenoxy]-N-[4-(2-oxopiperidin-1-yl)phenyl]-2-phenylacetamide, ESI 515.

EXAMPLE 6

The following compounds are obtained analogously to Example 2:
2-(3-amidinophenylamino)-N-[4-(2-oxopiperidin-1-yl)phenyl]-4-methylvaleramide, diacetate, ESI 422;
2-(3-amidinophenylamino)-N-[4-(2-oxopiperidin-1-yl)phenyl]-2-phenylacetamide, diacetate, ESI 442;
2-(3-amidinophenylamino)-N-[4-(2-oxopyrrolidin-1-yl)phenyl]-4-methylvaleramide, diacetate, ESI 408;
2-(3-amidinophenylamino)-N-[4-(2-oxopyrrolidin-1-yl)phenyl]-2-phenylacetamide, diacetate, ESI 428;
2-(3-amidinophenylamino)-N-[4-(2-oxopiperidin-1-yl)phenyl]-2-(2-fluorophenyl)acetamide, acetate, ESI 460;
2-(3-amidinophenylamino)-N-[4-(2-oxopiperidin-1-yl)phenyl]acetamide, acetate, ESI 366;
(2S)-2-(3-amidinophenylamino]-N-[4-(2-caprolactam-1-yl)phenyl]-2-phenylacetamide, acetate, ESI 456;
(2S)-2-(3-amidinophenylamino)-N-[3-methyl-4-(2-oxopiperidin-1-yl)phenyl]-2-phenylacetamide, acetate, ESI 456;
(2S)-2-(3-amidinophenylamino)-N-[4-(2-oxopiperidin-1-yl)phenyl]-2-phenylacetamide, diacetate, ESI 442;
2-(3-amidinophenylamino)-N-[4-(2-oxopiperidin-1-yl)phenyl]caproamide, acetate, ESI 422;
2-(3-amidinophenylamino)-N-[3-methyl-4-(2-oxopiperidin-1-yl)phenyl]-2-(2-fluorophenyl)acetamide, diacetate, ESI 474;
(2S)-2-(2-amidinophenylamino)-N-[4-(2-oxopiperidin-1-yl)phenyl]-2-phenylacetamide, acetate, ESI 442;
(2R)-2-(2-amidinophenylamino)-N-[4-(2-oxopiperidin-1-yl)phenyl]-2-phenylacetamide, acetate, ESI 442;
(2S)-2-(3-amidinophenylamino)-N-[3-fluoro-4-(2-oxopiperidin-1-yl)phenyl]-2-phenylacetamide, ESI 460;
2-(3-amidinophenylamino)-N-[4-(2-oxopiperidin-1-yl)phenyl]-2-(3-fluorophenyl)acetamide, acetate, ESI 460;
2-(3-amidinophenylamino)-N-[3-fluoro-4-(2-oxopiperidin-1-yl)phenyl]-2-(3-fluorophenyl)acetamide, acetate, ESI 478;
(2R)-2-(3-amidinophenylamino)-N-[3-methyl-4-(2-oxopiperidin-1-yl)phenyl]-4-methylvaleramide, ESI 436;
2-(3-amidinophenylamino)-N-[4-(2-oxopiperidin-1-yl)phenyl]valeramide, diacetate, ESI 408;
(2R)-2-(3-amidinophenylamino)-N-[4-(2-oxopiperidin-1-yl)phenyl]-4-methylvaleramide, acetate, ESI 422;
(2R)-2-(3-amidinophenylamino)-N-[4-(2-caprolactam-1-yl)phenyl]-4-methylvaleramide, acetate, ESI 436;

2-(3-amidinophenylamino)-N-[3-fluoro-4-(2-oxopiperidin-1-yl)phenyl]-2-(2-fluorophenyl)acetamide, acetate, ESI 478;

2-(3-amidinophenylamino)-N-[3-methyl-4-(2-caprolactam-1-yl)phenyl]-2-(2-fluorophenyl)acetamide, acetate, ESI 488;

(2R)-2-(3-amidinophenylamino)-N-[3-fluoro-4-(2-oxopiperidin-1-yl)phenyl]-4-methylvaleramide, ESI 440;

2-(3-amidinophenylamino)-N-[4-(2-oxopiperidin-1-yl)phenyl]-4-trifluoro-3-methylbutyramide, acetate, ESI 462;

(2S)-2-(3-amidinophenylamino)-N-[4-(2-oxopiperidin-1-yl)benzyl]-2-phenylacetamide, acetate, ESI 456;

(2S)-2-(3-amidinophenylamino)-N-[4-(3-oxo-2-azabicyclo[2.2.2]oct-2-yl)phenyl]-2-phenylacetamide, acetate, ESI 468;

2-(3-amidinophenylamino)-N-[3-trifluoromethyl-4-(3-oxo-2-azabicyclo-[2.2.2]oct-2-yl)phenyl]2-phenylacetamide, ESI 536;

2-(3-amidino-4-fluorophenylamino)-N-[4-(2-oxopiperidin-1-yl)phenyl]-2-phenylacetamide, diacetate, ESI 460;

EXAMPLE 6a 2-(3-Amidinophenylamino)-N-methyl-N-[4-(2-oxopiperidin-1-yl)phenyl]-2-phenylacetamide, acetate, ESI 456, is prepared in accordance with the following scheme

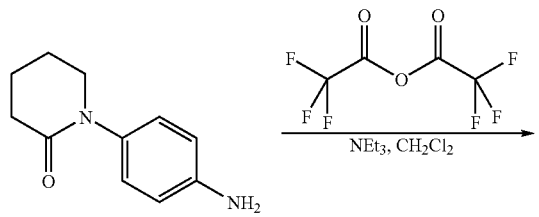

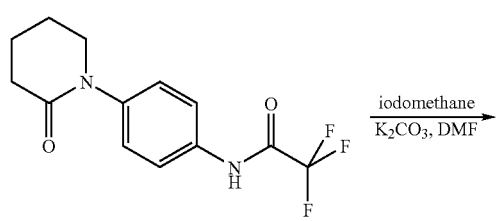

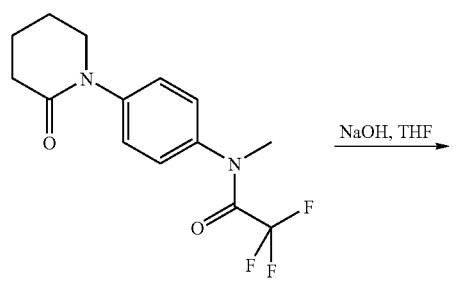

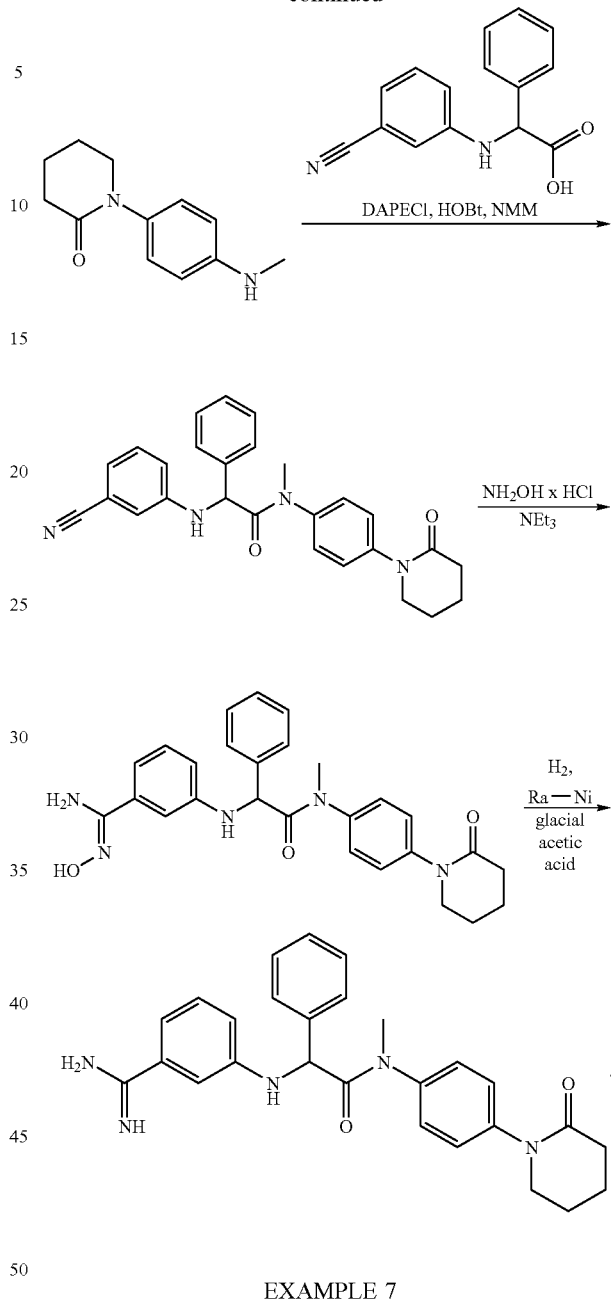

EXAMPLE 7

The following are obtained analogously to Example 4:
2-(3-aminocarbonylphenoxy)-N-[4-(2-oxopiperidin-1-yl)phenyl]valeramide, ESI 410;

2-(3-aminocarbonylphenylamino)-N-[4-(2-oxopiperidin-1-yl)phenyl]-2-phenylacetamide, ESI 443;

2-(3-aminocarbonylphenoxy)-N-[4-(2-oxo-1H-pyridin-1-yl)benzyl]-2-phenylacetamide, ESI 454;

2-(3-aminocarbonylphenoxy)-N-[4-(2-caprolactam-1-yl)phenyl]-2-phenylacetamide, ESI 457;

2-(3-aminocarbonylphenoxy)-N-[4-(2-caprolactam-1-yl)phenyl]-2-phenylacetamide, ESI 458;

2-(3-aminocarbonylphenylamino)-N-[4-(2-oxopiperidin-1-yl)phenyl]-2-(2-fluorophenyl)acetamide, ESI 461;

3-(3-aminocarbonylphenyl)-N-[4-(2-oxopiperidin-1-yl)phenyl]propionamide, ESI 366;

2-(3-aminocarbonylphenoxy)-N-[4-(2-oxo-1H-pyridin-1-yl)phenyl]-2-phenylacetamide, ESI 440;
2-(3-aminocarbonylphenoxy)-N-[3-methyl-4-(2-oxopiperidin-1-yl)phenyl]-2-phenylacetamide, ESI 458;
2-(3-aminocarbonylphenoxy)-N-[4-(4-oxo-4H-pyridin-1-yl)phenyl]-2-phenylacetamide, ESI 458;
2-(3-aminocarbonylphenylamino)-N-[4-(2-oxopiperidin-1-yl)phenyl]-acetamide, ESI 367;
(2S)-2-(3-aminocarbonylphenylamino)-N-[3-methyl-4-(2-oxopiperidin-1-yl)phenyl]-2-phenylacetamide, ESI 457;
(2S)-2-(3-aminocarbonylphenylamino)-N-[4-(2-caprolactam-1-yl)phenyl]-2-phenylacetamide, ESI 457;
(2R)-2-(3-aminocarbonylphenylamino)-N-[4-(2-oxopiperidin-1-yl)phenyl]-2-phenylacetamide, ESI 443;
(2S)-2-(3-aminocarbonylphenylamino)-N-[4-(2-oxopiperidin-1-yl)phenyl]-2-phenylacetamide, ESI 443;
2-(3-aminocarbonylphenylamino)-N-[4-(2-caprolactam-1-yl)phenyl]-2-(2-fluorophenyl)acetamide, ESI 475;
2-(3-aminocarbonylphenylamino)-N-[4-(2-oxopiperidin-1-yl)phenyl]-2-(2-thienyl)acetamide, ESI 449;
2-(4-aminocarbonylphenoxy)-N-[4-(2-oxopiperidin-1-yl)phenyl]-2-phenylacetamide, ESI 444;
2-(2-aminocarbonylphenoxy)-N-[4-(2-oxopiperidin-1-yl)phenyl]-2-phenylacetamide, ESI 444;
2-(3-aminocarbonylphenoxy)-N-[2-fluoro-4-(2-oxopiperidin-1-yl)phenyl]-2-phenylacetamide, ESI 462;
2-(3-aminocarbonylphenoxy)-N-[2-fluoro-4-(2-caprolactam-1-yl)phenyl]-2-phenylacetamide, ESI 475;
(2S)-2-(2-aminocarbonylphenyl)-N-[4-(2-oxopiperidin-1-yl)phenyl]-2-phenylacetamide, ESI 443;
(2R)-2-(2-aminocarbonylphenyl)-N-[4-(2-oxopiperidin-1-yl)phenyl]-2-phenylacetamide, ESI 443;
2-(3-aminocarbonylphenoxy)-N-[3-methyl-4-(2-caprolactam-1-yl)phenyl]-2-phenylacetamide, ESI 472;
(2S)-2-(3-aminocarbonylphenylamino)-N-[4-(2-oxopyridin-1-yl)phenyl]-2-phenylacetamide, ESI 439;
2-(3-aminocarbonylphenylamino)-N-[4-(2-oxopiperidin-1-yl)phenyl]valeramide, ESI 409;
2-(3-aminocarbonyl-4-fluorophenylamino)-N-[4-(2-oxopiperidin-1-yl)phenyl]-2-phenylacetamide, ESI 461;
2-(3-aminocarbonylphenylamino)-N-[3-trifluoromethyl-4-(3-oxo-2-azabicyclo[2.2.2]oct-2-yl)phenyl]-2-phenylacetamide, ESI 537.

EXAMPLE 7a 2-(3-N,N-Diethylaminocarbonylphenoxy)-N-[4-(2-oxopiperidin-1-yl)phenyl]-2-phenylacetamide, ESI 500, is prepared in accordance with the following scheme

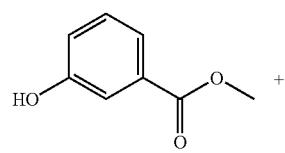

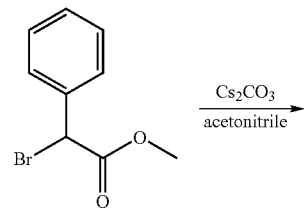

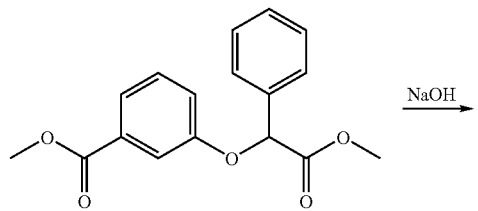

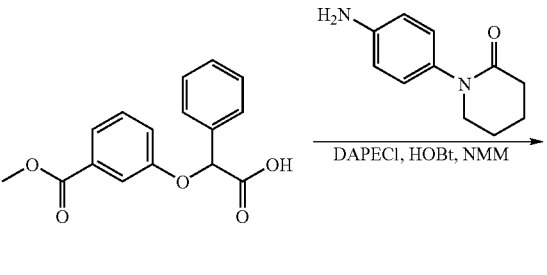

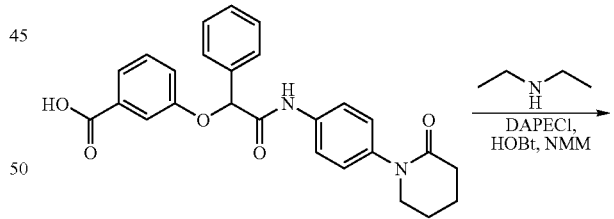

EXAMPLE 7b 2-(3-Aminocarbonylphenoxy)-N-[4-(2-oxopiperazin-1-yl)phenyl]-2-phenylacetamide, ESI 445, is prepared in accordance with the following scheme 2-[3-(N-hydroxyamidino)phenoxy]-N-[4-(2-oxopiperidin-1-yl)phenyl]-2-phenylacetamide, ESI 459;
2-[3-(N-hydroxyamidino)phenyl]-N-[4-(2-oxopiperidin-1-yl)phenyl]propionamide, ESI 381;
2-[3-(N-hydroxyamidino)phenylamino]-N-[4-(2-oxopiperidin-1-yl)phenyl]acetamide, ESI 382;

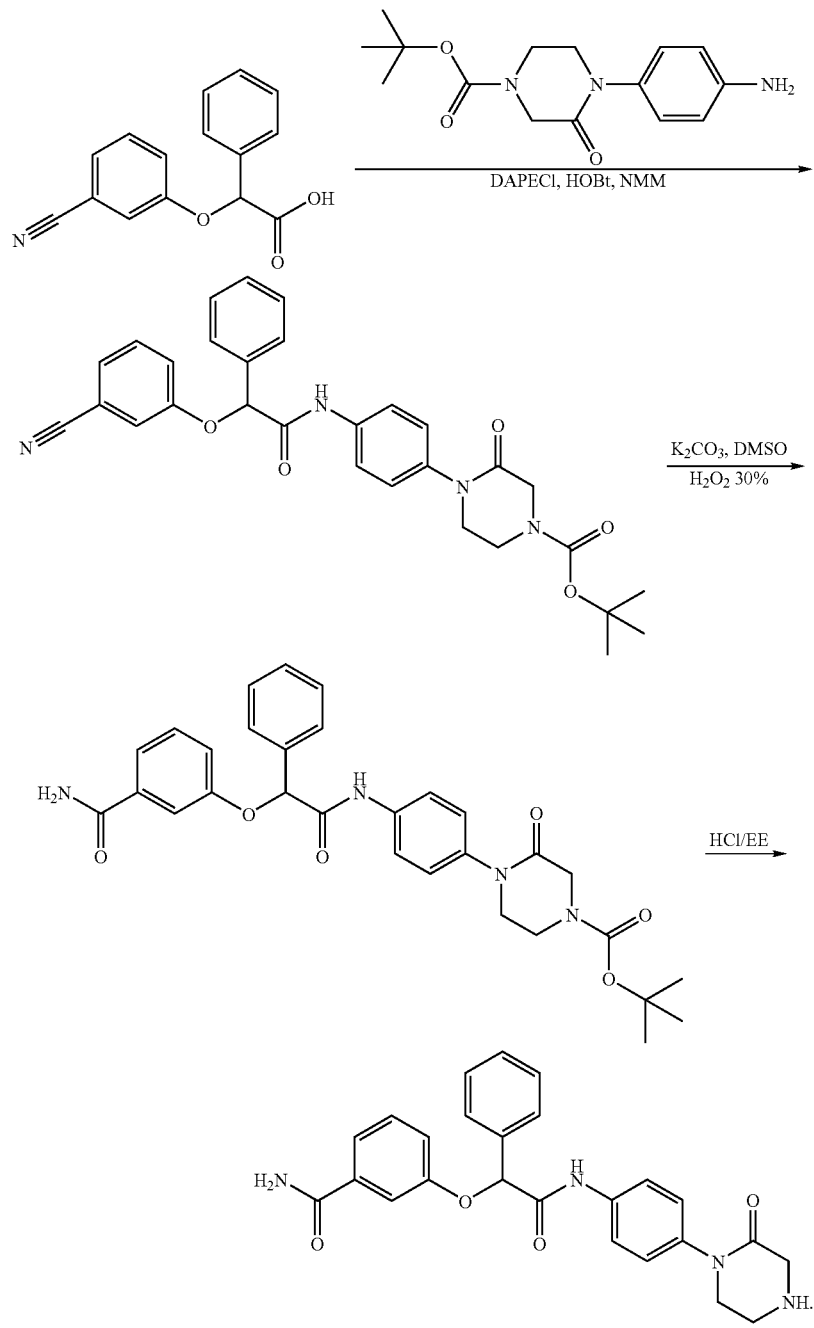

EXAMPLE 8

The following compounds are obtained analogously to Example 2:
2-[3-(N-hydroxyamidino)phenylamino]-N-[4-(2-oxopiperidin-1-yl)phenyl]-2-phenylacetamide, ESI 458;

2-[3-(N-hydroxyamidino)phenoxy]-N-[4-(2-oxopiperidin-1-yl)phenyl]valeramide, ESI 425;

(2R)-[2-(3-(N-hydroxyamidino)phenylamino]-N-[4-(2-caprolactam-1-yl)phenyl]-2-phenylacetamide, ESI 472;

2-[3-(N-hydroxyamidino)phenylamino]-N-[4-(2-oxopiperidin-1-yl)phenyl]-2-(2-trifluoromethylphenyl)acetamide, ESI 526;

2-[3-(N-hydroxyamidino)phenylamino]-N-[3-methyl-4-(2-oxopiperidin-1-yl)phenyl]-2-(2-fluorophenyl)acetamide, ESI 490;

2-[3-(N-hydroxyamidino)phenylamino]-N-[4-(2-oxopiperidin-1-yl)phenyl]-2-(2-thienyl)acetamide, ESI 464;

2-[3-(N-hydroxyamidino)phenoxy]-N-[3-methyl-4-(2-oxopiperidin-1-yl)phenyl]valeramide, ESI 439;

(2S)-2-[3-(N-hydroxyamidino)phenylamino]-N-[3-fluoro-4-(2-oxopiperidin-1-yl)phenyl]-2-phenylacetamide, ESI 476;

3-[3-(N-hydroxyamidino)phenyl]-N-[3-methyl-4-(2-oxopiperidin-1-yl)phenyl]propionamide, ESI 395;

(2S)-2-[3-(N-hydroxyamidino)phenylamino]-N-[4-(2-oxopiperidin-1-yl)phenyl]-4-methylvaleramide, ESI 438;

2-[3-(N-hydroxyamidino)phenoxy]-N-[4-(2-oxopiperidin-1-yl)phenyl]valeramide, ESI 439;

2-[3-(N-hydroxyamidino)phenoxy]-N-[4-(2-oxo-1H-pyrazin-1-yl)phenyl]valeramide, ESI 422;

(2S)-2-[3-(N-hydroxyamidino)phenylamino]-N-[4-(2-oxopiperidin-1-yl)phenyl]-2-phenylacetamide, hydrochloride, ESI 458;

(2R)-2-[3-(N-hydroxyamidino)phenylamino]-N-[4-(2-oxopiperidin-1-yl)phenyl]-4-methylvaleramide, ESI 439;

2-[3-(N-hydroxyamidino)phenylamino]-N-[4-(2-oxopiperidin-1-yl)phenyl]valeramide, ESI 424;

2-[3-(N-hydroxyamidino)phenylamino]-N-[3-methyl-4-(2-oxopiperidin-1-yl)phenyl]-4-methylvaleramide, ESI 452;

2-[3-(N-hydroxyamidino)phenoxy]-N-[4-(2-oxopyridin-1-yl)phenyl]valeramide, ESI 421;

(2R)-2-[3-(N-hydroxyamidino)phenylamino]-N-[4-(2-caprolactam-1-yl)phenyl]-4-methylvaleramide, ESI 452;

(2R)-2-[3-(N-hydroxyamidino)phenoxy]-N-[4-(2-oxopiperidin-1-yl)phenyl]valeramide, ESI 425;

(2S)2-[3-(N-hydroxyamidino)phenoxy]-N-[4-(2-oxopiperidin-1-yl)phenyl]valeramide, ESI 425;

2-[3-(N-hydroxyamidino)phenoxy]-N-[4-(2-oxopiperidin-1-yl)phenyl]-4-methylvaleramide, ESI 439;

2-[3-(N-hydroxyamidino)phenylamino]-N-[4-(2-oxopiperidin-1-yl)phenyl]-3-methyl-4-trifluorobutyramide, ESI 478;

(2S)-2-[3-(N-hydroxyamidino)phenylamino]-N-[4-(2-oxopiperidin-1-yl)benzyl]-2-phenylacetamide, ESI 472;

(2S)-2-[3-(N-hydroxyamidino)phenylamino]-N-[4-(3-oxo-2-azabicyclo[2.2.2]oct-2-yl)phenyl]-2-phenylacetamide, ESI 484

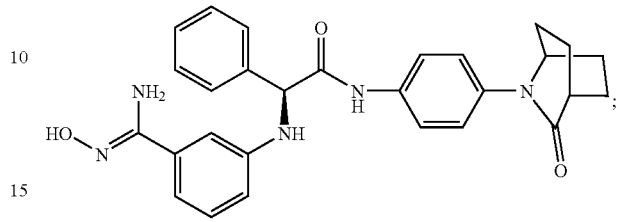

2-[3-(N-hydroxyamidino)phenoxy]-N-[4-(2-oxopiperidin-1-yl)phenyl]butyramide, ESI 411;

2-[3-(N-hydroxyamidino)phenoxy]-N-[4-(2-oxopiperidin-1-yl)phenyl]propionamide, ESI 397;

2-[3-(N-hydroxyamidino)phenylamino]-N-[3-trifluoromethyl-4-(3-oxo-2-azabicyclo[2.2.2]oct-2-yl)phenyl]-2-phenylacetamide, ESI 552;

3-[3-(N-hydroxyamidino)phenyl]-N-[4-(2-oxopiperidin-1-yl)phenyl]-2-phenylpropionamide, ESI 457;

3-[3-(N-hydroxyamidino)phenyl]-N-[3-methyl-4-(2-oxopiperidin-1-yl)phenyl]-2-phenylpropionamide, ESI 471;

2-[3-(N-hydroxyamidino)phenoxy]-N-[3-ethoxycarbonylmethoxy-4-(2-oxopiperidin-1-yl)phenyl]-2-phenylacetamide, ESI 561;

2-[3-(N-hydroxyamidino)phenoxy]-N-[3-ethoxycarbonylmethoxy4-(2-oxopiperidin-1-yl)phenyl]valeramide, ESI 561;

EXAMPLE 8a

1-{4-[2-(3-(N-Hydroxyamidino)phenoxy)-2-phenylethoxy]phenyl}piperidin-2-one, ESI 446, is prepared in accordance with the following scheme:

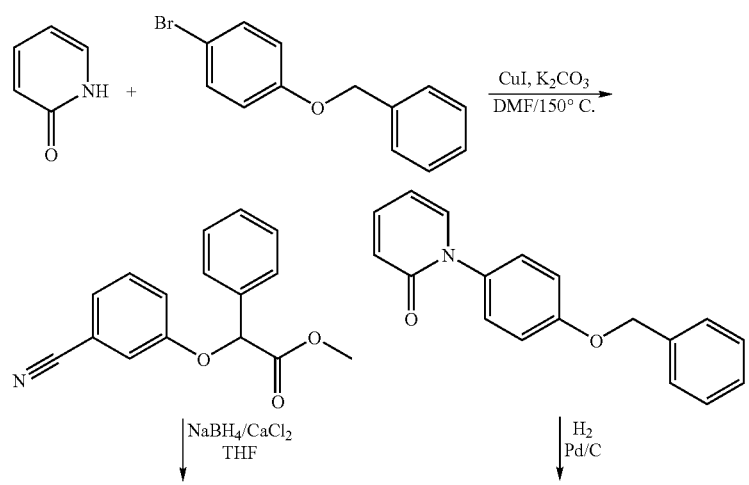

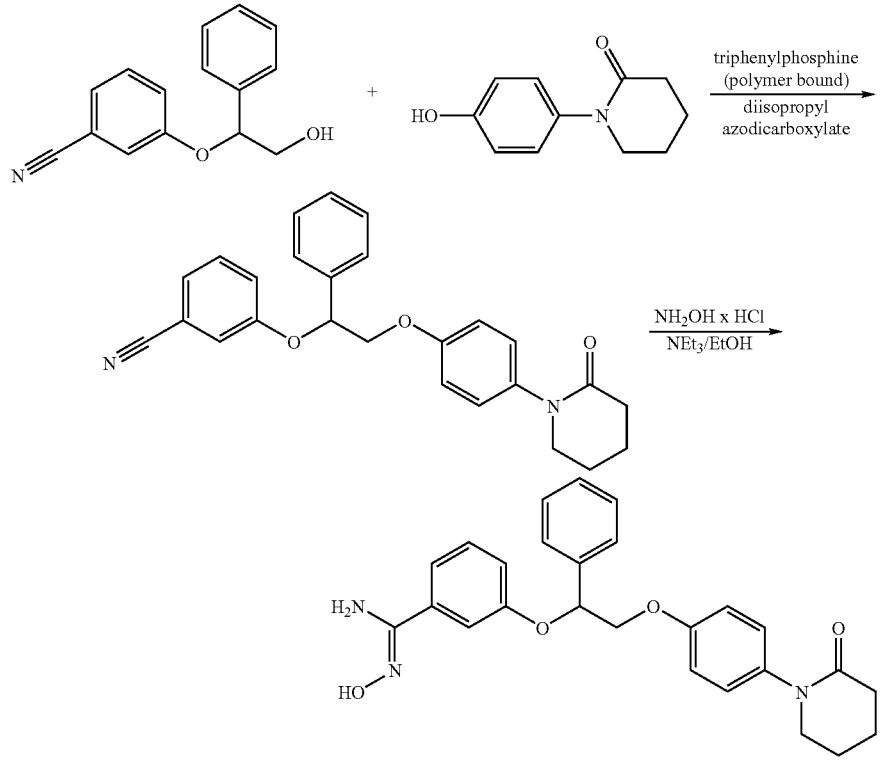
EXAMPLE 8b
2-[3-(N-ethoxycarbonyloxyamidino)phenoxy]-N-[4-(2-oxopiperidin-1-yl)phenyl]valeramide, ESI 483, is prepared in accordance with the following scheme
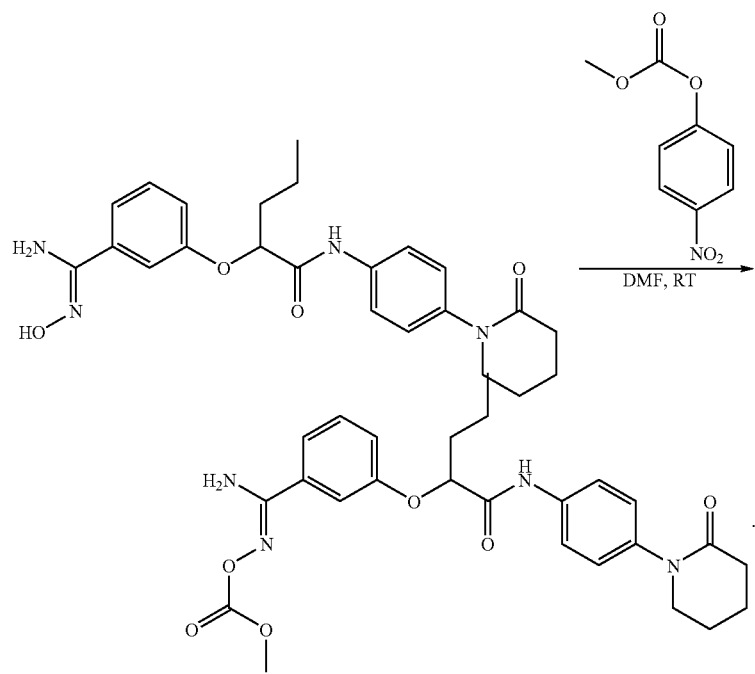

The following compounds are obtained analogously:
2-[3-(N-ethoxycarbonyloxyamidino)phenoxy]-N-[4-(2-oxopiperidin-1-yl)phenyl]valeramide, ESI 497;
(2S)-2-[3-(N-ethoxycarbonyloxyamidino)phenylamino]-N-[4-(2-oxo-piperidin-1-yl)phenyl]-4-methylvaleramide, ESI 494.

EXAMPLE 9

2-(3-Aminomethylphenylamino)-N-[3-methyl-4-(2-oxopiperidin-1-yl)phenyl]-2-(2-fluorophenyl)acetamide is prepared as indicated in the following scheme

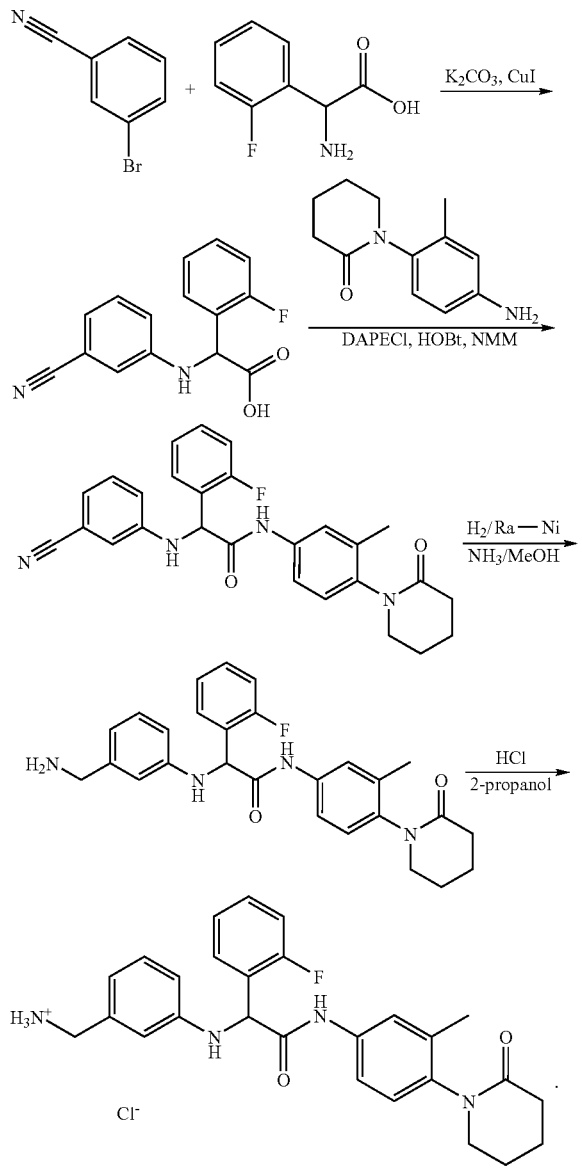

1. 6.5 g (47.0 mmol) of potassium carbonate and 597 mg (3.10 mmol) of copper(I) iodide are added to a solution of 5.70 g (31.3 mmol) of 3-bromobenzonitrile and 5.30 g (31.3 mmol) of 2-fluoro-dl-alpha-phenylglycine in 30 ml of N,N-dimethylacetamide, and the mixture is stirred at 90° C. for 48 hours. The reaction mixture is then poured into 80 ml of 1N HCl and extracted twice with diethyl ether. The combined organic phases are extracted twice with 50 ml of 1N NaOH each time. The two basic aqueous phases are combined, acidified using 25% HCl and extracted twice with 80 ml of diethyl ether each time. These two organic phases are combined, dried using sodium sulfate and subsequently evaporated, giving (3-cyanophenylamino)-2-fluorophenylacetic acid as a yellowish solid; ESI 270.

2. 225 μl (2.22 mmol) of 4-methylmorpholine are added to a solution of 600 mg (2.22 mmol) of (3-cyanophenylamino)-2-fluorophenylacetic acid, 453 mg (2.22 mmol) of 1-(4-amino-2-methylphenyl)piperidin-2-one, 426 mg (2.22 mmol) of N-(3-dimethylaminopropyl)-N'-ethylcarbodiimide hydrochloride (DAPECI) and 300 mg (2.22 mmol) of hydroxybenzotriazole hydrate (HOBt) in 1 ml of DMF, and the mixture is stirred at room temperature for 24 hours. The reaction mixture is introduced into water, and the precipitate is filtered off, giving 2-(3-cyanophenylamino)-2-(2-fluorophenyl)-N-[3-methyl-4-(2-oxopiperidin-1-yl)phenyl]acetamide as a colourless solid; ESI 456.

3. 300 mg of water-moist Raney nickel and 2.0 ml of methanolic ammonia solution are added to a solution of 660 mg (1.45 mmol) of 2-(3-cyanophenylamino)-2-(2-fluorophenyl)-N-[3-methyl-4-(2-oxopiperidin-1-yl)phenyl]acetamide in 6 ml of methanol, and the mixture is hydrogenated at 60° C. and 5 bar for 18 hours. The reaction mixture is filtered, and the filtrate is evaporated, giving 2-(3-cyanophenylamino)-2-(2-fluorophenyl)-N-[3-methyl-4-(2-oxopiperidin-1-yl)phenyl]acetamide as a colourless solid; ESI 460.

4. 1.87 ml of 0.1N HCl in 2-propanol are added to 86 mg (0.187 mmol) of 2-(3-cyanophenylamino)-2-(2-fluorophenyl)-N-[3-methyl-4-(2-oxopiperidin-1-yl)phenyl]acetamide, and the mixture is left to stand at room temperature for 2 hours. The reaction mixture is evaporated and subsequently lyophilised, giving 2-(3-cyanophenylamino)-2-(2-fluorophenyl)-N-[3-methyl-4-(2-oxopiperidin-1-yl)phenyl]acetamide, hydrochloride, as a colourless solid; ESI 460.

The following compounds are obtained analogously:
2-(3-aminomethylphenoxy)-N-[4-(2-oxopiperidin-1-yl)phenyl]-2-phenylacetamide, hydrochloride, ESI 430;
2-(3-aminomethylphenylamino)-N-[4-(2-oxopiperidin-1-yl)phenyl]-2-(2-fluorophenyl)acetamide, ESI 447;
3-(3-aminomethylphenyl)-N-[4-(2-oxopiperidin-1-yl)phenyl]propionamide, ESI 352;
2-(3-aminomethylphenylamino)-N-[4-(2-oxopiperidin-1-yl)phenyl]acetamide, ESI 353;
2-(3-aminomethylphenoxy)-N-[4-(2-oxopiperidin-1-yl)phenyl]valeramide, ESI 396;
(2S)-2-(3-aminomethylphenylamino) -N-[4-(2-caprolactam-1-yl)phenyl]-2-phenylacetamide, ESI 443;
(2S)-2-(3-aminomethylphenylamino)-N-[3-methyl-4-(2-oxopiperidin-1-yl)phenyl]acetamide, ESI 443;
2-(3-aminomethylphenylamino)-N-[4-(2-oxopiperidin-1-yl)phenyl]-2-(2-trifluoromethylphenyl)acetamide, ESI 497;
(2S)-2-(3-aminomethylphenylamino)-N-[4-(2-oxopiperidin-1-yl)phenyl]-2-phenylacetamide, ESI 429;
(2R)-2-(3-aminomethylphenylamino)-N-[4-(2-oxopiperidin-1-yl)phenyl]-2-phenylacetamide, ESI 429;
2-(3-aminomethylphenylamino)-N-[4-(2-oxopiperidin-1-yl)phenyl]-2-(2-methylphenyl)acetamide, ESI 443;
2-(3-aminomethylphenylamino]-N-[4-(2-caprolactam-1-yl)phenyl]-2-(2-fluorophenyl)acetamide, ESI 461;
2-(3-aminomethylphenylamino)-N-[3-methyl-4-(2-oxopiperidin-1-yl)phenyl]-2-(2-methylphenyl)acetamide, ESI 457;

2-(3-aminomethylphenylamino)-N-[3-methyl-4-(2-oxopiperidin-1-yl)phenyl]-2-(2-fluorophenyl)acetamide, ESI 461;

2-(3-aminomethylphenoxy)-N-[3-methyl-4-(2-oxopiperidin-1-yl)phenyl]valeramide, ESI 410;

2-(3-aminomethylphenylamino)-N-[4-(2-oxopiperidin-1-yl)phenyl]-2-(2-thienyl)acetamide, ESI 435;

2-(3-aminomethylphenylamino)-N-[3-fluoro-4-(2-oxopiperidin-1-yl)phenyl]-2-(3-fluorophenyl)acetamide, ESI 465;

(2S)-2-(3-aminomethylphenylamino)-N-[3-fluoro-4-(2-oxopiperidin-1-yl)phenyl]-2-phenylacetamide, ESI 447;

(2S)-2-(3-aminomethylphenylamino)-N-[3-methyl-4-(2-oxopiperidin-1-yl)phenyl]-2-phenylacetamide, hydrochloride, ESI 443;

(2S)-2-(2-aminomethylphenylamino)-N-[4-(2-oxopiperidin-1-yl)phenyl]-2-phenylacetamide, ESI 429;

2-(2-aminomethylphenyl)-N-[4-(2-oxopiperidin-1-yl)phenyl]acetamide, ESI 338;

2-(2-aminomethylphenoxy)-N-[4-(2-oxopiperidin-1-yl)phenyl]-2-phenylacetamide, ESI 430;

2-(4-aminomethylphenoxy)-N-[4-(2-oxopiperidin-1-yl)phenyl]-2-phenylacetamide, ESI 430;

2-(3-aminomethylphenylamino)-N-[4-(2-oxopiperidin-1-yl)phenyl]-2-(3-fluorophenyl)acetamide, ESI 447;

2-(3-aminomethylphenoxy)-N-[3-methyl-4-(2-caprolactam-1-yl)phenyl]-2-phenylacetamide, ESI 458;

(2R)-2-(3-aminomethylphenylamino)-N-[3-methyl-4-(2-caprolactam-1-yl)phenyl]-2-phenylacetamide, ESI 457;

(2R)-2-(2-aminomethylphenylamino)-N-[4-(2-oxopiperidin-1-yl)phenyl]-2-phenylacetamide, ESI 429;

(2S)-2-(3-aminomethylphenylamino)-N-[3-methyl-4-(2-caprolactam-1-yl)phenyl]-2-phenylacetamide, ESI 457;

2-(3-aminomethylphenylamino)-N-[4-(2-oxopiperidin-1-yl)phenyl]-2-cyclohexylacetamide, ESI 435;

2-(3-aminomethylphenylamino)-N-[3-methyl-4-(2-oxopiperidin-1-yl)phenyl]-2-cyclohexylacetamide, ESI 449;

2-(3-aminomethylphenylamino)-N-[4-(2-caprolactam-1-yl)phenyl]-4-methylvaleramide, ESI 423;

(2R)-2-(3-aminomethylphenylamino)-N-[3-methyl-4-(2-oxopiperidin-1-yl)phenyl]-2-phenylacetamide, hydrochloride, ESI 443;

(2S)-2-(3-aminomethylphenylamino)-N-[4-(2-oxopyridin-1-yl)phenyl]-2-phenylacetamide, ESI 425;

2-(3-aminomethylphenylamino)-N-[4-(2-oxopiperidin-1-yl)phenyl]valeramide, ESI 395;

2-(3-aminomethylphenylamino)-N-[4-(2-oxopiperidin-1-yl)phenyl]-4-methylvaleramide, ESI 409;

(2R)-2-(3-aminomethylphenylamino)-N-[3-methyl-4-(2-oxopiperidin-1-yl)phenyl]-4-methylvaleramide, ESI 423;

(2R)-2-(3-aminomethylphenylamino)-N-[3-fluoro-4-(2-oxopiperidin-1-yl)phenyl]-4-methylvaleramide, ESI 427;

(2R)-2-(3-aminomethylphenylamino)-N-[4-(2-caprolactam-1-yl)phenyl]-4-methylvaleramide, ESI 423;

(2S)-2-(3-aminomethylphenylamino)-N-[2,5-dimethyl-4-(2-oxopiperidin-1-yl)phenyl]-2-phenylacetamide, hydrochloride, ESI 457;

2-(3-aminomethylphenylamino)-N-[3-fluoro-4-(2-oxopiperidin-1-yl)phenyl]-2-(2-fluorophenyl)acetamide, hydrochloride, ESI 465;

2-(3-aminomethylphenylamino)-N-[3-methyl-4-(2-caprolactam-1-yl)phenyl]-2-(2-fluorophenyl)acetamide, hydrochloride, ESI 475;

2-(3-aminomethylphenylamino)-N-[3-methyl-4-(2-oxopiperidin-1-yl)phenyl]-2-(2,4-difluorophenyl)acetamide, hydrochloride, ESI 479;

2-(3-aminomethylphenylamino)-N-[4-(2-oxopiperidin-1-yl)phenyl]-2-(2,4-difluorophenyl)acetamide, hydrochloride, ESI 465;

(2S)-2-(3-aminomethylphenylamino)-N-[3-methyl-4-(2-oxopyrrolidin-1-yl)phenyl]-2-phenylacetamide, hydrochloride, ESI 429;

(2S)-2-(3-aminomethylphenylamino)-N-[3-methyl-4-(2-oxopiperidin-1-yl)phenyl]-4-methylvaleramide, ESI 423;

2-(3-aminomethylphenylamino)-N-methyl-N-[4-(2-oxopiperidin-1-yl)phenyl]-2-phenylacetamide, ESI 443;

2-(3-aminoethylphenylamino)-N-[4-(2-oxopiperidin-1-yl)phenyl]-2-phenylacetamide, hydrochloride, ESI 443;

2-(3-aminomethylphenylamino)-N-[3-methyl-4-(2-oxopyrrolidin-1-yl)phenyl]-2-(2-fluorophenyl)acetamide, hydrochloride, ESI 447;

2-(3-aminomethylphenylamino)-N-[4-(2-oxopiperidin-1-yl)phenyl]-4-trifluoro-3-methylbutyramide, ESI 449;

2-(3-aminomethylphenylamino)-N-[4-(2-oxopiperidin-1-yl)benzyl]-2-phenylacetamide, ESI 443;

(2S)-2-(3-aminomethylphenylamino)-N-[4-(3-oxo-2-azabicyclo[2.2.2]-oct-2-yl)phenyl]-2-phenylacetamide, ESI 455;

2-(3-aminomethylphenylamino)-N-[3-fluoro-4-(2-oxopyrrolidin-1-yl)phenyl]-2-(2-fluorophenyl)acetamide, hydrochloride, ESI 451;

2-(3-aminomethylphenylamino)-N-[4-(2-oxopyrrolidin-1-yl)phenyl]-2-phenylacetamide, hydrochloride, ESI 415;

2-(3-aminomethylphenylamino)-N-[4-(2-oxopyrrolidin-1-yl)phenyl]-2-(2-fluorophenyl)acetamide, hydrochloride, ESI 433;

2-(3-aminomethylphenylamino)-N-[4-ethyl-3-(2-oxopyrrolidin-1-yl)phenyl]-2-phenylacetamide, ESI 443;

(2S)-2-(3-aminomethylphenylamino)-N-[3-methoxy-4-(3-oxo-2-azabicyclo[2.2.2]oct-2-yl)phenyl]-2-phenylacetamide, ESI 485:

2-(3-aminomethylphenylamino)-N-[3-fluoro-4-(2-caprolactam-1-yl)phenyl]-2-(2-fluorophenyl)acetamide, ESI 479;

(2S)-2-(3-aminomethylphenylamino)-N-[3-fluoro-4-(2-caprolactam-1-yl)phenyl]-2-phenylacetamide, ESI 461;

(2S)-2-(3-aminomethylphenylamino)-N-[3-trifluoromethyl-4-(3-oxo-2-azabicyclo[2.2.2]oct-2-yl)phenyl]-2-phenylacetamide, ESI 523;

2-(3-aminomethylphenylamino)-N-[3-methyl-4-(3-oxo-2-azabicyclo-[2.2.2]oct-2-yl)phenyl]-2-phenylacetamide, ESI 469;

(2S)-2-(3-aminomethylphenylamino)-N-[3-methoxy-4-(3-oxo-2-azabicyclo[2.2.2]oct-2-yl )phenyl]-2-phenylacetamide, ESI 485;

2-(3-aminomethylphenylamino)-N-[3-trifluoromethyl-4-(2-oxopiperidin-1-yl)phenyl]-2-phenylacetamide, ESI 497;

2-(3-aminomethylphenylamino)-N-[3-methoxy-4-(2-oxopiperidin-1-yl)phenyl]-2-phenylacetamide, ESI 459;

2-(3-aminomethylphenylamino)-N-[3-methyl-4-(3-oxo-2-azabicyclo-[2.2.2]oct-2-yl)phenyl]-2-(2-fluorophenyl)acetamide, ESI 487;

2-(3-aminomethyl-4-fluorophenylamino)-N-[4-(2-oxopiperidin-1-yl)phenyl]-2-phenylacetamide, ESI 447;

2-(3-aminomethylphenylamino)-N-[3-methyl-4-(3-oxo-2-azabicyclo-[2.2.2]oct-2-yl)phenyl]-2-(2-fluorophenyl)acetamide, hydrochloride, ESI 487;

2-(3-aminomethylphenylamino)-N-[3-chloro-4-(2-oxopyrrolidin-1-yl)phenyl]-2-(2-fluorophenyl)acetamide, hydrochloride, ESI 467;

2-(3-aminomethylphenylamino)-N-[3-methoxy-4-(2-oxopiperidin-1-yl)phenyl]-2-(2-fluorophenyl)acetamide, ESI 477;

2-(3-aminomethylphenylamino)-N-[3-trifluoromethyl-4-(3-oxo-2-azabicyclo[2.2.2]oct-2-yl)phenyl]-2-phenylacetamide, hydrochloride, ESI 523;

2-(3-aminomethylphenylamino)-N-[3-trifluoromethyl-4-(2-oxopiperidin-1-yl)phenyl]-2-phenylacetamide, hydrochloride, ESI 497;

3-(3-aminomethylphenyl)-N-[4-(2-caprolactam-1-yl)phenyl]-2-phenylpropionamide, hydrochloride, ESI 456;

2-(3-aminomethylphenoxy)-N-[3-methyl-4-(2-oxopyrrolidin-1-yl)phenyl]-2-(2-fluorophenyl)acetamide, hydrochloride, ESI 448;

3-(3-aminomethylphenyl)-N-[4-(2-oxopiperidin-1-yl)phenyl]-2-phenylpropionamide, hydrochloride, ESI 428;

2-(3-aminomethylphenoxy)-N-[3-methyl-4-(2-caprolactam-1-yl)phenyl]-2-(2-fluorophenyl)acetamide, hydrochloride, ESI 476;

3-(3-aminomethylphenyl)-N-[3-methyl-4-(2-oxopiperidin-1-yl)phenyl]-2-phenylpropionamide, hydrochloride, ESI 442;

2-(3-aminomethylphenoxy)-N-[4-(2-oxopiperidin-1-yl)phenyl]-2-(2-fluorophenyl)acetamide, hydrochloride, ESI 448;

2-(3-aminomethylphenoxy)-N-[3-methyl-4-(2-oxopiperidin-1-yl)phenyl]-2-(2-fluorophenyl)acetamide, hydrochloride, ESI 462;

3-(3-aminomethylphenyl)-N-[3-methyl-4-(2-oxopyrrolidin-1-yl)phenyl]-2-phenylpropionamide, hydrochloride, ESI 428;

(2S)-2-(3-aminomethylphenylamino)-N-[4-(5,5-dimethyl-2-oxopyrrolidin-1-yl)phenyl]-2-phenylacetamide, ESI 443;

(2S)-2-(3-aminomethylphenylamino)-N-[3-methyl-4-(2-oxo-1,3oxazinan-3-yl)phenyl]-2-phenylacetamide, ESI 445;

(2S)-2-(3-aminomethylphenylamino)-N-[3-methyl-4-(2-oxooxazolidin-3-yl)phenyl]-2-phenylacetamide, hydrochloride, ESI 431;

3-(3-aminomethylphenyl)-N-[3-methyl-4-(2-oxopiperidin-1-yl)phenyl]-2-(2-fluorophenyl)propionamide, hydrochloride, ESI 460;

3-(3-aminomethylphenyl)-N-[4-(2-oxopiperidin-1-yl)phenyl]-2-(2-fluorophenyl)propionamide, hydrochloride, ESI 446;

3-(3-aminomethylphenylamino)-N-[3-chloro-4-(2-oxopiperidin-1-yl)phenyl]-2-(2-fluorophenyl)acetamide, hydrochloride, ESI 481;

3-(3-aminomethylphenylamino)-N-[3-chloro-4-(2-oxopiperidin-1-yl)phenyl]-2-phenylacetamide, hydrochloride, ESI 463;

3-(3-aminomethylphenoxy)-N-[3-chloro-4-(2-oxopiperidin-1-yl)phenyl]-2-(2-fluorophenyl)acetamide, hydrochloride, ESI 482;

3-(3-aminomethylphenyl)-N-[3-methyl-4-(2-oxopyrrolidin-1-yl)phenyl]-2-(2-fluorophenyl)propionamide, hydrochloride, ESI 446;

3-(3-aminomethylphenyl)-N-[3-chloro-4-(2-oxopiperidin-1-yl)phenyl]-2-(2-fluorophenyl)propionamide, hydrochloride, ESI 480;

3-(3-aminomethylphenylamino)-N-[4-(2,6-dioxopiperidin-1-yl)phenyl]-2-phenylacetamide, trifluoroacetate, ESI 443;

2-(3-aminomethylphenylamino)-N-[3-chloro-4-(2,5-dioxopyrrolidin-1-yl)phenyl]-2-phenylacetamide, ditrifluoroacetate, ESI 463;

2-(3-aminomethyl-4-fluorophenylamino)-N-[3-methyl-4-(3-oxo-2-azabicyclo[2.2.2]oct-2-yl)phenyl]-2-phenylacetamide, hydrochloride, ESI 487;

2-[3-(N-tert-butoxycarbonylaminomethyl)phenylamino]-N-[3-chloro-4-(2,5-dioxopyrrolidin-1-yl)phenyl]-2phenylacetamide, ESI 563;

2-(3-aminomethylphenylamino)-N-[3-methyl-4-(3-oxo-2-azabicyclo[2.2.2]oct-2-yl)phenyl]-2-(2-fluorophenyl)acetamide, hydrochloride, ESI 487;

2-(3-aminomethylphenylamino)-N-[3-methyl-4-(2-oxooxazolidin-3-yl)phenyl]-2-(2-fluorophenyl)acetamide, hydrochloride, ESI 449;

3-(3-aminomethylphenylamino)-N-[3-methoxy-4-(2-oxopiperidin-1-yl)phenyl]-2-(2-fluorophenyl)acetamide, hydrochloride, ESI 477;

3-(3-aminomethylphenylamino)-N-[3-chloro-4-(2-oxopyrrolidin-1-yl)phenyl]-2-phenylacetamide, hydrochloride, ESI 449;

2-(3-aminomethylphenoxy)-N-[3-methyl-4-(3-oxo-2-azabicyclo[2.2.2]-oct-2-yl)phenyl]-2-fluorophenyl)acetamide, hydrochloride, ESI 488;

3-(3-aminomethylphenylamino)-N-[4-(5,5-dimethyl-2-oxopyrrolidin-1-yl)phenyl]-2-(2-fluorophenyl)acetamide, hydrochloride, ESI 461;

3-(3-aminomethylphenoxy)-N-[4-(5,5-dimethyl-2-oxopyrrolidin-1-yl)phenyl]-2-(2-fluorophenyl)acetamide, hydrochloride, ESI 462;

2-(3-aminomethylphenoxy)-N-[3-methyl-4-(2-oxo-oxazolidin-3-yl)phenyl]-2-(2-fluorophenyl)acetamide, hydrochloride, ESI 450;

3-(3-aminomethylphenoxy)-N-[3-methoxy-4-(2-oxopiperidin-1-yl)phenyl]-2-(2-fluorophenyl)acetamide, hydrochloride, ESI 478.

EXAMPLE 9a (2S)-2-(3-Aminoethylphenylamino)-N-[4-(2-oxopiperidin-1-yl)phenyl]-2-phenylacetamide, hydrochloride, ESI 443, is prepared in accordance with the following scheme

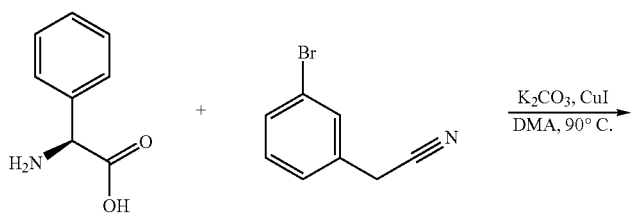

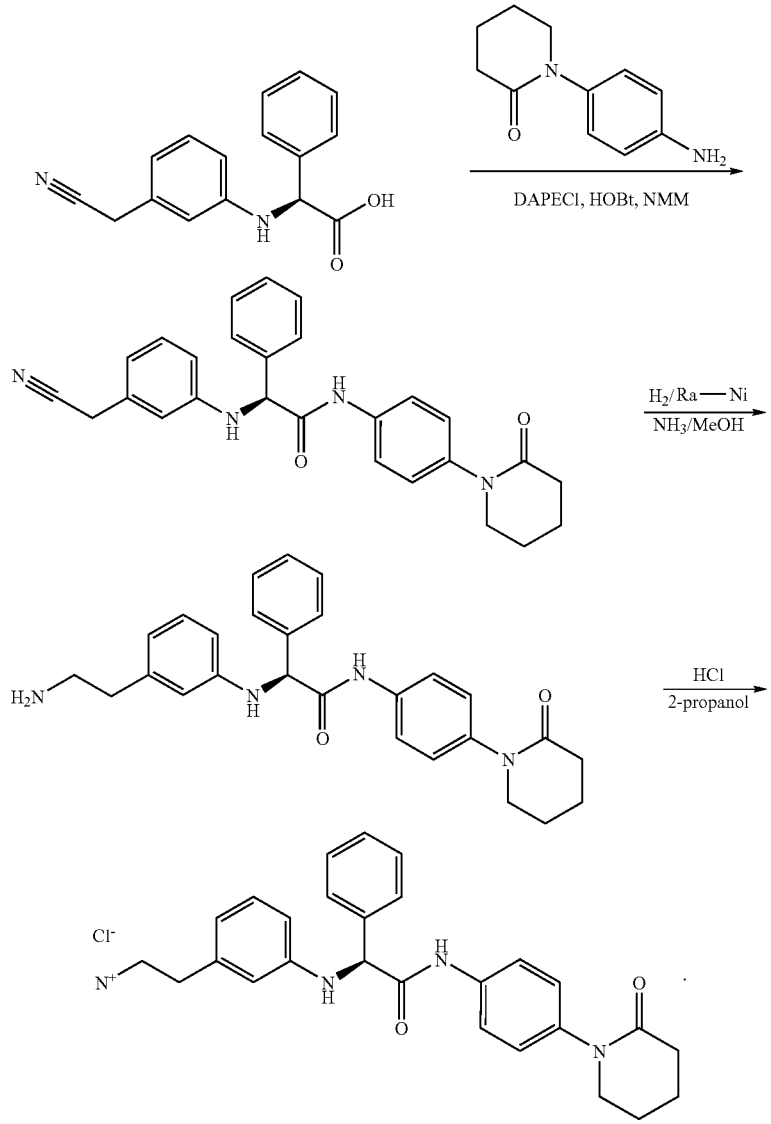
EXAMPLE 10
The following is obtained analogously to Example 3:
2-(3-amidinophenoxy)-N-[4-(2-oxopiperazin-1-yl)phenyl]-2-phenylacetamide, diformate, ESI 444.
EXAMPLE 10a
2-(3-Amidinophenoxy)-N-[3-carboxymethoxy-4-(2-oxopiperidin-1-yl)phenyl]-2-phenylacetamide is prepared as indicated in the following scheme
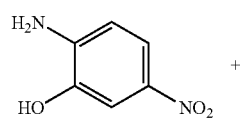
+
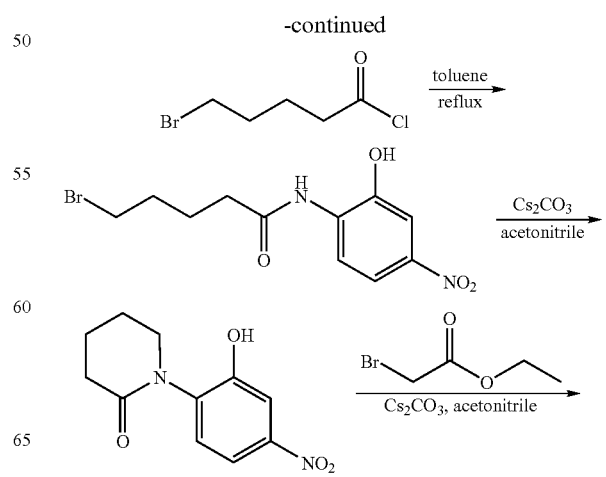

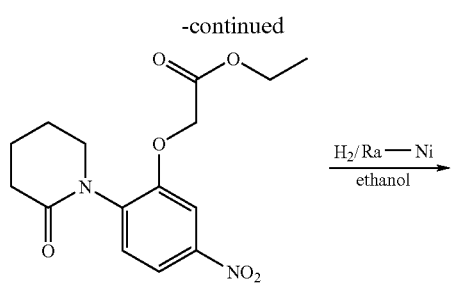
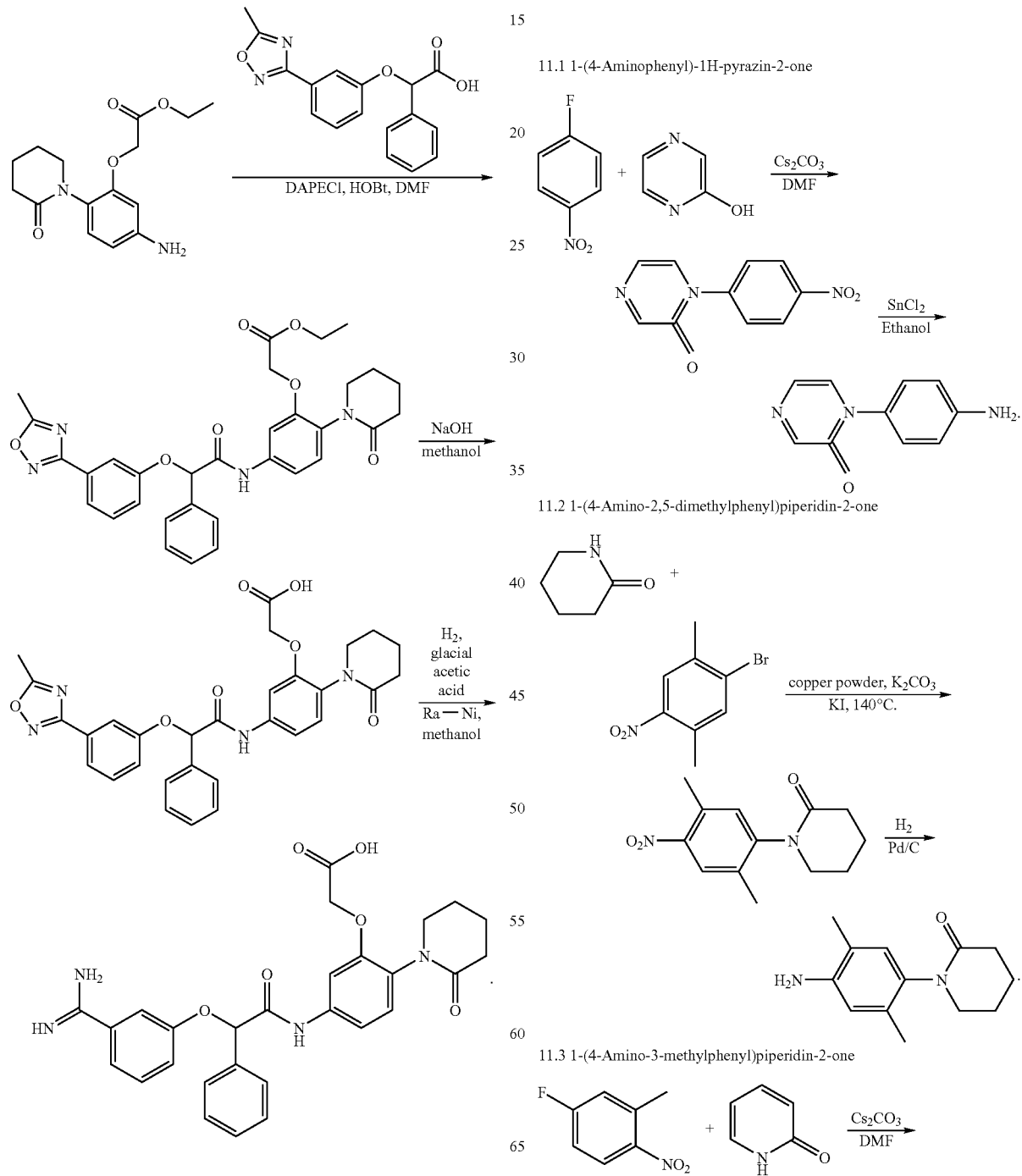

The following compounds are obtained analogously:
2-(3-amidinophenoxy)-N-[3-ethoxycarbonylmethoxy-4-(2-oxopiperidin-1-yl)phenyl]-2-phenylacetamide, acetate, ESI 545;
2-[(3-amidinophenoxy)-N-[3-ethoxycarbonylmethoxy-4-(2-oxopiperidin-1-yl)phenyl]valeramide, acetate, ESI 511;
3-(3-amidinophenoxy)-N-[3-carboxymethoxy-4-(2-oxopiperidin-1-yl)phenyl]valeramide, acetate, ESI 483;
3-(3-amidinophenoxy)-N-[3-carboxymethoxy-4-(2-oxopiperidin-1-yl)phenyl]-2-phenylacetamide, acetate, ESI 517.

11. EXAMPLES OF THE PREPARATION OF INTERMEDIATES 11.1 1-(4-Aminophenyl)-1H-pyrazin-2-one 11.2 1-(4-Amino-2,5-dimethylphenyl)piperidin-2-one 11.3 1-(4-Amino-3-methylphenyl)piperidin-2-one -continued
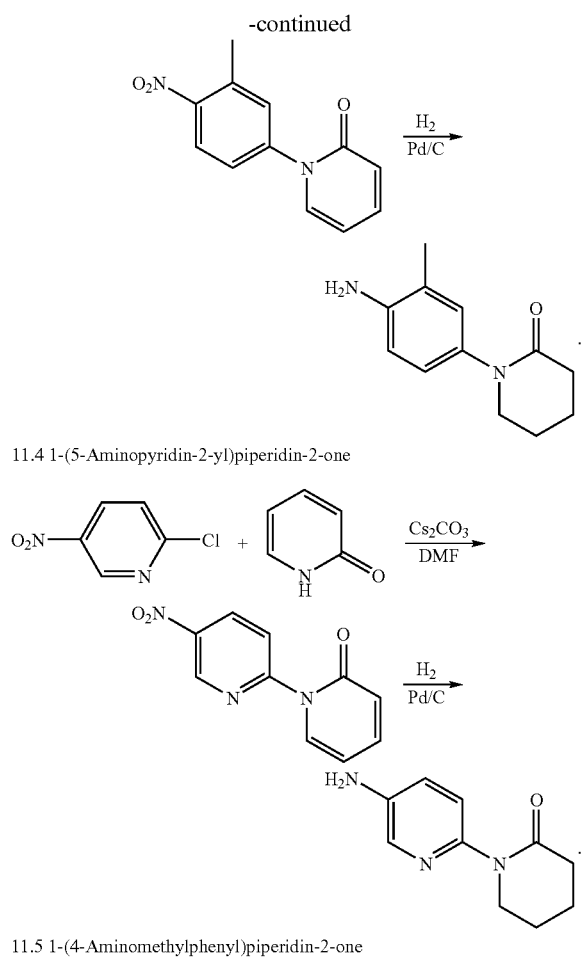
11.4 1-(5-Aminopyridin-2-yl)piperidin-2-one
11.5 1-(4-Aminomethylphenyl)piperidin-2-one
-continued
11.6 2-(4-Aminophenyl)-2-azabicyclo[2.2.2]octan-3-one
11.7 1-(3-Amino-6-ethylphenyl)pyrrolidin-2-one
11.8 2-(4-Amino-2-trifluoromethylphenyl)-2-azabicyclo[2.2.2]octan-3-one
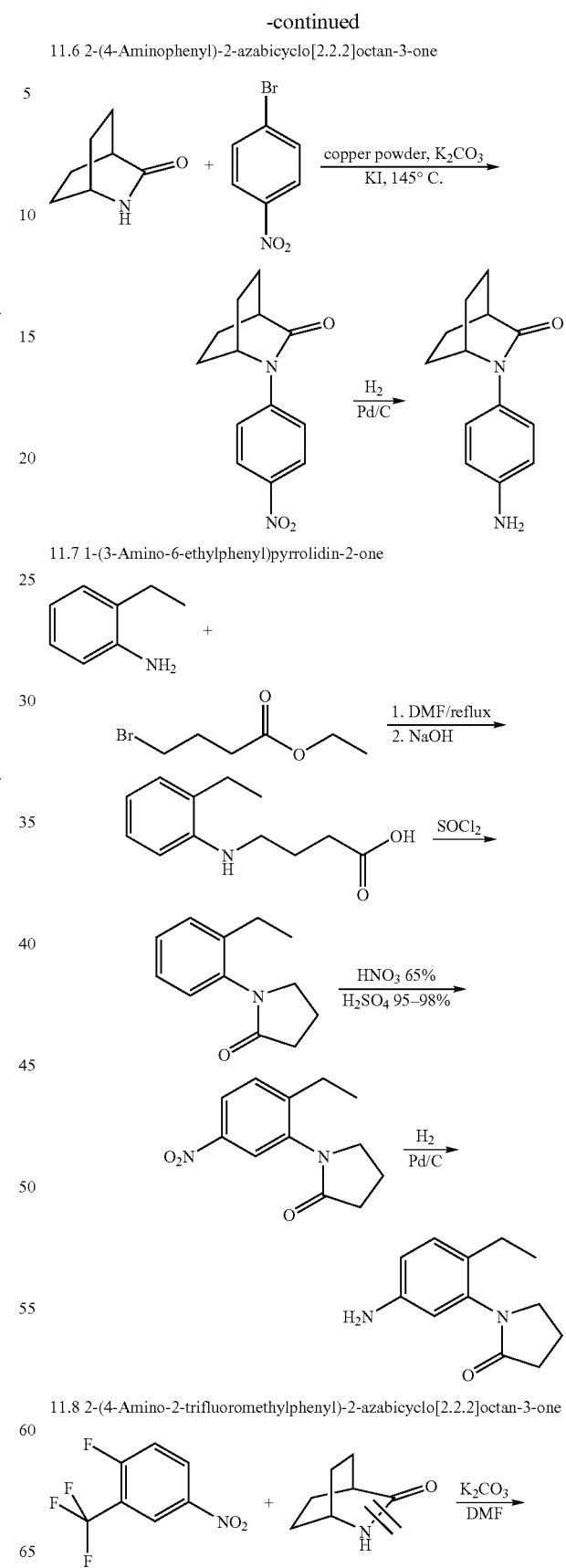

-continued
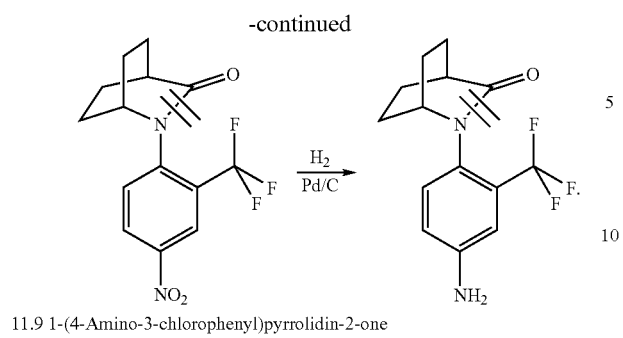
11.9 1-(4-Amino-3-chlorophenyl)pyrrolidin-2-one
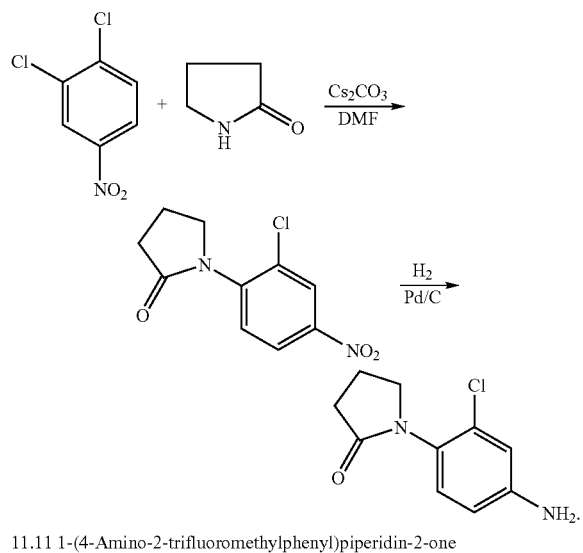
11.11 1-(4-Amino-2-trifluoromethylphenyl)piperidin-2-one
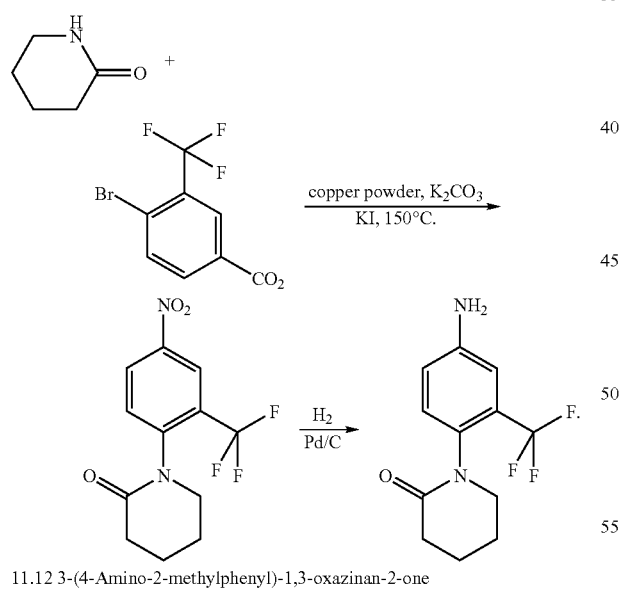
11.12 3-(4-Amino-2-methylphenyl)-1,3-oxazinan-2-one
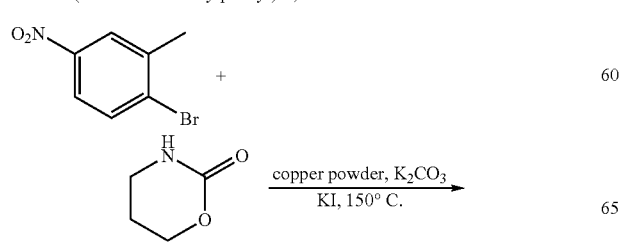
-continued
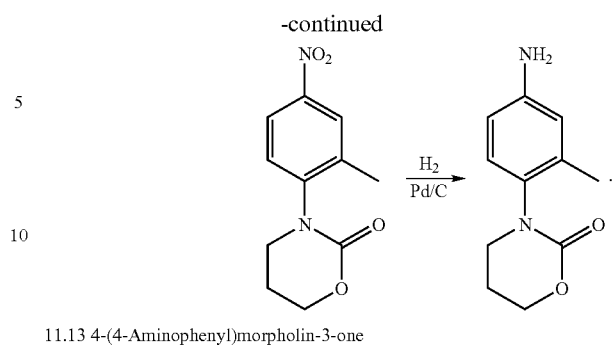
11.13 4-(4-Aminophenyl)morpholin-3-one
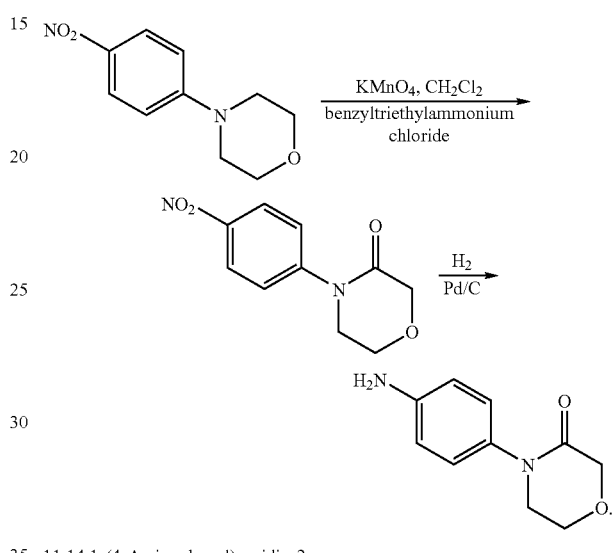
11.14 1-(4-Aminophenyl)pyridin-2-one
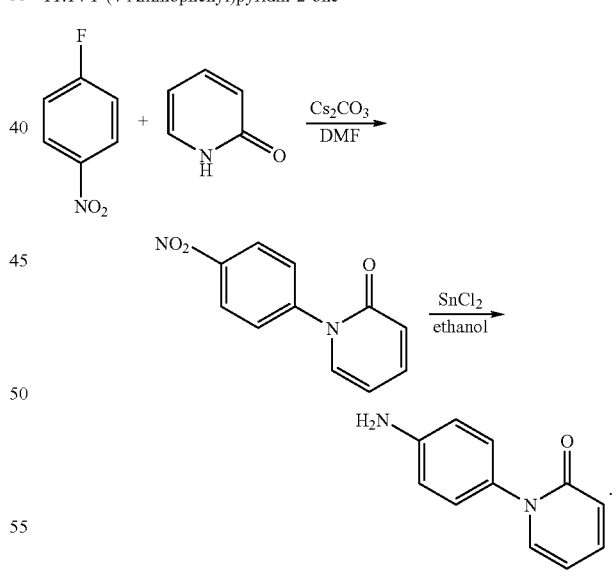
11.15 1-(4-Amino-2-methylphenyl)piperidin-2-one
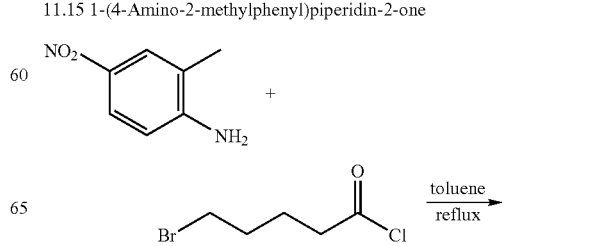

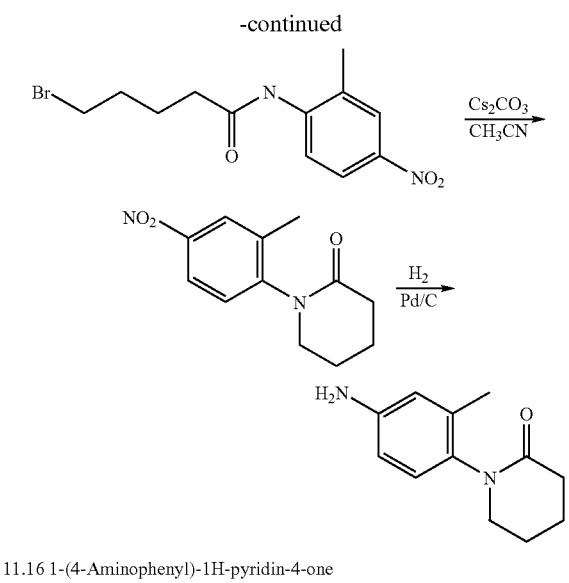
11.16 1-(4-Aminophenyl)-1H-pyridin-4-one
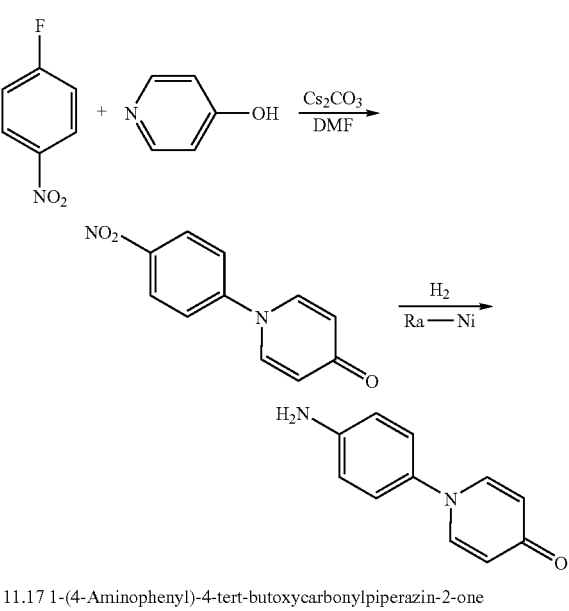
11.17 1-(4-Aminophenyl)-4-tert-butoxycarbonylpiperazin-2-one
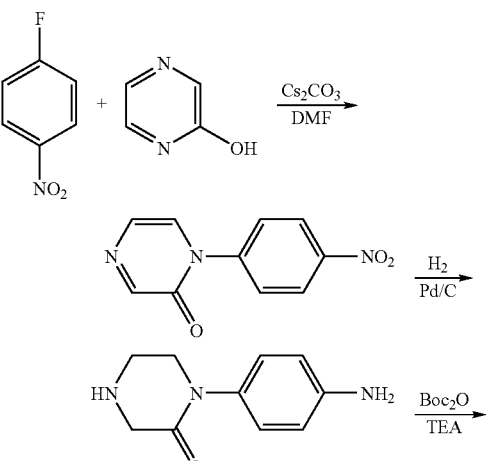
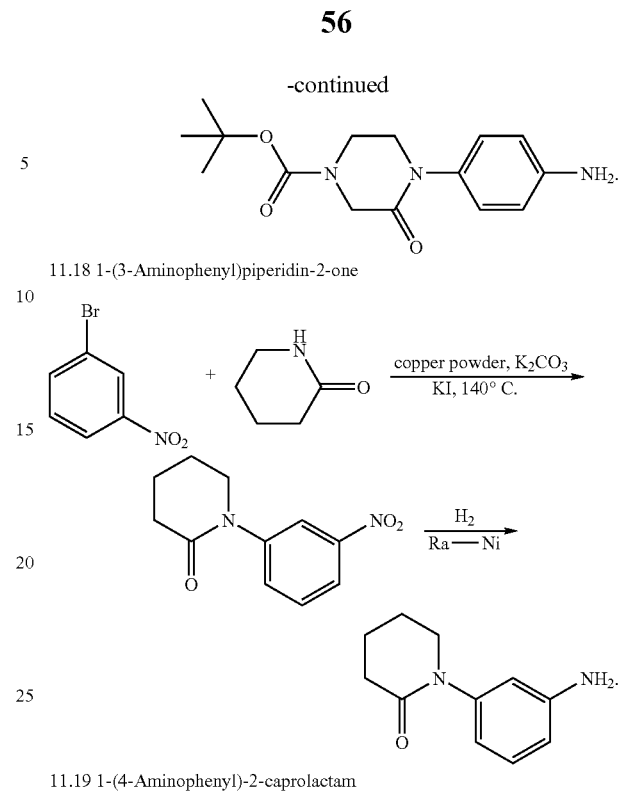
11.18 1-(3-Aminophenyl)piperidin-2-one
11.19 1-(4-Aminophenyl)-2-caprolactam
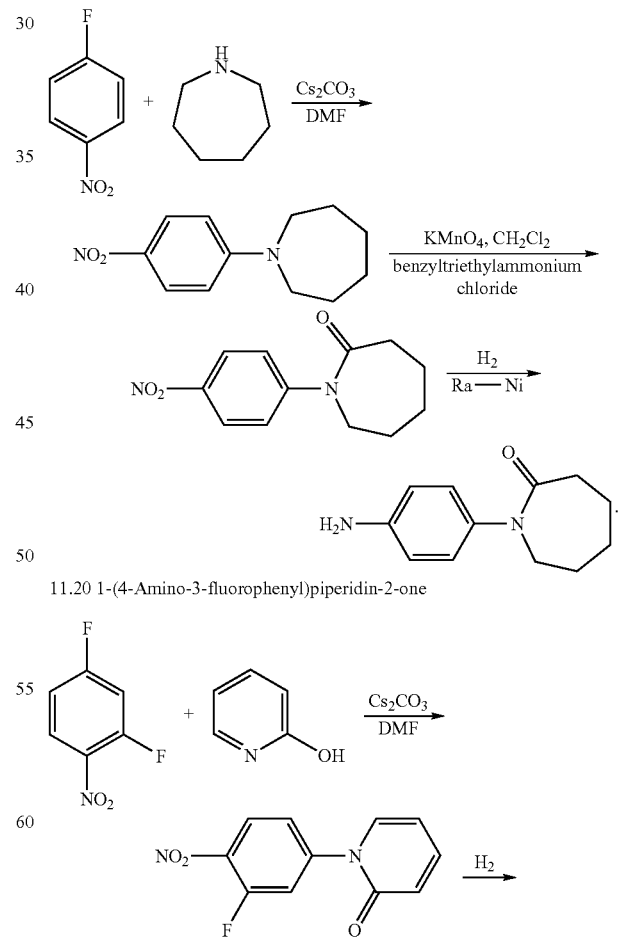
11.20 1-(4-Amino-3-fluorophenyl)piperidin-2-one

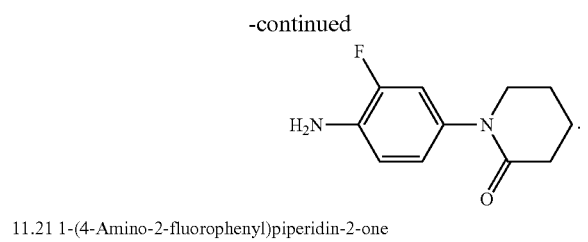

11.21 1-(4-Amino-2-fluorophenyl)piperidin-2-one

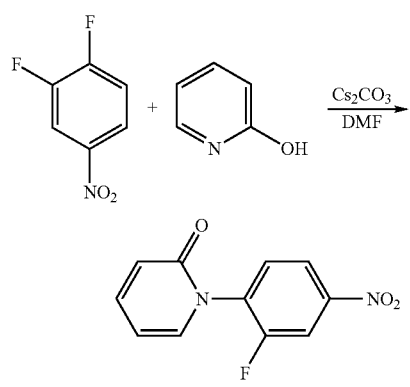

11.22 1-(4-Amino-2-fluoro)-2-caprolactam

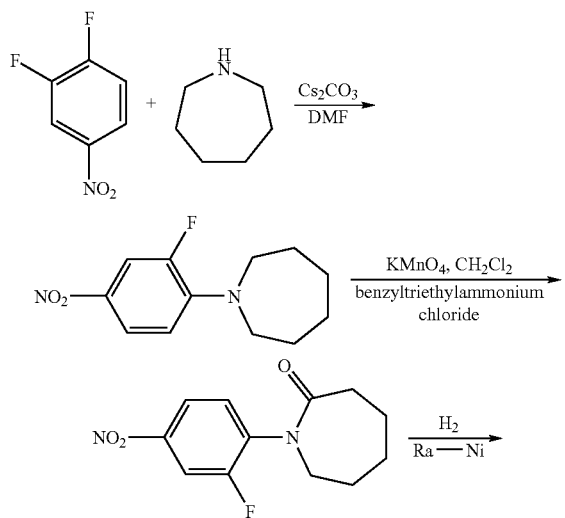

11.23 2-(2-Fluorophenyl)-3-(3-cyanophenyl)propionic acid

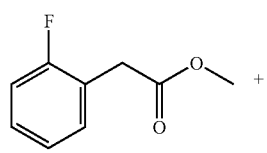

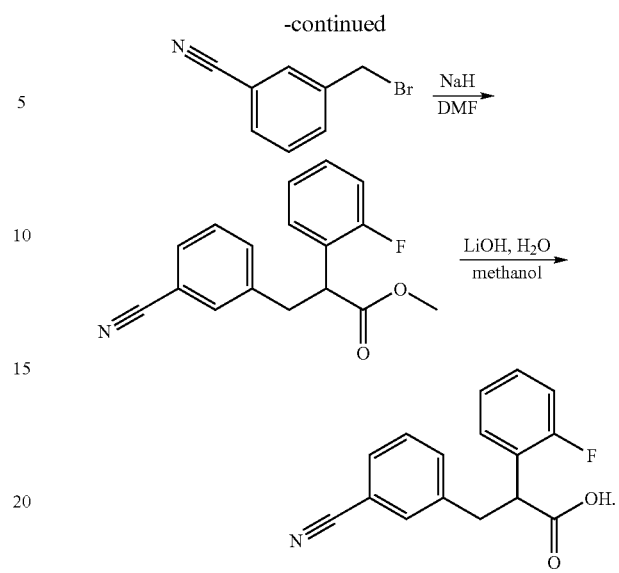

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. Compounds of the formula I:

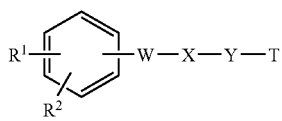

in which
$R^1$ is CN, $NH_2$, $CONH_2$, $CONA_2$, $CH_2NH_2$, $CH_2CH_2NH_2$, —C(=NH)—$NH_2$ which is unsubstituted or monosubstituted by OH, OCOA or OCOOA, or is

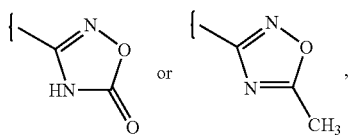

$R^2$ is H or F,
$R^3$ is H, A or —(CH$_2$)$_n$—Ar or thienyl,
W is —C(R$^3$)$_2$—, —OC(R$^3$)$_2$— or —NR$^3$C(R$^3$)$_2$—,
X is CONH, CONH(CH$_2$),
Y is alkylene, Ar-diyl or pyridinediyl,
T is dimethylamino, diethylamino, 2-oxopiperidin-1-yl, 2-oxopyrrolidin-1-yl, 5,5-dimethyl-2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl, 2-oxo-1,3-oxazinan-3-yl or 2-azabicyclo[2.2.2]octan-3-on-2-yl,
Ar is phenyl which is unsubstituted or monosubstituted or disubstituted by Hal, CF$_3$, A, OA, methoxycarbonylmethoxy, ethoxycarbonylmethoxy or carboxymethoxy,
A is unbranched or branched alkyl having 1-6 carbon atoms, in which 1-7 H atoms may be replaced by F,
n is 0 or 1,
and their pharmaceutically acceptable salt and stereoisomers, including mixtures thereof in all ratios.

2. Compounds according to claim 1, selected from the group consisting of:
2-(3-amidinophenylamino)-N-(4-dimethylaminophenyl)-4-methylvaleramide,
2-(3-amidinophenoxy)-N-[4-(2-oxopiperidin-1-yl)phenyl]-2-phenylacetamide,
2-(3-amidinophenoxy)-N-[4-(2-oxopyrrolidin-1-yl)phenyl]-2-phenylacetamide;
2-(3-amidinophenoxy)-N-[4-(2-oxopiperidin-1-yl)phenyl]valeramide,
2-(3-amidinophenoxy)-N-[4-(2-oxopyrrolidin-1-yl)phenyl]valeramide,
2-(3-amidinophenoxy)-N-[4-(2-oxo-1H-pyridin-1-yl)phenyl]-2-phenylacetamide,
2-(3-amidinophenoxy)-N-[4-(3-oxomorpholin-4-yl)phenyl]-2-phenylacetamide,
2-(3-amidinophenoxy)-N-[4-(4-oxo-1H-pyridin-1-yl)phenyl]-2-phenylacetamide,
2-(3-(N-hydroxyamidino)phenoxy)-N-[4-(2-oxopiperidin-1-yl)phenyl]-2-phenylacetamide,
2-(3-amidinophenoxy)-N-[4-(2,6-dioxopiperidin-1-yl)phenyl]-2-phenylacetamide,
2-(3-amidinophenoxy)-N-[4-(3-oxo-2H-piperazin-1-yl)phenyl]-2-phenylacetamide,
2-(3-amidinophenoxy)-N-[2-fluoro-4-(2-oxo-1H-pyridin-1-yl)phenyl]-2-phenylacetamide,
2-(3-amidinophenoxy)-N-[4-(2,5-dioxopyrrolidin-1-yl)phenyl]-2-phenylacetamide,
2-(3-amidinophenoxy)-N-[5-(2-oxopiperidin-1-yl)pyridin-2-yl]-2-phenylacetamide,
2-(3-amidinophenoxy)-N-[4-(2-oxo-1,3-oxazolidin-3-yl)phenyl]-2-phenylacetamide,
2-(3-amidinophenoxy)-N-[4-(2-oxo-1H-pyridin-1-yl)benzyl]-2-phenylacetamide,
2-(3-amidinophenoxy)-N-[4-(2-oxopiperidin-1-yl)butyl]-2-phenylacetamide,
2-(3-amidinophenoxy)-N-[4-(3-oxo-2H-pyridazin-2-yl)phenyl]-2-phenylacetamide,
2-(3-amidinophenoxy)-N-[2-fluoro-4-(2-oxopiperidin-1-yl)phenyl]-2-phenylacetamide,
2-(3-amidinophenoxy)-N-(4-dimethylaminobenzyl)-2-phenylacetamide,
2-(3-amidinophenoxy)-N-(4-dimethylaminophenyl)-2-phenylacetamide,
2-(3-amidinophenylamino)-N-[4-(2-oxopiperidin-1-yl)phenyl]-2-phenylacetamide,
2-(3-amidinophenylamino)-N-(4-dimethylaminobenzyl)-2-phenylacetamide,
2-(3-amidinophenoxy)-N-(4-dimethylaminobenzyl)valeramide,
2-(3-aminocarbonylphenoxy)-N-[4-(2-oxopiperidin-1-yl)phenyl]-2-phenylacetamide, 2-(3-aminocarbonylphenoxy)-N-(4-dimethylaminobenzyl)-2-phenylacetamide,
2-(3-amidinophenoxy)-N-[4-(3-oxomorpholin-4-yl)phenyl]-2-phenylacetamide,
2-(3-amidinophenoxy)-N-[3-(2-oxopiperidin-1-yl)phenyl]-2-phenylacetamide,
2-(3-amidinophenoxy)-N-[3-methyl-4-(2-oxopiperidin-1-yl)phenyl]-2-phenylacetamide,
(2R)-2-(3-amidinophenoxy)-N-[4-(2-oxopiperidin-1-yl)phenyl]valeramide,
2-(3-amidinophenoxy)-N-[2-fluoro-4-(2-oxopiperidin-1-yl)phenyl]-2-phenylacetamide,
2-(3-amidinophenoxy)-N-[2-fluoro-4-(2-caprolactam-1-yl)phenyl]-2-phenylacetamide,
2-(3-amidinophenoxy)-N-[3-methyl-4-(2-caprolactam-1-yl)phenyl]valeramide,
2-(3-amidinophenoxy)-N-[3-methyl-4-(2-oxopiperidin-1-yl)phenyl]valeramide,
2-(3-amidinophenoxy)-N-[3-fluoro-4-(2-oxopiperidin-1-yl)phenyl]valeramide,
2-(3-amidinophenoxy)-N-[4-(2-oxopiperidin-1-yl)phenyl]acetamide,
2-(2-amidinophenoxy)-N-[4-(2-oxopiperidin-1-yl)phenyl]-2-phenylacetamide,
2-(4-amidinophenoxy)-N-[4-(2-oxopiperidin-1-yl)phenyl]-2-phenylacetamide,
3-(3-amidinophenyl)-N-[4-(2-oxopiperidin-1-yl)phenyl]propionamide,
2-(3-amidinophenoxy)-N-[3-fluoro-4-(2-oxopiperidin-1-yl)phenyl]-2-phenylacetamide,
3-(3-amidinophenyl)-N-[3-methyl-4-(2-oxopiperidin-1-yl)phenyl]propionamide,
(2S )-2-(3-amidinophenoxy)-N-[3-fluoro-4-(2-oxopiperidin-1-yl)phenyl]valeramide,
2-(3-amidinophenoxy)-N-[3-methyl-4-(2-caprolactam-1-yl)phenyl]-2-phenylacetamide,
2-(3-amidinophenylmethyl)-N-[4-(2-oxopiperidin-1-yl)phenyl]valeramide,
2-(3-amidinophenylmethyl)-N-[3-methyl-4-(2-oxopiperidin-1-yl)phenyl]valeramide,
2-(3-amidinophenoxy)-N-[4-(2-oxopiperazin-1-yl)phenyl]valeramide,
(2S )-2-(3-amidinophenoxy)-N-[4-(2-caprolactam-1-yl)phenyl]valeramide,
(2S )-2-(3-amidinophenoxy)-N-[3-methyl-4-(2-oxopiperidin-1-yl)phenyl]valeramide,
2-(3-amidinophenoxy)-N-[3-methyl-4-(2-oxopiperidin-1-yl)phenyl]-4-methylvaleramide,
2-(3-amidinophenoxy)-N-[4-(2-oxopiperidin-1-yl)phenyl]-4-methylvaleramide,
(2R)-2-(3-amidinophenoxy)-N-[4-(2-oxopiperidin-1-yl)phenyl]valeramide,
2-(3-amidinophenoxy)-N-[4-(2-oxopiperidin-1-yl)phenyl]propionamide,
2-(3-amidinophenoxy)-N-[3-methyl-4-(2-oxopiperidin-1-yl)phenyl]propionamide,
2-(3-amidinophenoxy)-N-[4-(2-oxopiperidin-1-yl)phenyl]butyramide,
2-(3-amidinophenoxy)-N-[3-methyl-4-(2-oxopiperidin-1-yl)phenyl]butyramide,
(2S )-2-(3-amidinophenoxy)-N-[3-methyl-4-(2-caprolactam-1-yl)phenyl]valeramide,
2-(3-amidinophenoxy)-N-[4-(2-oxopyridin-1-yl)phenyl]valeramide,
2-(3-amidinophenoxy)-N-[2,5-dimethyl-4-(2-oxopiperidin-1-yl)phenyl]valeramide,
2-(3-amidinophenoxy)-N-[3-methyl-4-(2-oxopyrrolidin-1-yl)phenyl]-2-phenylacetamide,
2-(3-amidinophenoxy)-N-[3-methyl-4-(2-oxopyrrolidin-1-yl)phenyl]valeramide,
2-(3-amidinophenoxy)-N-[2-methyl-4-(2-oxopiperidin-1-yl)phenyl]valeramide,
2-(3-amidinophenoxy)-N-(2-oxo-3,4,5,6-tetrahydro-2H-1,2'-bipyridinyl-5'-yl)valeramide,
2-(3-amidinophenoxy)-N-[2-methyl-4-(2-oxopiperidin-1-yl)phenyl]-2-phenylacetamide,
2-(3-amidinophenoxy)-N-(2-oxo-3,4,5,6-tetrahydro-2H-1,2'-bipyridinyl-5'-yl)-2-phenylacetamide,
2-(3-amidinophenoxy)-N-[3-fluoro-4-(2-oxopyrrolidin-1-yl)phenyl]valeramide,
2-(3-amidinophenoxy)-N-[3-fluoro-4-(2-oxopyrrolidin-1-yl)phenyl]-2-phenylacetamide,
2-(3-amidinophenoxy)-N-[4-(2-oxopiperidin-1-yl)phenyl]caproamide,
2-(3-amidinophenoxy)-N-[4-(2-oxopyrrolidin-1-yl)phenyl]butyramide,
2-(3-amidinophenoxy)-N-[4-(2-oxopiperidin-1-yl)phenyl]-3-methylbutyramide,
2-(3-amidinophenoxy)-N-[4-ethyl-3-(2-oxopyrrolidin-1-yl)phenyl]valeramide,
2-(3-amidinophenoxy)-N-[3-fluoro-4-(2-caprolactam-1-yl)phenyl]valeramide,
2-(3-amidinophenoxy)-N-[3-fluoro-4-(2-caprolactam-1-yl)phenyl]-2-phenylacetamide, acetate,
2-(3-amidinophenoxy)-N-[4-(2,6-dioxopiperidin-1-yl)phenyl]valeramide,
3-(3-amidinophenyl)-N-[4-(2-oxopiperidin-1-yl)phenyl]-2-phenylpropionamide,
3-(3-amidinophenyl)-N-[3-methyl-4-(2-oxopiperidin-1-yl)phenyl]-2-phenylpropionamide,
2-(3-amidinophenoxy)-N-[3-methoxy-4-(2,5-dioxopyrrolidin-1-yl)phenyl]valeramide,
2-(3-amidinophenoxy)-N-[3-(2-oxopiperidin-1-yl)propyl]-2-phenylacetamide,
2-(3-amidinophenylamino)-N-[4-(2-oxopiperidin-1-yl)phenyl]-4-methylvaleramide,
2-(3-amidinophenylamino)-N-[4-(2-oxopiperidin-1-yl)phenyl]-2-phenylacetamide,
2-(3-amidinophenylamino)-N-[4-(2-oxopyrrolidin-1-yl)phenyl]-4-methylvaleramide,
2-(3-amidinophenylamino)-N-[4-(2-oxopyrrolidin-1-yl)phenyl]-2-phenylacetamide,
2-(3-amidinophenylamino)-N-[4-(2-oxopiperidin-1-yl)phenyl]-2-(2-fluorophenyl)acetamide,
2-(3-amidinophenylamino)-N-[4-(2-oxopiperidin-1-yl)phenyl]acetamide,
(2S )-2-(3-amidinophenylamino) -N-[4-(2-caprolactam-1-yl)phenyl]-2-phenylacetamide,
(2S )-2-(3-amidinophenylamino)-N-[3-methyl-4-(2-oxopiperidin-1-yl)phenyl]-2-phenylacetamide,
(2S )-2-(3-amidinophenylamino)-N-[4-(2-oxopiperidin-1-yl)phenyl]-2-phenylacetamide,
2-(3-amidinophenylamino)-N-[4-(2-oxopiperidin-1-yl)phenyl]caproamide,
2-(3-amidinophenylamino)-N-[3-methyl-4-(2-oxopiperidin-1-yl)phenyl]-2-(2-fluorophenyl)acetamide,
(2S )-2-(2-amidinophenylamino)-N-[4-(2-oxopiperidin-1-yl)phenyl]-2-phenylacetamide,
(2R)-2-(2-amidinophenylamino)-N-[4-(2-oxopiperidin-1-yl)phenyl]-2-phenylacetamide,
(2S )-2-(3-amidinophenylamino)-N-[3-fluoro-4-(2-oxopiperidin-1-yl)phenyl]-2-phenylacetamide, 2-(3-amidinophenylamino)-N-[4-(2-oxopiperidin-1-yl)
phenyl]-2-(3-fluorophenyl)acetamide,
2-(3-amidinophenylamino)-N-[3-fluoro-4-(2-oxopiperidin-1-yl)phenyl]-2-(3-fluorophenyl)acetamide,
(2R)-2-(3-amidinophenylamino)-N-[3-methyl-4-(2-oxopiperidin-1-yl)phenyl]-4-methylvaleramide,
2-(3-amidinophenylamino)-N-[4-(2-oxopiperidin-1-yl)
phenyl]valeramide,
(2R)-2-(3-amidinophenylamino)-N-[4-(2-oxopiperidin-1-yl)phenyl]-4-methylvaleramide,
(2R)-2-(3-amidinophenylamino)-N-[4-(2-caprolactam-1-yl)phenyl]-4-methylvaleramide,
2-(3-amidinophenylamino)-N-[3-fluoro-4-(2-oxopiperidin-1-yl)phenyl]-2-(2-fluorophenyl)acetamide,
2-(3-amidinophenylamino)-N-[3-methyl-4-(2-caprolactam-1-yl)phenyl]-2-(2-fluorophenyl)acetamide,
(2R)-2-(3-amidinophenylamino)-N-[3-fluoro-4-(2-oxopiperidin-1-yl)phenyl]-4-methylvaleramide,
2-(3-amidinophenylamino)-N-[4-(2-oxopiperidin-1-yl)
phenyl]-4-trifluoro-3-methylbutyramide,
(2S )-2-(3-amidinophenylamino)-N-[4-(2-oxopiperidin-1-yl)benzyl]-2-phenylacetamide,
(2S )-2-(3-amidinophenylamino)-N-[4-(3-oxo-2-azabicyclo[2.2.2]oct-2-yl)phenyl]-2-phenylacetamide,
2-(3-amidinophenylamino)-N-[3-trifluoromethyl-4-(3-oxo-2-azabicyclo-[2.2.2]oct-2-yl)phenyl]-2-phenylacetamide,
2-(3-amidinophenylamino)-N-methyl-N-[4-(2-oxopiperidin-1-yl)phenyl]-2-phenylacetamide,
2-(3-aminocarbonylphenoxy)-N-[4-(2-oxopiperidin-1-yl)
phenyl]valeramide,
2-(3-aminocarbonylphenylamino)-N-[4-(2-oxopiperidin-1-yl)phenyl]-2-phenylacetamide,
2-(3-aminocarbonylphenoxy)-N-[4-(2-oxo-1H-pyridin-1-yl)benzyl]-2-phenylacetamide,
2-(3-aminocarbonylphenoxy)-N-[4-(2-caprolactam-1-yl)
phenyl]-2-phenylacetamide,
2-(3-aminocarbonylphenoxy)-N-[4-(2-caprolactam-1-yl)
phenyl]-2-phenylacetamide,
2-(3-aminocarbonylphenylamino)-N-[4-(2-oxopiperidin-1-yl)phenyl]-2-(2-fluorophenyl)acetamide,
3-(3-aminocarbonylphenyl)-N-[4-(2-oxopiperidin-1-yl)
phenyl]propionamide,
2-(3-aminocarbonylphenoxy)-N-[4-(2-oxo-1H-pyridin-1-yl)phenyl]-2-phenylacetamide,
2-(3-aminocarbonylphenoxy)-N-[3-methyl-4-(2-oxopiperidin-1-yl)phenyl]-2-phenylacetamide,
2-(3-aminocarbonylphenoxy)-N-[4-(4-oxo-4H-pyridin-1-yl)phenyl]-2-phenylacetamide,
2-(3-aminocarbonylphenylamino)-N-[4-(2-oxopiperidin-1-yl)phenyl]acetamide,
(2S )-2-(3-aminocarbonylphenylamino)-N-[3-methyl-4-(2-oxopiperidin-1-yl)phenyl]-2-phenylacetamide,
(2S )-2-(3-aminocarbonylphenylamino)-N-[4-(2-caprolactam-1-yl)phenyl]-2-phenylacetamide,
(2R)-2-(3-aminocarbonylphenylamino)-N-[4-(2-oxopiperidin-1-yl)phenyl]-2-phenylacetamide,
(2S )-2-(3-aminocarbonylphenylamino)-N-[4-(2-oxopiperidin-1-yl)phenyl]-2-phenylacetamide,
2-(3-aminocarbonylphenylamino)-N-[4-(2-caprolactam-1-yl)phenyl]-2-(2-fluorophenyl)acetamide,
2-(3-aminocarbonylphenylamino)-N-[4-(2-oxopiperidin-1-yl)phenyl]-2-(2-thienyl)acetamide,
2-(4-aminocarbonylphenoxy)-N-[4-(2-oxopiperidin-1-yl)
phenyl]-2-phenylacetamide,
2-(2-aminocarbonylphenoxy)-N-[4-(2-oxopiperidin-1-yl)
phenyl]-2-phenylacetamide,
2-(3-aminocarbonylphenoxy)-N-[2-fluoro-4-(2-oxopiperidin-1-yl)phenyl]-2-phenylacetamide,
2-(3-aminocarbonylphenoxy)-N-[2-fluoro-4-(2-caprolactam-1-yl)phenyl]-2-phenylacetamide,
(2S )-2-(2-aminocarbonylphenyl)-N-[4-(2-oxopiperidin-1-yl)phenyl]-2-phenylacetamide,
(2R)-2-(2-aminocarbonylphenyl)-N-[4-(2-oxopiperidin-1-yl)phenyl]-2-phenylacetamide,
2-(3-aminocarbonylphenoxy)-N-[3-methyl-4-(2-caprolactam-1-yl)phenyl]-2-phenylacetamide,
(2S )-2-(3-aminocarbonylphenylamino)-N-[4-(2-oxopyridin-1-yl)phenyl]-2-phenylacetamide,
2-(3-aminocarbonylphenylamino)-N-[4-(2-oxopiperidin-1-yl)phenyl]valeramide,
2-(3-aminocarbonyl-4-fluorophenylamino)-N-[4-(2-oxopiperidin-1-yl)phenyl]-2-phenylacetamide,
2-(3-aminocarbonylphenylamino)-N-[3-trifluoromethyl-4-(3-oxo-2-azabicyclo[2.2.2]oct-2-yl)phenyl]-2-phenylacetamide,
2-(3-N,N-diethylaminocarbonylphenoxy)-N-[4-(2-oxopiperidin-1-yl)phenyl]-2-phenylacetamide,
2-(3-aminocarbonylphenoxy)-N-[4-(2-oxopiperazin-1-yl)
phenyl]-2-phenylacetamide,
2-[3-(N-hydroxyamidino)phenylamino]-N-[4-(2-oxopiperidin-1-yl)phenyl]-2-phenylacetamide,
2-[3-(N-hydroxyamidino)phenoxy]-N-[4-(2-oxopiperidin-1-yl)phenyl]-2-phenylacetamide,
2-[3-(N-hydroxyamidino)phenyl]-N-[4-(2-oxopiperidin-1-yl)phenyl]propionamide,
2-[3-(N-hydroxyamidino)phenylamino]-N-[4-(2-oxopiperidin-1-yl)phenyl]acetamide,
2-[3-(N-hydroxyamidino)phenoxy]-N-[4-(2-oxopiperidin-1-yl)phenyl]valeramide,
(2R)-[2-(3-(N-hydroxyamidino)phenylamino]-N-[4-(2-caprolactam-1-yl)phenyl]-2-phenylacetamide,
2-[3-(N-hydroxyamidino)phenylamino]-N-[4-(2-oxopiperidin-1-yl)phenyl]-2-(2-trifluoromethylphenyl)acetamide,
2-[3-(N-hydroxyamidino)phenylamino]-N-[3-methyl-4-(2-oxopiperidin-1-yl)phenyl]-2-(2-fluorophenyl)acetamide,
2-[3-(N-hydroxyamidino)phenylamino]-N-[4-(2-oxopiperidin-1-yl)phenyl]-2-(2-thienyl)acetamide,
2-[3-(N-hydroxyamidino)phenoxy]-N-[3-methyl-4-(2-oxopiperidin-1-yl)phenyl]valeramide,
(2S )-2-[3-(N-hydroxyamidino)phenylamino]-N-[3-fluoro-4-(2-oxopiperidin-1-yl)phenyl]-2-phenylacetamide,
3-[3-(N-hydroxyamidino)phenyl]-N-[3-methyl-4-(2-oxopiperidin-1-yl)phenyl]propionamide,
(2S )-2-[3-(N-hydroxyamidino)phenylamino]-N-[4-(2-oxopiperidin-1-yl)phenyl]-4-methylvaleramide,
2-[3-(N-hydroxyamidino)phenoxy]-N-[4-(2-oxopiperidin-1-yl)phenyl]valeramide,
2-[3-(N-hydroxyamidino)phenoxy]-N-[4-(2-oxo-1H-pyrazin-1-yl)phenyl]valeramide,
(2S )-2-[3-(N-hydroxyamidino)phenylamino]-N-[4-(2-oxopiperidin-1-yl)phenyl]-2-phenylacetamide,
(2R)-2-[3-(N-hydroxyamidino)phenylamino]-N-[4-(2-oxopiperidin-1-yl)phenyl]-4-methylvaleramide,
2-[3-(N-hydroxyamidino)phenylamino]-N-[4-(2-oxopiperidin-1-yl)phenyl]valeramide,
2-[3-(N-hydroxyamidino)phenylamino]-N-[3-methyl-4-(2-oxopiperidin-1-yl)phenyl]-4-methylvaleramide,
2-[3-(N-hydroxyamidino)phenoxy]-N-[4-(2-oxopyridin-1-yl)phenyl]valeramide, (2R)-2-[3-(N-hydroxyamidino)phenylamino]-N-[4-(2-caprolactam-1-yl)phenyl]-4-methylvaleramide,
(2R)-2-[3-(N-hydroxyamidino)phenoxy]-N-[4-(2-oxopiperidin-1-yl)phenyl]valeramide,
(2S)-2-[3-(N-hydroxyamidino)phenoxy]-N-[4-(2-oxopiperidin-1-yl)phenyl]valeramide,
2-[3-(N-hydroxyamidino)phenoxy]-N-[4-(2-oxopiperidin-1-yl)phenyl]-4-methylvaleramide,
2-[3-(N-hydroxyamidino)phenylamino]-N-[4-(2-oxopiperidin-1-yl)phenyl]-3-methyl-4-trifluorobutyramide,
(2S)-2-[3-(N-hydroxyamidino)phenylamino]-N-[4-(2-oxopiperidin-1-yl)benzyl]-2-phenylacetamide,
(2S)-2-[3-(N-hydroxyamidino)phenylamino]-N-[4-(3-oxo-2-azabicyclo-[2.2.2]oct-2-yl)phenyl]-2-phenylacetamide,
2-[3-(N-hydroxyamidino)phenoxy]-N-[4-(2-oxopiperidin-1-yl)phenyl]butyramide,
2-[3-(N-hydroxyamidino)phenoxy]-N-[4-(2-oxopiperidin-1-yl)phenyl]propionamide,
2-[3-(N-hydroxyamidino)phenylamino]-N-[3-trifluoromethyl-4-(3-oxo-2-azabicyclo[2.2.2]oct-2-yl)phenyl]-2-phenylacetamide,
3-[3-(N-hydroxyamidino)phenyl]-N-[4-(2-oxopiperidin-1-yl)phenyl]-2-phenylpropionamide,
3-[3-(N-hydroxyamidino)phenyl]-N-[3-methyl-4-(2-oxopiperidin-1-yl)phenyl]-2-phenylpropionamide,
2-(3-aminomethylphenylamino)-N-[3-methyl-4-(2-oxopiperidin-1-yl)phenyl]-2-(2-fluorophenyl)acetamide,
2-(3-aminomethylphenoxy)-N-[4-(2-oxopiperidin-1-yl)phenyl]-2-phenylacetamide, hydrochloride,
2-(3-aminomethylphenylamino)-N-[4-(2-oxopiperidin-1-yl)phenyl]-2-(2-fluorophenyl)acetamide,
3-(3-aminomethylphenyl)-N-[4-(2-oxopiperidin-1-yl)phenyl]propionamide,
2-(3-aminomethylphenylamino)-N-[4-(2-oxopiperidin-1-yl)phenyl]acetamide,
2-(3-aminomethylphenoxy)-N-[4-(2-oxopiperidin-1-yl)phenyl]valeramide,
(2S)-2-(3-aminomethylphenylamino)-N-[4-(2-caprolactam-1-yl)phenyl]-2-phenylacetamide,
(2S)-2-(3-aminomethylphenylamino)-N-[3-methyl-4-(2-oxopiperidin-1-yl)phenyl]acetamide,
2-(3-aminomethylphenylamino)-N-[4-(2-oxopiperidin-1-yl)phenyl]-2-(2-trifluoromethylphenyl)acetamide,
(2S)-2-(3-aminomethylphenylamino)-N-[4-(2-oxopiperidin-1-yl)phenyl]-2-phenylacetamide,
(2R)-2-(3-aminomethylphenylamino)-N-[4-(2-oxopiperidin-1-yl)phenyl]-2-phenylacetamide,
2-(3-aminomethylphenylamino)-N-[4-(2-oxopiperidin-1-yl)phenyl]-2-(2-methylphenyl)acetamide,
2-(3-aminomethylphenylamino]-N-[4-(2-caprolactam-1-yl)phenyl]-2-(2-fluorophenyl)acetamide,
2-(3-aminomethylphenylamino)-N-[3-methyl-4-(2-oxopiperidin-1-yl)phenyl]-2-(2-methylphenyl)acetamide,
2-(3-aminomethylphenylamino)-N-[3-methyl-4-(2-oxopiperidin-1-yl)phenyl]-2-(2-fluorophenyl)acetamide,
2-(3-aminomethylphenoxy)-N-[3-methyl-4-(2-oxopiperidin-1-yl)phenyl]valeramide,
2-(3-aminomethylphenylamino)-N-[4-(2-oxopiperidin-1-yl)phenyl]-2-(2-thienyl)acetamide,
2-(3-aminomethylphenylamino)-N-[3-fluoro-4-(2-oxopiperidin-1-yl)phenyl]-2-(3-fluorophenyl)acetamide,
(2S)-2-(3-aminomethylphenylamino)-N-[3-fluoro-4-(2-oxopiperidin-1-yl)phenyl]-2-phenylacetamide,
(2S)-2-(3-aminomethylphenylamino)-N-[3-methyl-4-(2-oxopiperidin-1-yl)phenyl]-2-phenylacetamide, (2S)-2-(2-aminomethylphenylamino)-N-[4-(2-oxopiperidin-1-yl)phenyl]-2-phenylacetamide,
2-(2-aminomethylphenyl)-N-[4-(2-oxopiperidin-1-yl)phenyl]acetamide,
2-(2-aminomethylphenoxy)-N-[4-(2-oxopiperidin-1-yl)phenyl]-2-phenylacetamide,
2-(4-aminomethylphenoxy)-N-[4-(2-oxopiperidin-1-yl)phenyl]-2-phenylacetamide,
2-(3-aminomethylphenylamino)-N-[4-(2-oxopiperidin-1-yl)phenyl]-2-(3-fluorophenyl)acetamide,
2-(3-aminomethylphenoxy)-N-[3-methyl-4-(2-caprolactam-1-yl)phenyl]-2-phenylacetamide,
(2R)-2-(3-aminomethylphenylamino)-N-[3-methyl-4-(2-caprolactam-1-yl)phenyl]-2-phenylacetamide,
(2R)-2-(2-aminomethylphenylamino)-N-[4-(2-oxopiperidin-1-yl)phenyl]-2-phenylacetamide,
(2S)-2-(3-aminomethylphenylamino)-N-[3-methyl-4-(2-caprolactam-1-yl)phenyl]-2-phenylacetamide,
2-(3-aminomethylphenylamino)-N-[4-(2-caprolactam-1-yl)phenyl]-4-methylvaleramide,
(2R)-2-(3-aminomethylphenylamino)-N-[3-methyl-4-(2-oxopiperidin-1-yl)phenyl]-2-phenylacetamide, hydrochloride,
(2S)-2-(3-aminomethylphenylamino)-N-[4-(2-oxopyridin-1-yl)phenyl]-2-phenylacetamide,
2-(3-aminomethylphenylamino)-N-[4-(2-oxopiperidin-1-yl)phenyl]valeramide,
2-(3-aminomethylphenylamino)-N-[4-(2-oxopiperidin-1-yl)phenyl]-4-methylvaleramide,
(2R)-2-(3-aminomethylphenylamino)-N-[3-methyl-4-(2-oxopiperidin-1-yl)phenyl]-4-methylvaleramide,
(2R)-2-(3-aminomethylphenylamino)-N-[3-fluoro-4-(2-oxopiperidin-1-yl)phenyl]-4-methylvaleramide,
(2R)-2-(3-aminomethylphenylamino)-N-[4-(2-caprolactam-1-yl)phenyl]-4-methylvaleramide,
(2S)-2-(3-aminomethylphenylamino)-N-[2,5-dimethyl-4-(2-oxopiperidin-1-yl)phenyl]-2-phenylacetamide,
2-(3-aminomethylphenylamino)-N-[3-fluoro-4-(2-oxopiperidin-1-yl)phenyl]-2-(2-fluorophenyl)acetamide,
2-(3-aminomethylphenylamino)-N-[3-methyl-4-(2-caprolactam-1-yl)phenyl]-2-(2-fluorophenyl)acetamide,
2-(3-aminomethylphenylamino)-N-[3-methyl-4-(2-oxopiperidin-1-yl)phenyl]-2-(2,4-difluorophenyl)acetamide,
2-(3-aminomethylphenylamino)-N-[4-(2-oxopiperidin-1-yl)phenyl]-2-(2,4-difluorophenyl)acetamide,
(2S)-2-(3-aminomethylphenylamino)-N-[3-methyl-4-(2-oxopyrrolidin-1-yl)phenyl]-2-phenylacetamide,
(2S)-2-(3-aminomethylphenylamino)-N-[3-methyl-4-(2-oxopiperidin-1-yl)phenyl]-4-methylvaleramide,
2-(3-aminomethylphenylamino)-N-methyl-N-[4-(2-oxopiperidin-1-yl)phenyl]-2-phenylacetamide,
2-(3-aminoethylphenylamino)-N-[4-(2-oxopiperidin-1-yl)phenyl]-2-phenylacetamide, hydrochloride,
2-(3-aminomethylphenylamino)-N-[3-methyl-4-(2-oxopyrrolidin-1-yl)phenyl]-2-(2-fluorophenyl)acetamide,
2-(3-aminomethylphenylamino)-N-[4-(2-oxopiperidin-1-yl)phenyl]-4-trifluoro-3-methylbutyramide,
2-(3-aminomethylphenylamino)-N-[4-(2-oxopiperidin-1-yl)benzyl]-2-phenylacetamide,
(2S)-2-(3-aminomethylphenylamino)-N-[4-(3-oxo-2-azabicyclo[2.2.2]oct-2-yl)phenyl]-2-phenylacetamide,
2-(3-aminomethylphenylamino)-N-[3-fluoro-4-(2-oxopyrrolidin-1-yl)phenyl]-2-(2-fluorophenyl)acetamide,
2-(3-aminomethylphenylamino)-N-[4-(2-oxopyrrolidin-1-yl)phenyl]-2-phenylacetamide, 2-(3-aminomethylphenylamino)-N-[4-(2-oxopyrrolidin-1-yl)phenyl]-2-(2-fluorophenyl)acetamide,
2-(3-aminomethylphenylamino)-N-[4-ethyl-3-(2-oxopyrrolidin-1-yl)phenyl]-2-phenylacetamide,
(2S )-2-(3-aminomethylphenylamino)-N-[3-methoxy-4-(3-oxo-2-azabicyclo-[2.2.2]oct-2-yl)phenyl]-2-phenylacetamide,
2-(3-aminomethylphenylamino)-N-[3-fluoro-4-(2-caprolactam-1-yl)phenyl]-2-(2-fluorophenyl)acetamide,
(2S )-2-(3-aminomethylphenylamino)-N-[3-fluoro-4-(2-caprolactam-1-yl)phenyl]-2-phenylacetamide,
(2S )-2-(3-aminomethylphenylamino)-N-[3-trifluoromethyl-4-(3-oxo-2-azabicyclo[2.2.2]oct-2-yl)phenyl]-2-phenylacetamide,
2-(3-aminomethylphenylamino)-N-[3-methyl-4-(3-oxo-2-azabicyclo[2.2.2]oct-2-yl)phenyl]-2-phenylacetamide,
(2S )-2-(3-aminomethylphenylamino)-N-[3-methoxy-4-(3-oxo-2-azabicyclo-[2.2.2]oct-2-yl)phenyl]-2-phenylacetamide,
2-(3-aminomethylphenylamino)-N-[3-trifluoromethyl-4-(2-oxopiperidin-1-yl)phenyl]-2-phenylacetamide,
2-(3-aminomethylphenylamino)-N-[3-methoxy-4-(2-oxopiperidin-1-yl)phenyl]-2-phenylacetamide,
2-(3-aminomethylphenylamino)-N-[3-methyl-4-(3-oxo-2-azabicyclo[2.2.2]oct-2-yl)phenyl]-2-(2-fluorophenyl)acetamide,
2-(3-aminomethyl-4-fluorophenylamino)-N-[4-(2-oxopiperidin-1-yl)phenyl]-2-phenylacetamide,
2-(3-aminomethylphenylamino)-N-[3-methyl-4-(3-oxo-2-azabicyclo[2.2.2]oct-2-yl)phenyl]-2-(2-fluorophenyl)acetamide,
2-(3-aminomethylphenylamino)-N-[3-chloro-4-(2-oxopyrrolidin-1-yl)phenyl]-2-(2-fluorophenyl)acetamide,
2-(3-aminomethylphenylamino)-N-[3-methoxy-4-(2-oxopiperidin-1-yl)phenyl]-2-(2-fluorophenyl)acetamide,
2-(3-aminomethylphenylamino)-N-[3-trifluoromethyl-4-(3-oxo-2-azabicyclo[2.2.2]oct-2-yl)phenyl]-2-phenylacetamide,
2-(3-aminomethylphenylamino)-N-[3-trifluoromethyl-4-(2-oxopiperidin-1-yl)phenyl]-2-phenylacetamide,
3-(3-aminomethylphenyl)-N-[4-(2-caprolactam-1-yl)phenyl]-2-phenylpropionamide,
2-(3-aminomethylphenoxy)-N-[3-methyl-4-(2-oxopyrrolidin-1-yl)phenyl]-2-(2-fluorophenyl)acetamide,
3-(3-aminomethylphenyl)-N-[4-(2-oxopiperidin-1-yl)phenyl]-2-phenylpropionamide,
2-(3-aminomethylphenoxy)-N-[3-methyl-4-(2-caprolactam-1-yl)phenyl]-2-(2-fluorophenyl)acetamide,
3-(3-aminomethylphenyl)-N-[3-methyl-4-(2-oxopiperidin-1-yl)phenyl]-2-phenylpropionamide,
2-(3-aminomethylphenoxy)-N-[4-(2-oxopiperidin-1-yl)phenyl]-2-(2-fluorophenyl)acetamide,
2-(3-aminomethylphenoxy)-N-[3-methyl-4-(2-oxopiperidin-1-yl)phenyl]-2-(2-fluorophenyl)acetamide,
3-(3-aminomethylphenyl)-N-[3-methyl-4-(2-oxopyrrolidin-1-yl)phenyl]-2-phenylpropionamide,
(2S )-2-(3-aminomethylphenylamino)-N-[4-(5,5-dimethyl-2-oxopyrrolidin-1-yl)phenyl]-2-phenylacetamide,
(2S )-2-(3-aminomethylphenylamino)-N-[3-methyl-4-(2-oxo-1,3-oxazinan-3-yl)phenyl]-2-phenylacetamide,
(2S )-2-(3-aminomethylphenylamino)-N-[3-methyl-4-(2-oxooxazolidin-3-yl)phenyl]-2-phenylacetamide,
(2S )-2-(3-aminoethylphenylamino)-N-[4-(2-oxopiperidin-1-yl)phenyl]-2-phenylacetamide,
2-(3-amidinophenoxy)-N-[4-(2-oxopiperazin-1-yl)phenyl]-2-phenylacetamide,
2-[3-(5-methyl-1,2,4-oxadiazol-3-yl)phenoxy]-N-[4-(2,6-dioxopiperidin-1-yl)phenyl]-2-phenylacetamide,
2-(3-amidinophenoxy)-N-[4-(2,6-dioxopiperidin-1-yl)phenyl]-2-phenylacetamide,
2-(3-amidinophenoxy)-N-[3-trifluoromethyl-4-(2,6-dioxopiperidin-1-yl)phenyl]valeramide,
2-(3-amidinophenoxy)-N-[3-chloro-4-(2,5-dioxopyrrolidin-1-yl)phenyl]valeramide, acetate,
2-[3-(5-methyl-1,2,4-oxadiazol-3-yl)phenoxy]-N-[3-trifluoromethyl-4-(2,5-dioxopyrrolidin-yl)phenyl]-2-valeramide,
2-[3-(5-methyl-1,2,4-oxadiazol-3-yl)phenoxy]-N-[3-chloro-4-(2,5-dioxopyrrolidin-1-yl)phenyl]-2-valeramide,
2-[3-(5-methyl-1,2,4-oxadiazol-3-yl)phenoxy]-N-[3-methoxy-4-(2,5-dioxopyrrolidin-1-yl)phenyl]-2-valeramide,
2-[3-(5-methyl-1,2,4-oxadiazol-3-yl)phenoxy]-N-[4-(2,5-dioxopyrrolidin-1-yl)phenyl]-2-valeramide,
3-(3-amidinophenoxy)-N-[3-chloro-4-(2-oxopiperidin-1-yl)phenyl]-2-phenylacetamide,
3-(3-amidinophenoxy)-N-[3-chloro-4-(2-oxopiperidin-1-yl)phenyl]valeramide,
3-(3-amidinophenoxy)-N-[3-chloro-4-(2-oxopiperidin-1-yl)phenyl]butyramide,
2-(3-amidino-4-fluorophenylamino)-N-[4-(2-oxopiperidin-1-yl)phenyl]-2-phenylacetamide,
3-(3-aminomethylphenyl)-N-[3-methyl-4-(2-oxopiperidin-1-yl)phenyl]-2-(2-fluorophenyl)propionamide,
3-(3-aminomethylphenyl)-N-[4-(2-oxopiperidin-1-yl)phenyl]-2-(2-fluorophenyl)propionamide,
3-(3-aminomethylphenylamino)-N-[3-chloro-4-(2-oxopiperidin-1-yl)phenyl]-2-(2-fluorophenyl)acetamide,
3-(3-aminomethylphenylamino)-N-[3-chloro-4-(2-oxopiperidin-1-yl)phenyl]-2-phenylacetamide,
3-(3-aminomethylphenoxy)-N-[3-chloro-4-(2-oxopiperidin-1-yl)phenyl]-2-(2-fluorophenyl)acetamide,
3-(3-aminomethylphenyl)-N-[3-methyl-4-(2-oxopyrrolidin-1-yl)phenyl]-2-(2-fluorophenyl)propionamide,
3-(3-aminomethylphenyl)-N-[3-chloro-4-(2-oxopiperidin-1-yl)phenyl]-2-(2-fluorophenyl)propionamide,
3-(3-aminomethylphenylamino)-N-[4-(2,6-dioxopiperidin-1-yl)phenyl]-2-phenylacetamide, trifluoroacetate, ESI 443;
2-(3-aminomethylphenylamino)-N-[3-chloro-4-(2,5-dioxopyrrolidin-1-yl)phenyl]-2-phenylacetamide,
2-(3-aminomethyl-4-fluorophenylamino)-N-[3-methyl-4-(3-oxo-2-azabicyclo[2.2.2]oct-2-yl)phenyl]-2-phenylacetamide,
2-(3-amidinophenoxy)-N-[3-carboxymethoxy-4-(2-oxopiperidin-1-yl)phenyl]-2-phenylacetamide,
2-(3-amidinophenoxy)-N-[3-ethoxycarbonylmethoxy-4-(2-oxopiperidin-1-yl)phenyl]-2-phenylacetamide,
2-(3-amidinophenoxy)-N-[3-ethoxycarbonylmethoxy-4-(2-oxopiperidin-1-yl)phenyl]valeramide,
3-(3-amidinophenoxy)-N-[3-carboxymethoxy-4-(2-oxopiperidin-1-yl)phenyl]valeramide,
3-(3-amidinophenoxy)-N-[3-carboxymethoxy-4-(2-oxopiperidin-1-yl)phenyl]-2-phenylacetamide,
2-[3-(N-hydroxyamidino)phenoxy]-N-[3-ethoxycarbonylmethoxy-4-(2-oxopiperidin-1-yl)phenyl]-2-phenylacetamide,
2-[3-(N-hydroxyamidino)phenoxy]-N-[3-ethoxycarbonylmethoxy-4-(2-oxopiperidin-1-yl)phenyl]valeramide, 2-(3-aminomethylphenylamino)-N-[3-methyl-4-(3-oxo-2-azabicyclo[2.2.2]oct-2-yl)phenyl]-2-(2-fluorophenyl)acetamide, 2-(3-aminomethylphenylamino)-N-[3-methyl-4-(2-oxooxazolidin-3-yl)phenyl]-2-(2-fluorophenyl)acetamide, 3-(3-aminomethylphenylamino)-N-[3-methoxy-4-(2-oxopiperidin-1-yl)phenyl]-2-(2-fluorophenyl)acetamide, 3-(3-aminomethylphenylamino)-N-[3-chloro-4-(2-oxopyrrolidin-1-yl)phenyl]-2-phenylacetamide, 2-(3-aminomethylphenoxy)-N-[3-methyl-4-(3-oxo-2-azabicyclo[2.2.2]oct-2-yl)phenyl]-2-(2-fluorophenyl)acetamide, 3-(3-aminomethylphenylamino)-N-[4-(5,5-dimethyl-2-oxopyrrolidin-1-yl)phenyl]-2-(2-fluorophenyl)acetamide, 3-(3-aminomethylphenoxy)-N-[4-(5,5-dimethyl-2-oxopyrrolidin-1-yl)phenyl]-2-(2-fluorophenyl)acetamide, 2-(3-aminomethylphenoxy)-N-[3-methyl-4-(2-oxooxazolidin-3-yl)phenyl]-2-(2-fluorophenyl)acetamide, 3-(3-aminomethylphenoxy)-N-[3-methoxy-4-(2-oxopiperidin-1-yl)phenyl]-2-(2-fluorophenyl)acetamide, and their pharmaceutically acceptable salt and stereoisomers, including mixtures thereof in all ratios.

3. Medicament comprising at least one compound of the formula I according to claim 1 and/or its pharmaceutically acceptable salt and stereoisomers, including mixtures thereof in all ratios, and, optionally, excipients.

4. Medicament comprising at least one compound of the formula I according to claim 1 and/or its pharmaceutically acceptable salt and stereoisomers, including mixtures thereof in all ratios, and at least one further different medicament active ingredient.

5. Compounds according to claim 1, in which $R^2$ is H.

6. Compounds according to claim 1, in which $R^1$ is —C(=NH)—$NH_2$ which is unsubstituted or monosubstituted by OH, or is

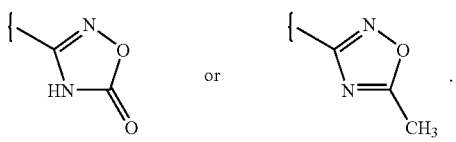

7. Compounds according to claim 1, in which Ar is phenyl which is unsubstituted or monosubstituted or disubstituted by Hal, A, $OR^4$ or O—$[C(R^4)_2]_o$—$COOR^3$.

8. Compounds according to claim 1, in which W is —$OC(R^3)_2$— or —$NR^3C(R^3)_2$—.

9. Compounds according to claim 1, in which W is —$OC(R^3)_2$— or —$NR^3C(R)_2$—, $R^3$ is H, A or —$(CH_2)_n$—Ar, and Ar is phenyl which is unsubstituted or monosubstituted or disubstituted by Hal, A, $OR^4$ or O—$[C(R^4)_2]_o$—$COOR^3$.

10. Compounds according to claim 1, in which Y is alkylene or Ar-diyl, and Ar is phenyl which is unsubstituted or monosubstituted or disubstituted by Hal, A, $OR^4$ or O—$[C(R^4)_2]_o$—$COOR^3$.

11. Compounds according to claim 1, in which $R^1$ is —C(=NH)—$NH_2$ which is unsubstituted or monosubstituted by OH, or is

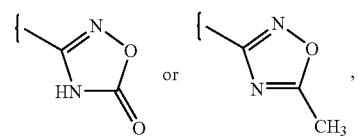

$R^2$ is H, $R^3$ is H, A or —$(CH_2)_n$—Ar,

W is —$OC(R^3)_2$— or —$NR^3C(R^3)_2$—,

Y is alkylene or Ar-diyl,

T is dimethylamino, diethylamino, 2-oxopiperidin-1-yl, 2-oxopyrrolidin-1-yl, 5,5-dimethyl-2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,5-dioxopyrrolidin-1-yl, 2-oxo-1,3-oxazolidin-3-yl, 2-azabicyclo[2.2.2]octan-3-on-2-yl or 3-oxo-2H-pyridazin-2-yl, and Ar is phenyl which is unsubstituted or monosubstituted or disubstituted by Hal, A, $OR^4$ or O—$[C(R^4)_2]_o$—$COOR^3$.

12. A method for the treatment of thrombosis, myocardial infarction, arteriosclerosis, inflammation, apoplexia, angina pectoris, restenosis after angioplasty, or claudicatio intermittens, which comprises administering to a patient in need thereof an effective amount of a compound according to claim 1 and/or a physiologically acceptable salt thereof.

13. A method according to claim 12, further comprising administering to a patient at least one further different medicament active ingredient for such treatment.

14. A kit comprising separately provided dosages of:

(a) a pharmaceutically effective amount of a compound of the formula I according to claim 1 and/or a pharmaceutically acceptable salt or stereoisomer thereof, including mixtures thereof in all ratios, and (b) a pharmaceutically effective amount of a further different medicament active ingredient.

* * * * *

UNITED STATES PATENT AND TRADEMARK OFFICE
CERTIFICATE OF CORRECTION

PATENT NO. : 7,273,867 B2 Page 1 of 1
APPLICATION NO. : 10/466680
DATED : September 25, 2007
INVENTOR(S) : Dieter Dorsch et al.

It is certified that error appears in the above-identified patent and that said Letters Patent is hereby corrected as shown below:

Column 60, after line 49, insert:
2-(3-amidinophenoxy)-N-[4-(2-oxopiperidin-1-yl)benzyl]-2-phenylacetamide, Signed and Sealed this Nineteenth Day of February, 2008

JON W. DUDAS
*Director of the United States Patent and Trademark Office*